US012807967B2

(12) United States Patent
Kim et al.

(10) Patent No.: US 12,807,967 B2
(45) Date of Patent: Nov. 24, 2026

(54) RECOMBINANT CHIMERIC ADENOVIRAL VECTOR SUBSTITUTED BY KNOB GENE OF CHIMPANZEE ADENOVIRUS SEROTYPE 6, AND APPLICATION THEREOF

(71) Applicant: GENEMATRIX, INC., Seongnam-si (KR)

(72) Inventors: Soo Ok Kim, Seongnam-si (KR); Suk Joon Kim, Seongnam-si (KR); Sun Pyo Hong, Seoul (KR); Hyun Ju Kim, Yongin-si (KR); Sang Hyun Lee, Seongnam-si (KR); Sun Ok Jang, Seoul (KR)

(73) Assignee: GENEMATRIX, INC., Seoul (KR)

( * ) Notice: Subject to any disclaimer, the term of this patent is extended or adjusted under 35 U.S.C. 154(b) by 422 days.

(21) Appl. No.: 18/551,261

(22) PCT Filed: Mar. 24, 2022

(86) PCT No.: PCT/KR2022/004159
§ 371 (c)(1),
(2) Date: Sep. 19, 2023

(87) PCT Pub. No.: WO2022/211373
PCT Pub. Date: Oct. 6, 2022

(65) Prior Publication Data

US 2025/0277234 A1 Sep. 4, 2025

(30) Foreign Application Priority Data

Mar. 29, 2021 (KR) ........................ 10-2021-0040269
Mar. 21, 2022 (KR) ........................ 10-2022-0034885

(51) Int. Cl.
*C12N 15/86* (2006.01)
*A61K 39/00* (2006.01)
*C07K 14/005* (2006.01)

(52) U.S. Cl.
CPC ............ *C12N 15/86* (2013.01); *C07K 14/005* (2013.01); *A61K 39/00* (2013.01); *C12N 2710/10321* (2013.01); *C12N 2710/10322* (2013.01); *C12N 2710/10343* (2013.01); *C12N 2710/10344* (2013.01); *C12N 2710/20034* (2013.01); *C12N 2770/20034* (2013.01)

(58) Field of Classification Search
CPC .......... C12N 15/86; C12N 2710/10322; C12N 2710/10343; C12N 2710/10344
See application file for complete search history.

(56) References Cited

U.S. PATENT DOCUMENTS

2015/0352203 A1* 12/2015 Wilson ................. C07K 14/005 435/235.1

FOREIGN PATENT DOCUMENTS

WO WO-2013036791 A2 * 3/2013 ............. A61K 39/04

OTHER PUBLICATIONS

Ersching J, Hernandez MI, Cezarotto FS, Ferreira JD, Martins AB, Switzer WM, Xiang Z, Ertl HC, Zanetti CR, Pinto AR. Neutralizing antibodies to human and simian adenoviruses in humans and New-World monkeys. Virology. Nov. 10, 2010;407(1):1-6. (Year: 2010).*

Kahl CA, Bonnell J, Hiriyanna S, Fultz M, Nyberg-Hoffman C, Chen P, King CR, Gall JG. Potent immune responses and in vitro pro-inflammatory cytokine suppression by a novel adenovirus vaccine vector based on rare human serotype 28. Vaccine. Aug. 9, 2010;28(35):5691-702. (Year: 2010).*

Khallouf H, Grabowska AK, Riemer AB. Therapeutic Vaccine Strategies against Human Papillomavirus. Vaccines (Basel). Jun. 13, 2014;2(2):422-62. doi: 10.3390/vaccines2020422. PMID: 26344626; PMCID: PMC4494257. (Year: 2014).*

Saha B, Wong CM, Parks RJ. The adenovirus genome contributes to the structural stability of the virion. Viruses. Sep. 24, 2014;6(9):3563-83. doi: 10.3390/v6093563. PMID: 25254384; PMCID: PMC4189039. (Year: 2014).*

Makrides SC. Vectors for gene expression in mammalian cells. New Comprehensive Biochemistry. 2003;38:9-26. doi: 10.1016/S0167-7306(03)38002-0. Epub Jan. 7, 2004. PMCID: PMC7147855. (Year: 2003).*

* cited by examiner

*Primary Examiner* — Fereydoun G Sajjadi
*Assistant Examiner* — Qinhua Gu

(57) ABSTRACT

The present invention is a chimeric adenovirus vector in which the knob domain of the end of the fiber protein of human adenovirus type 5 is replaced with the knob gene of chimpanzee adenovirus serotype 6 and/or in addition the hexon protein of human adenovirus type 5 is replaced with hypervariable regions 1-7 of human adenovirus serotype 28. The present invention not only provides the optimal adenovirus vector in the development of treatments or vaccines for various diseases, but also when the chimeric adenovirus vector produced in the present invention is infected with a host cell for production, it can contribute to improved productivity by exhibiting superior cell infection ability compared to the recombinant HAdV-5 vector-based vaccine.

8 Claims, 23 Drawing Sheets

Specification includes a Sequence Listing.

【Fig. 1】
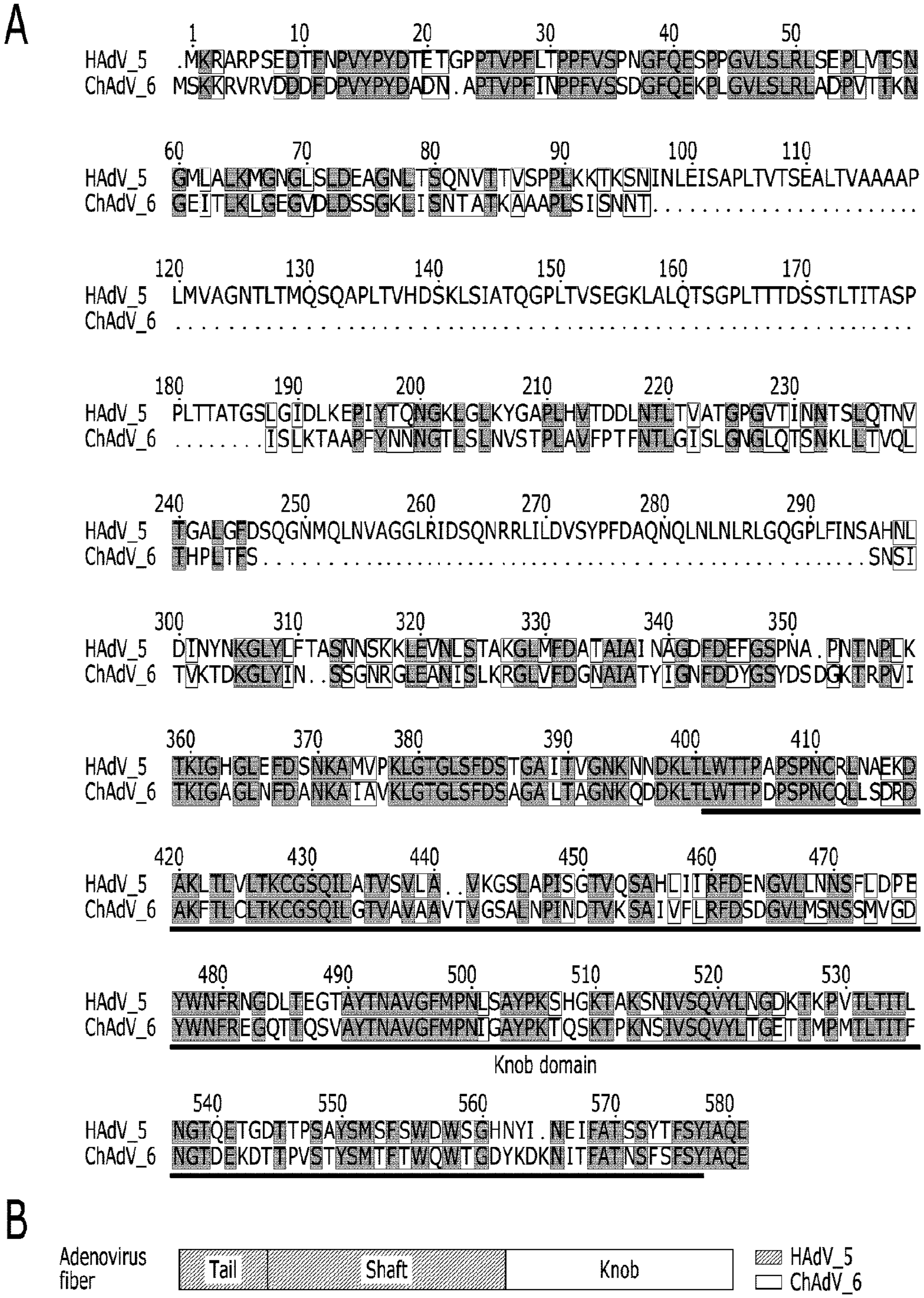

【Fig. 2】
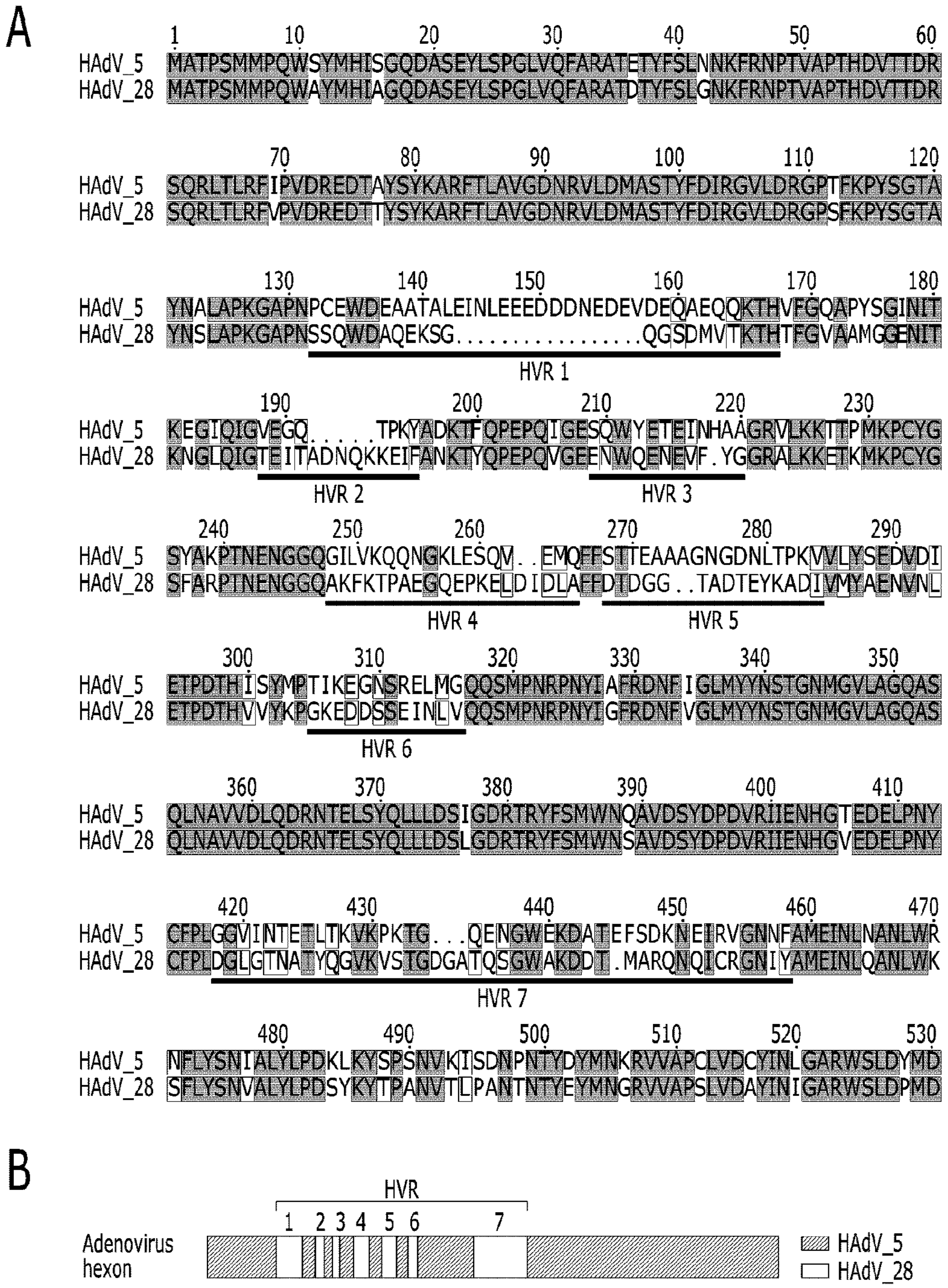

【Fig. 3】
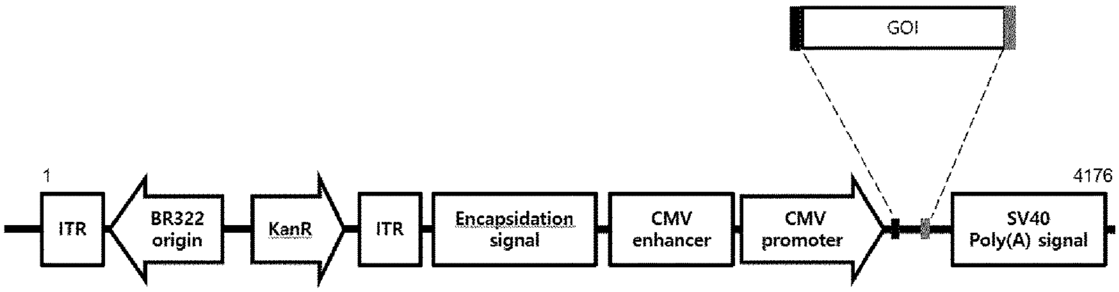
【Fig. 4】
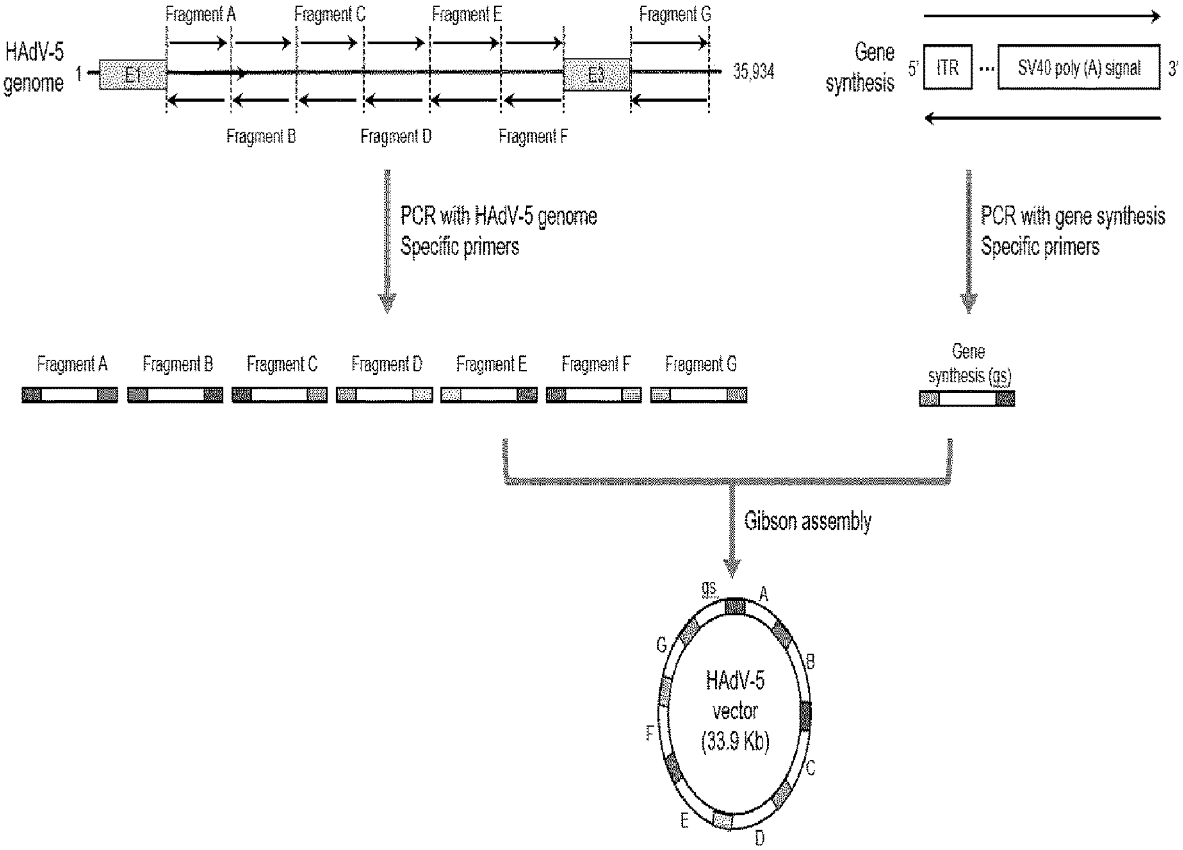

【Fig. 5】
A
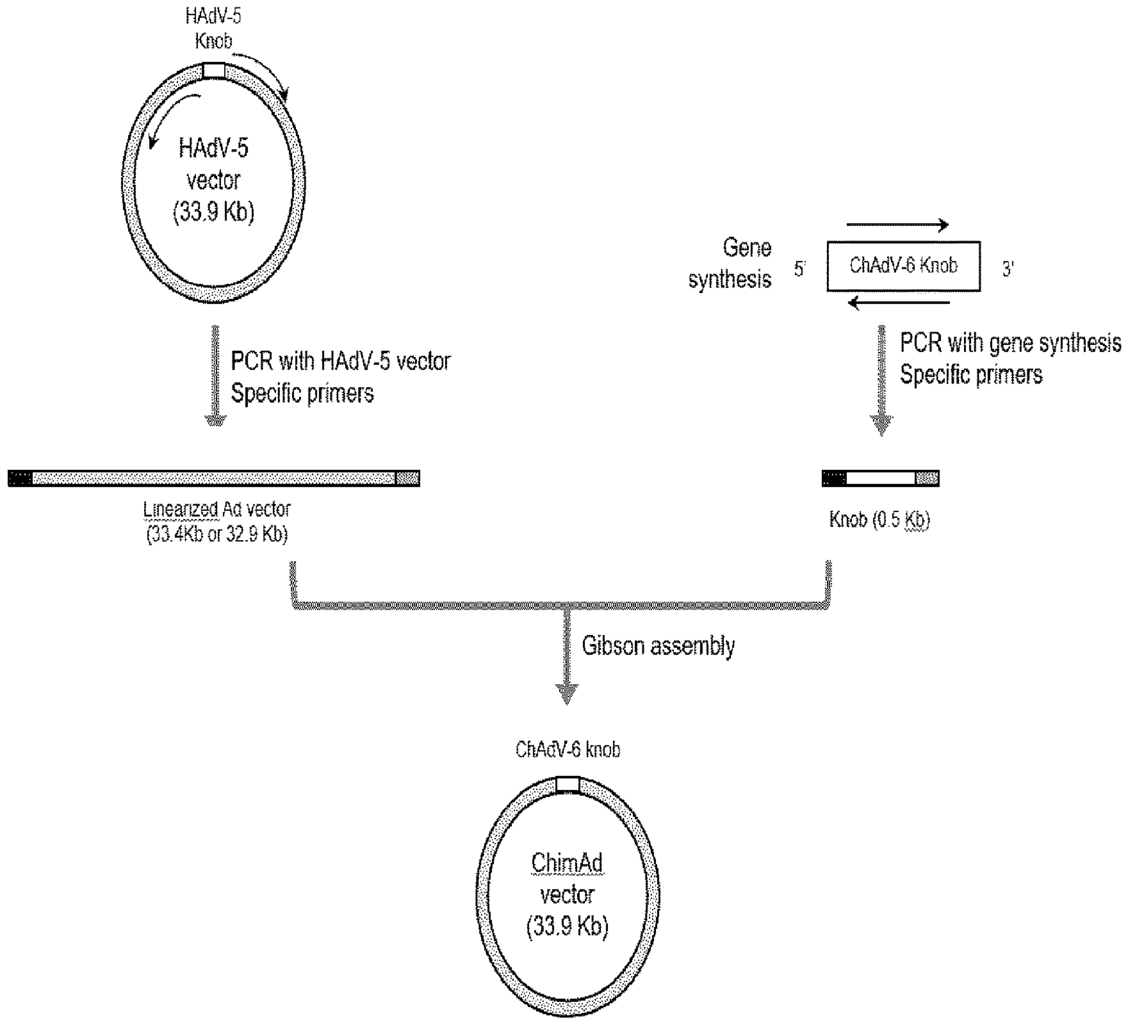

【Fig. 6】
B
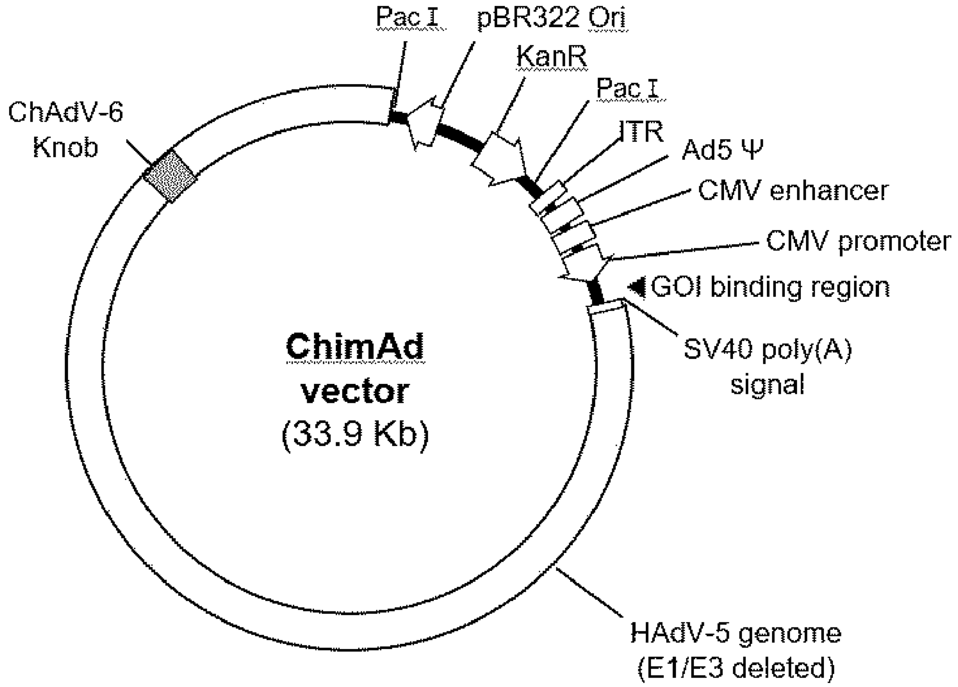

【Fig. 7】
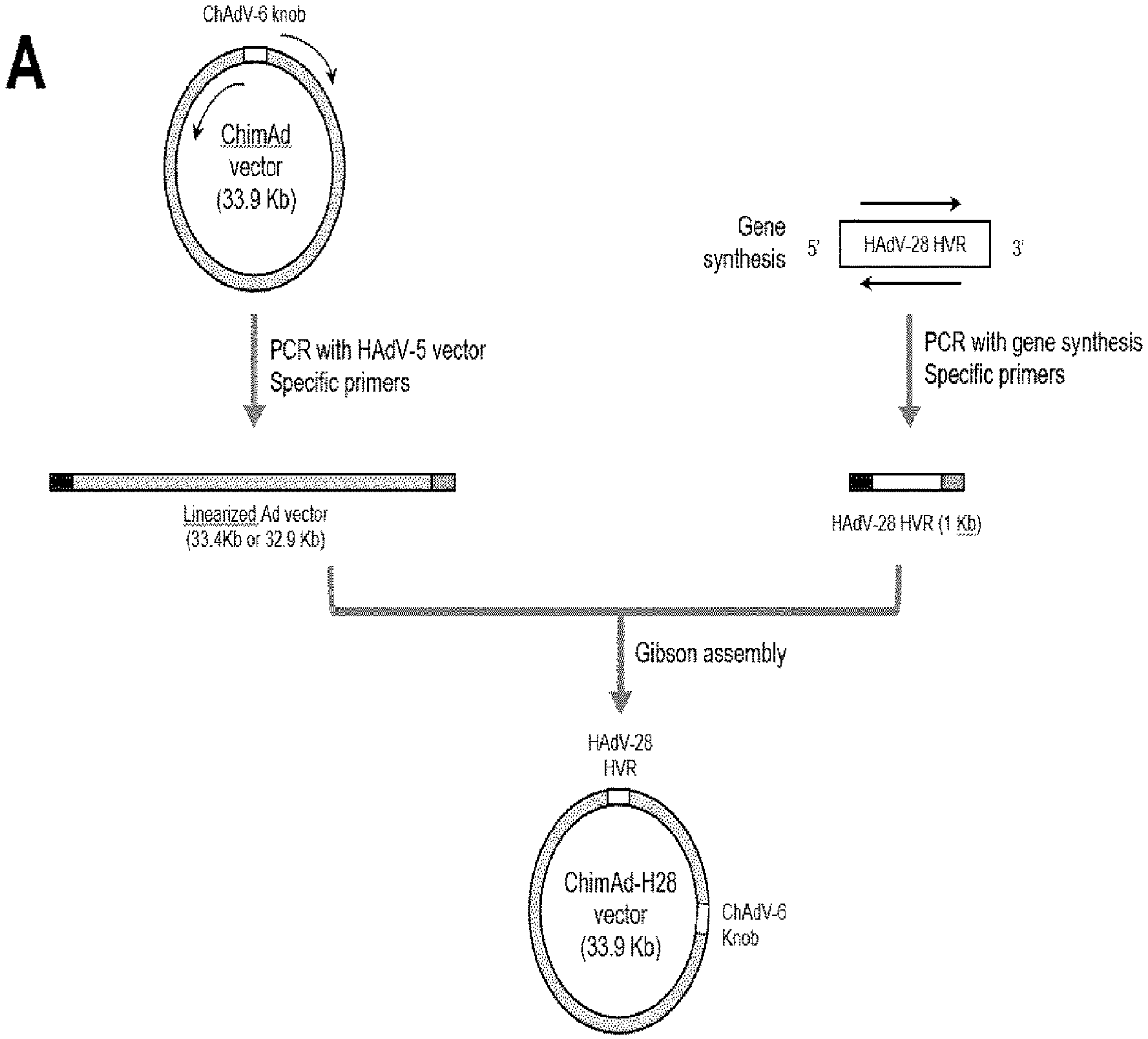

【Fig. 8】
B
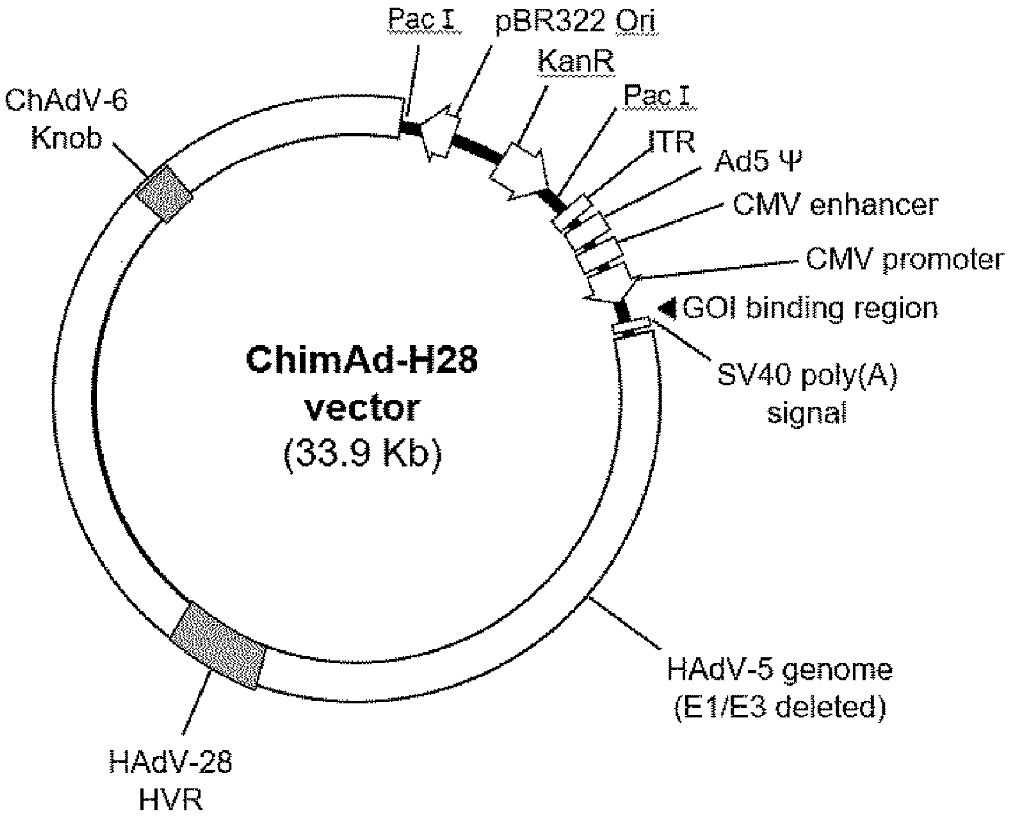

【Fig. 9】
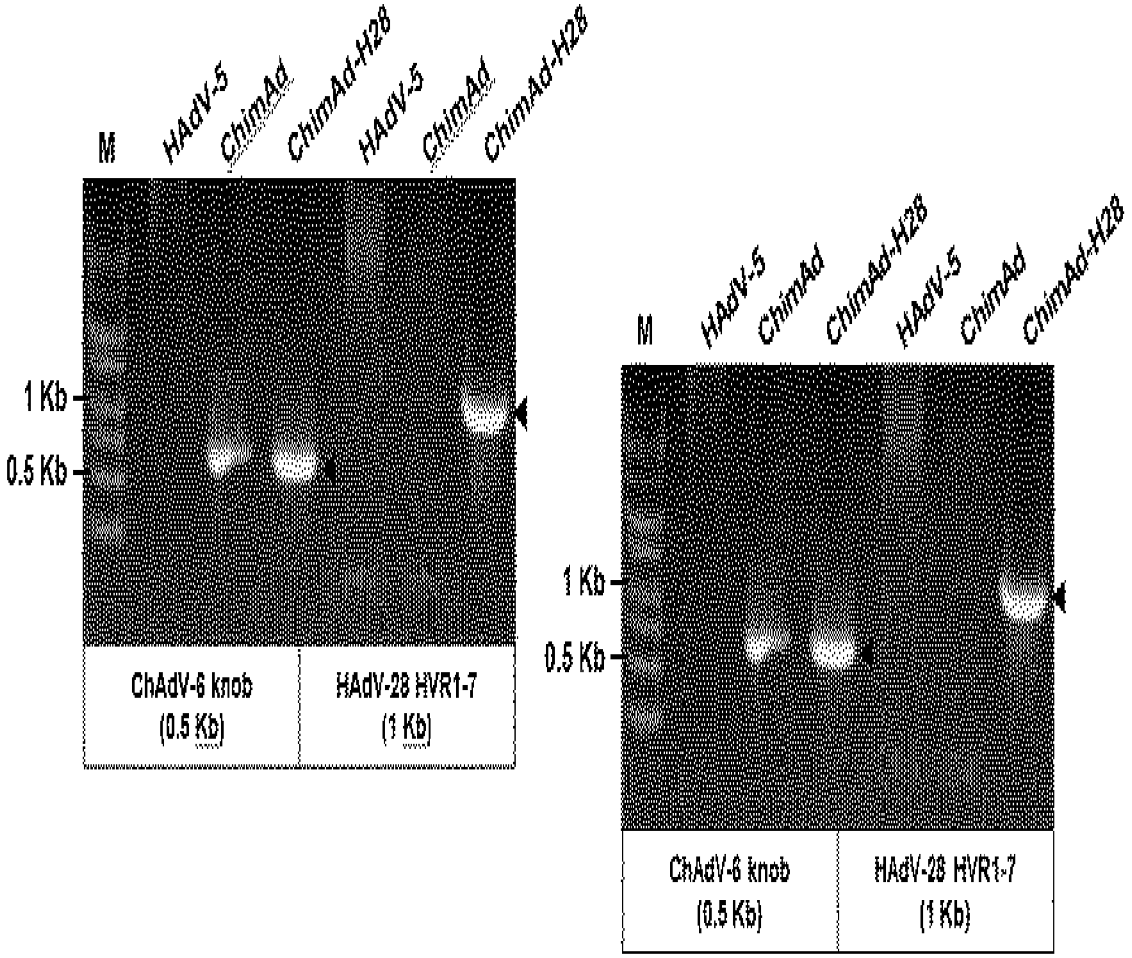

【Fig. 10】
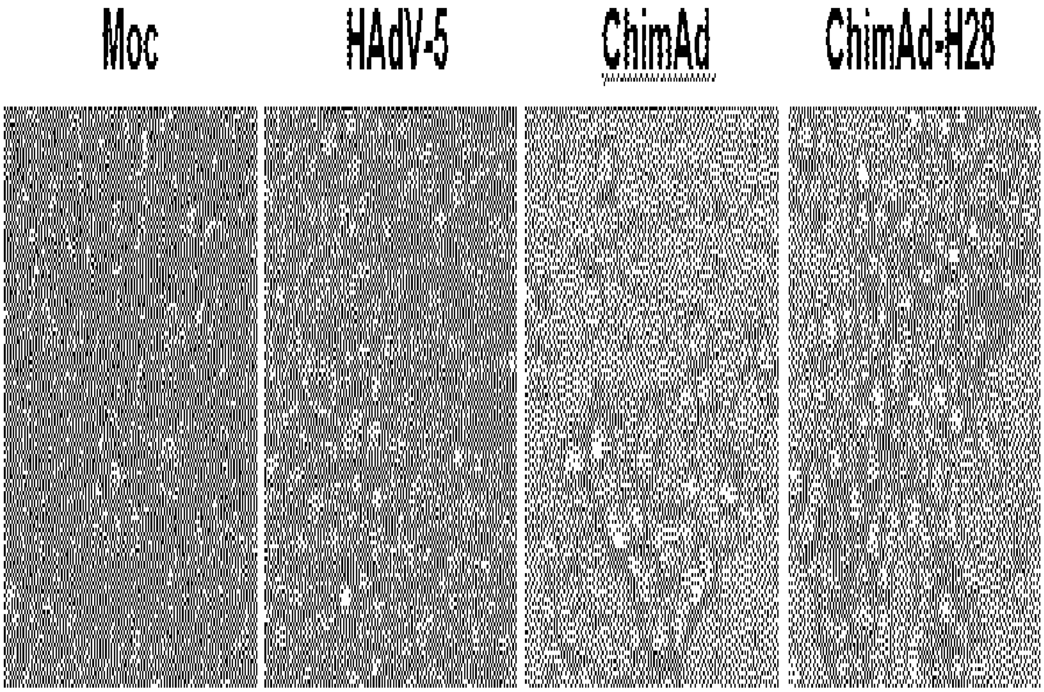

【Fig. 11】
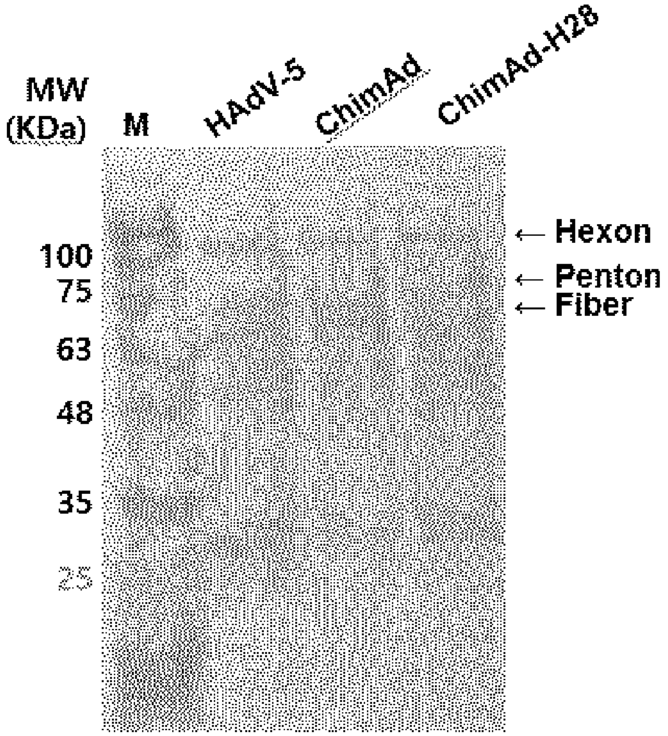

【Fig. 12】
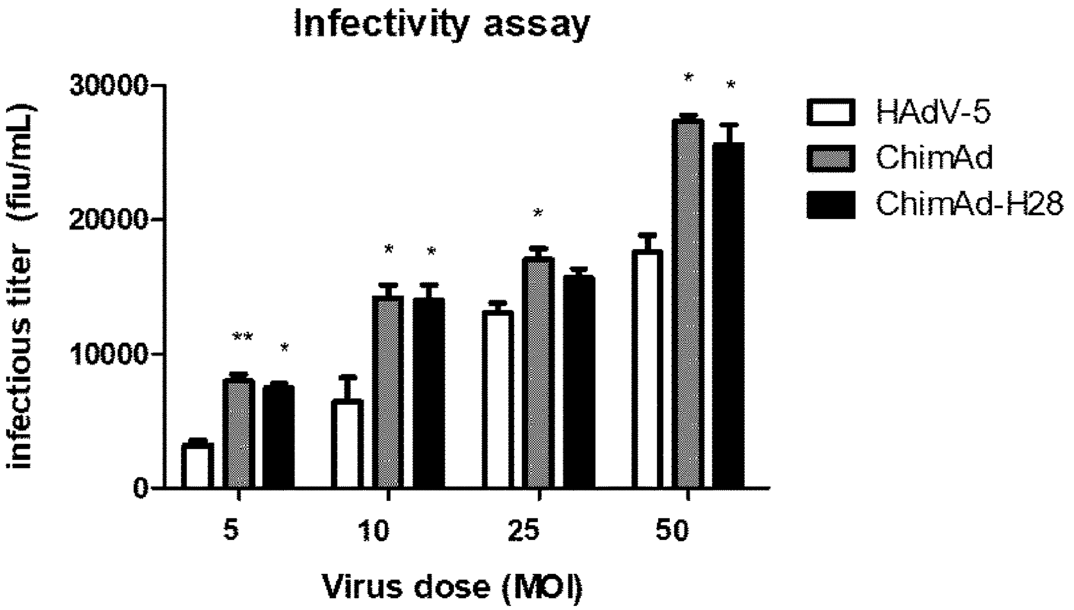
【Fig. 13】
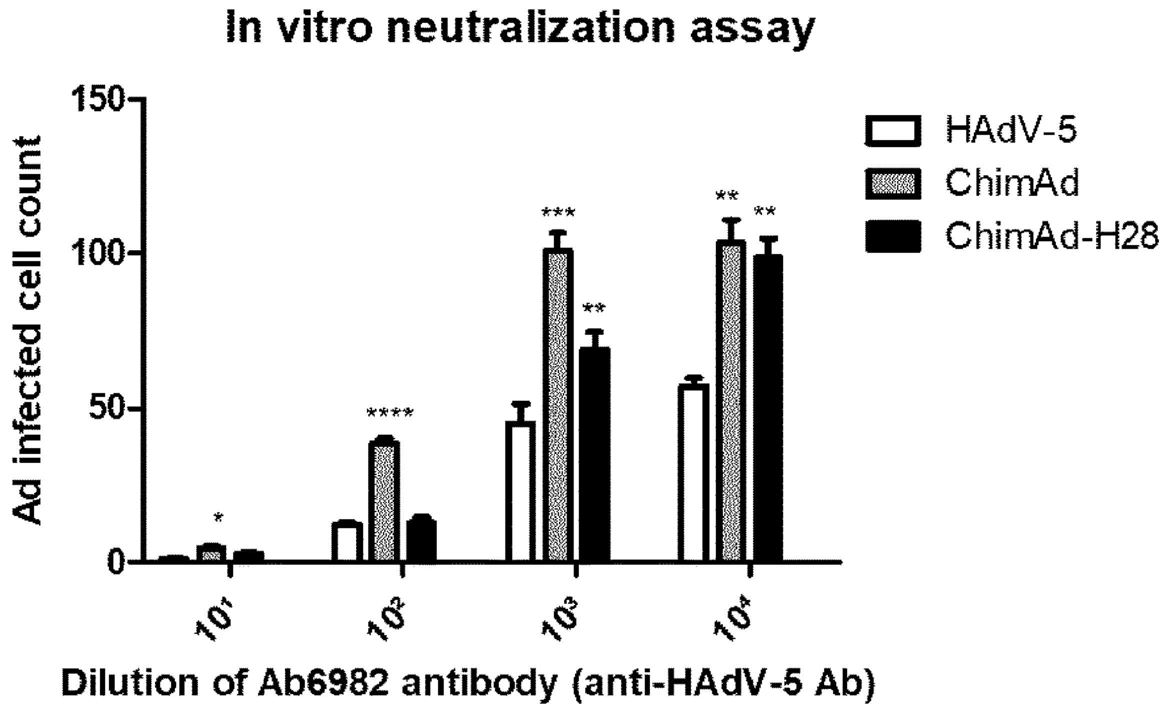

【Fig. 14】
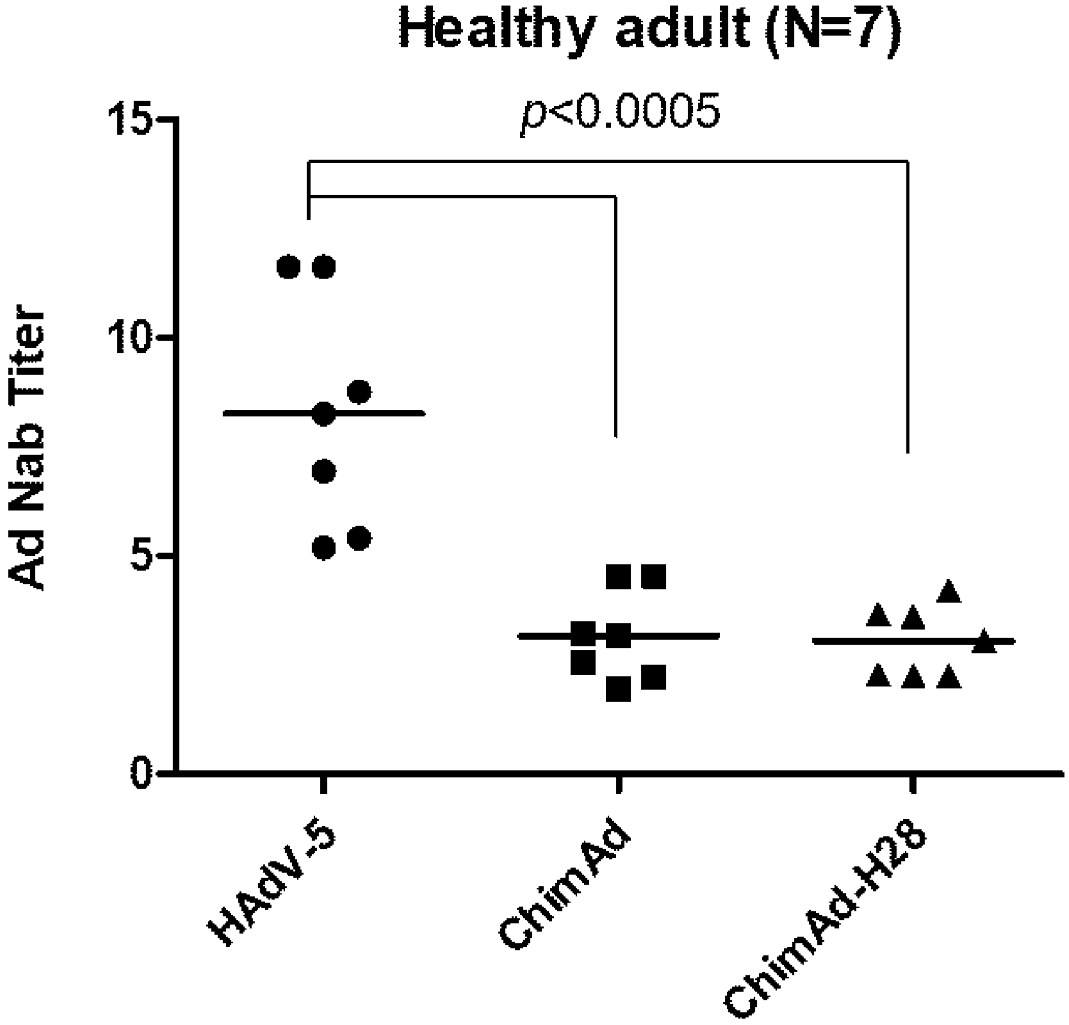

【Fig. 15】
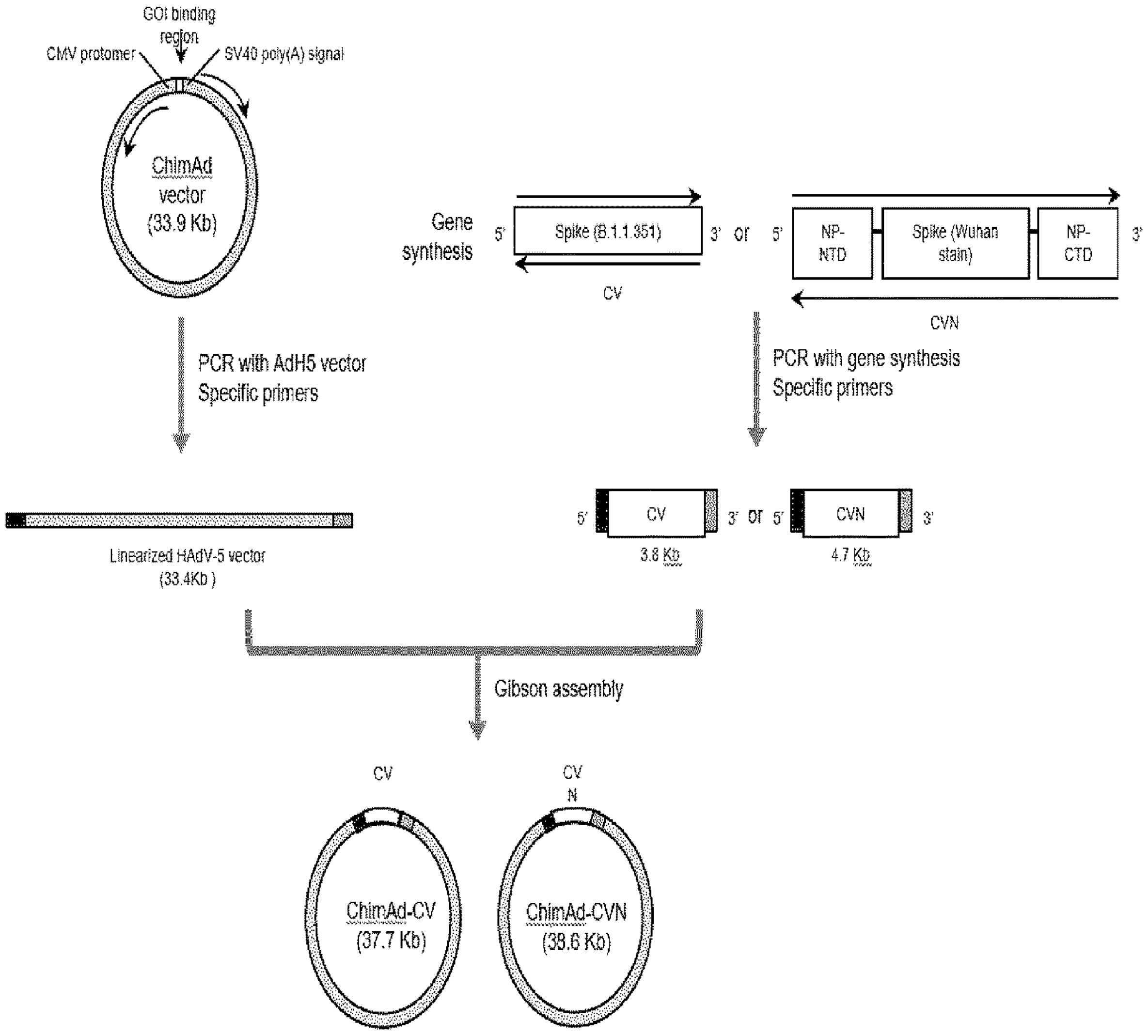

【Fig. 16】
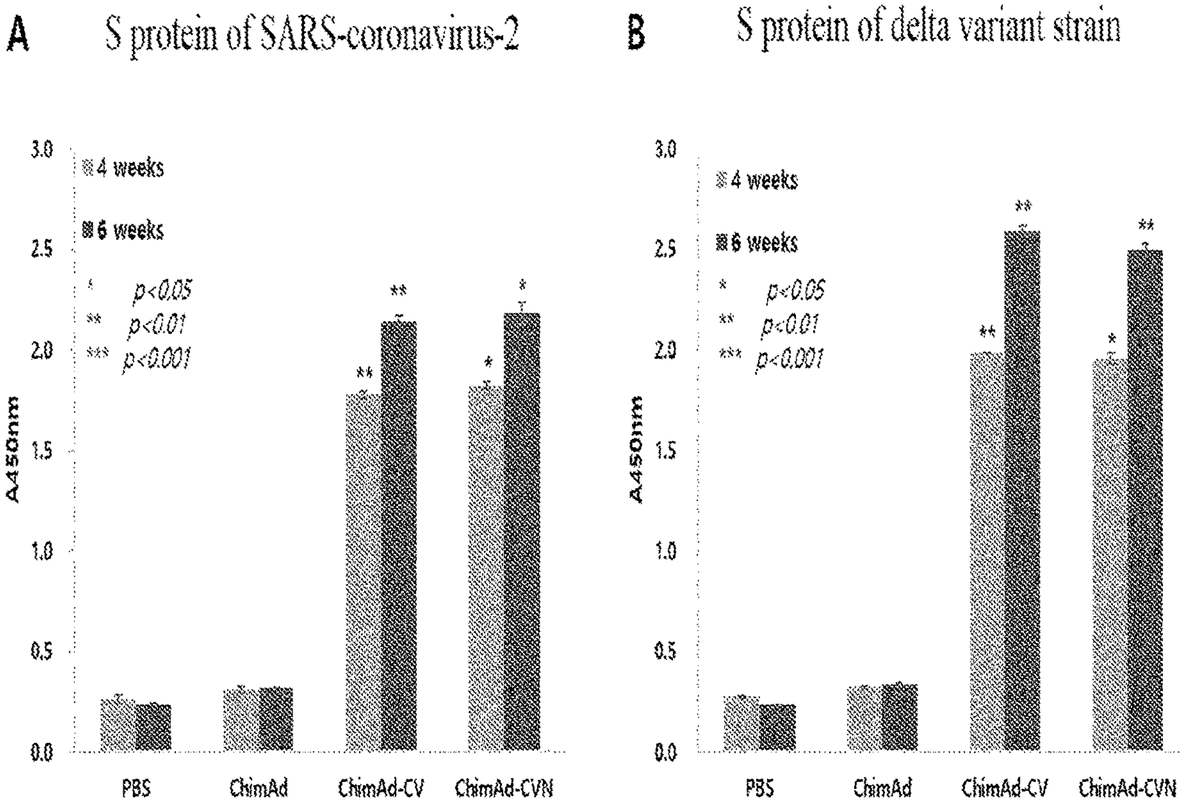

【Fig. 17】
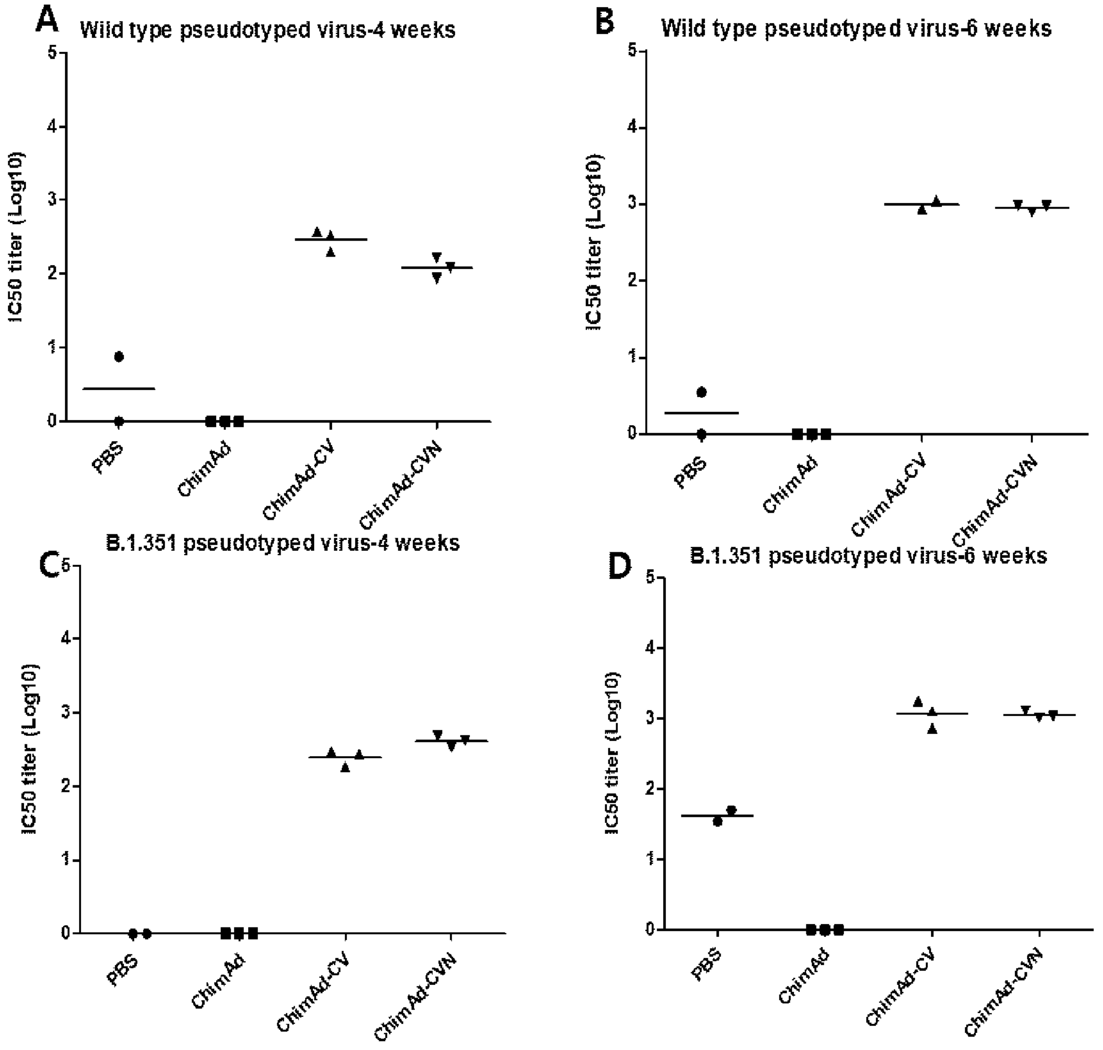

【Fig. 18】
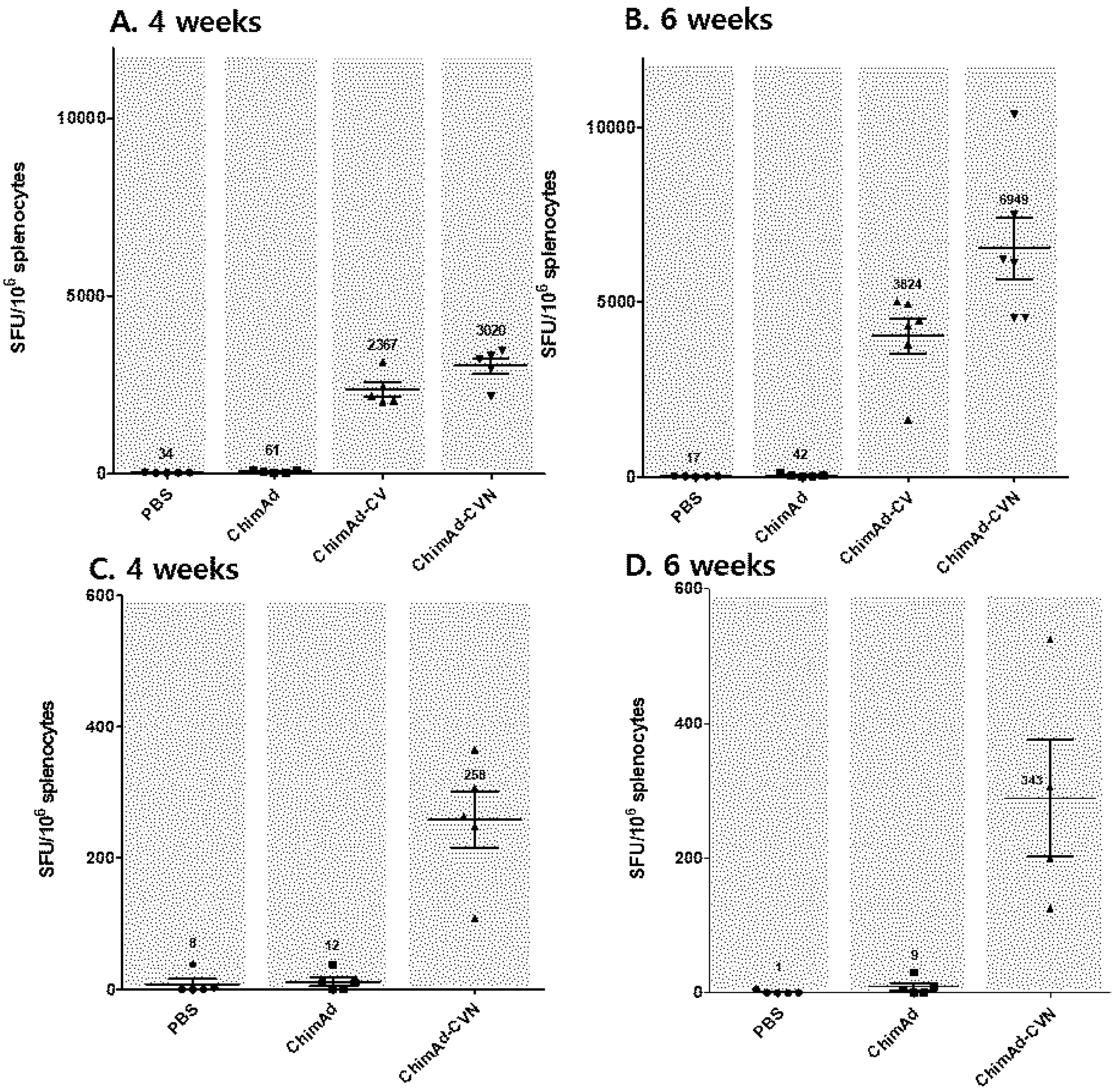

【Fig. 19】
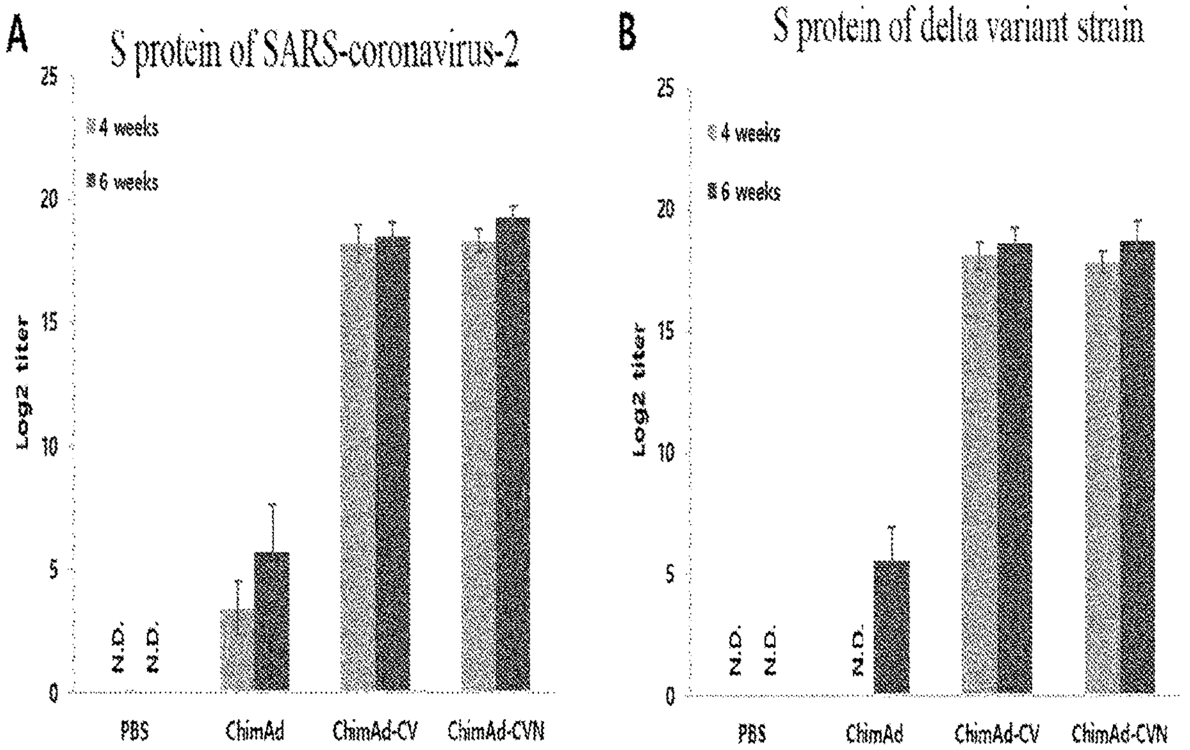

【Fig. 20】
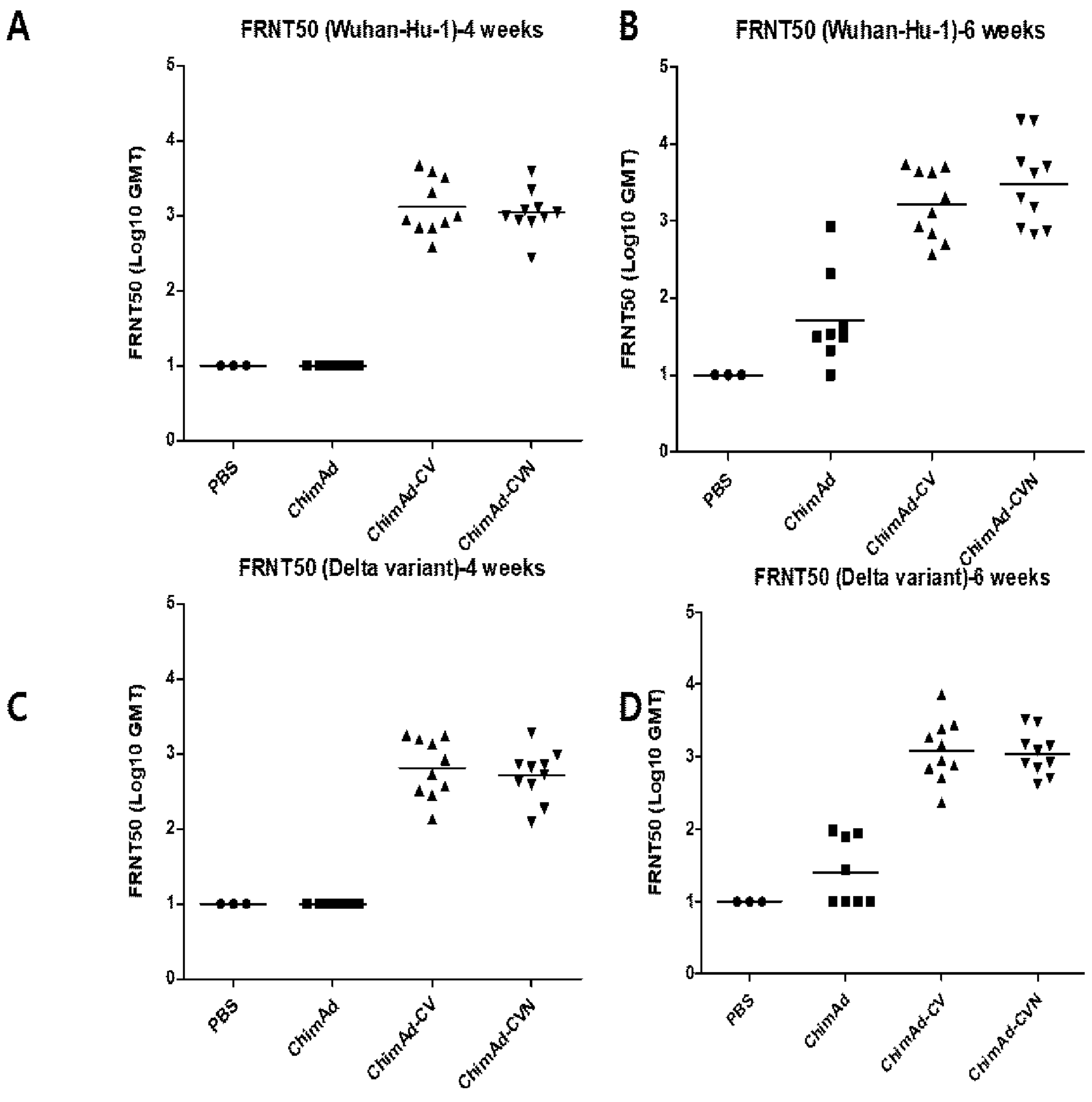

【Fig. 21】
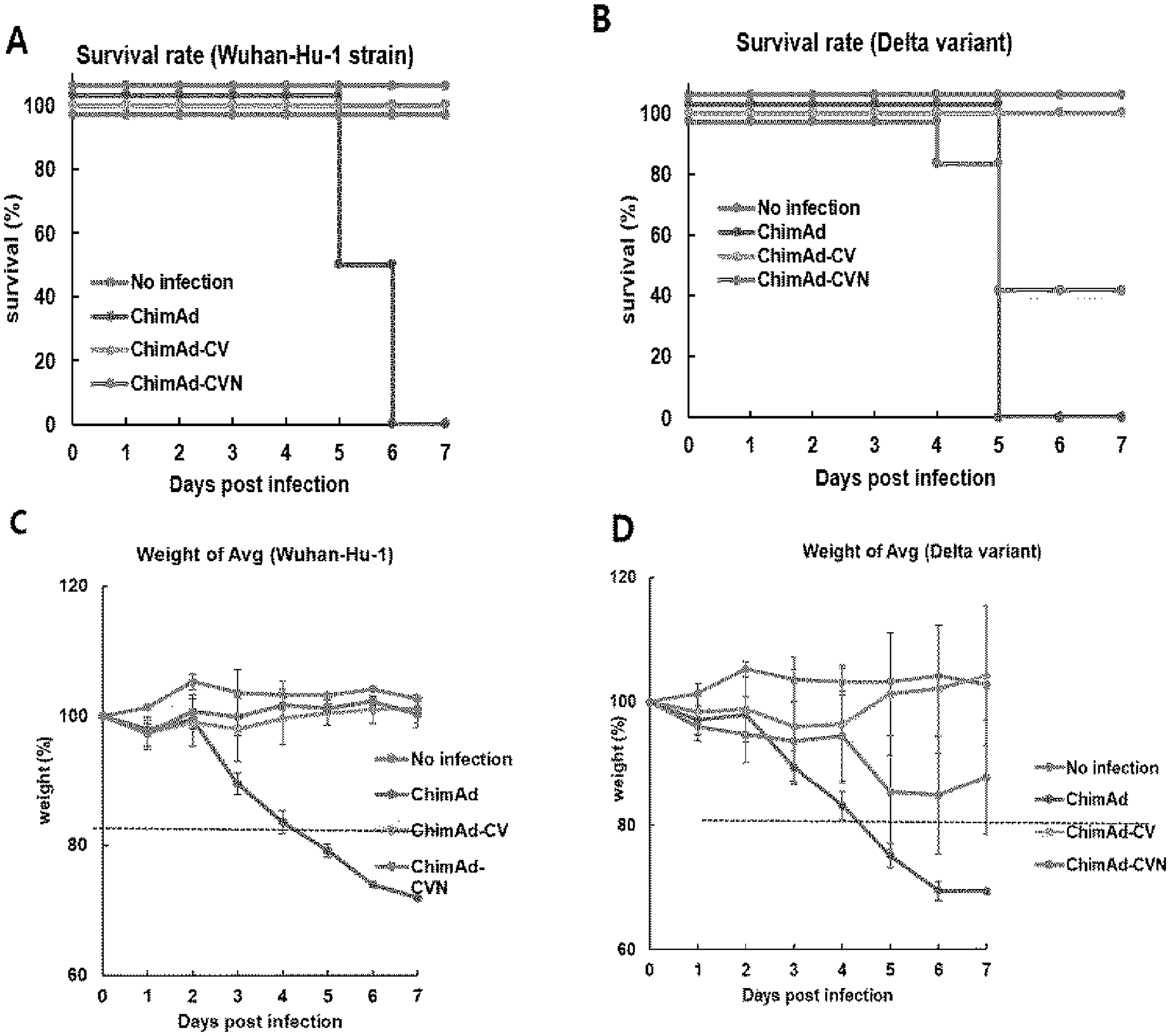

【Fig. 22】
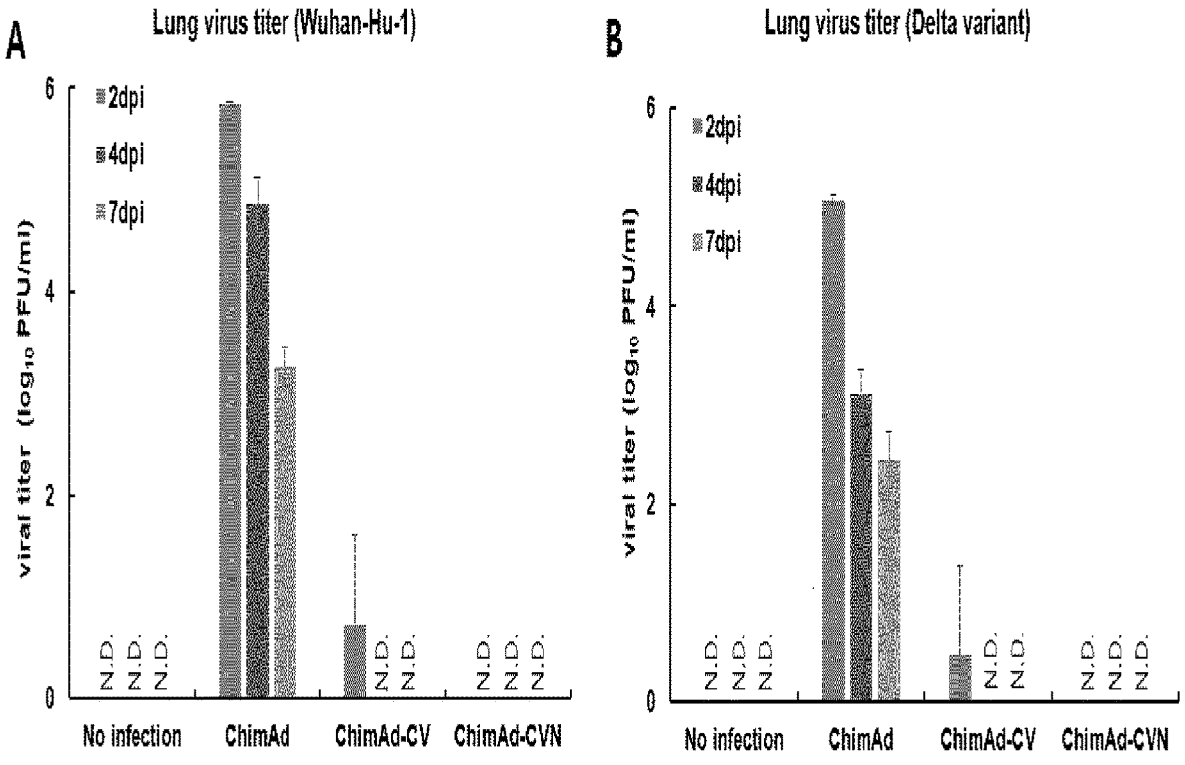

【Fig. 23】
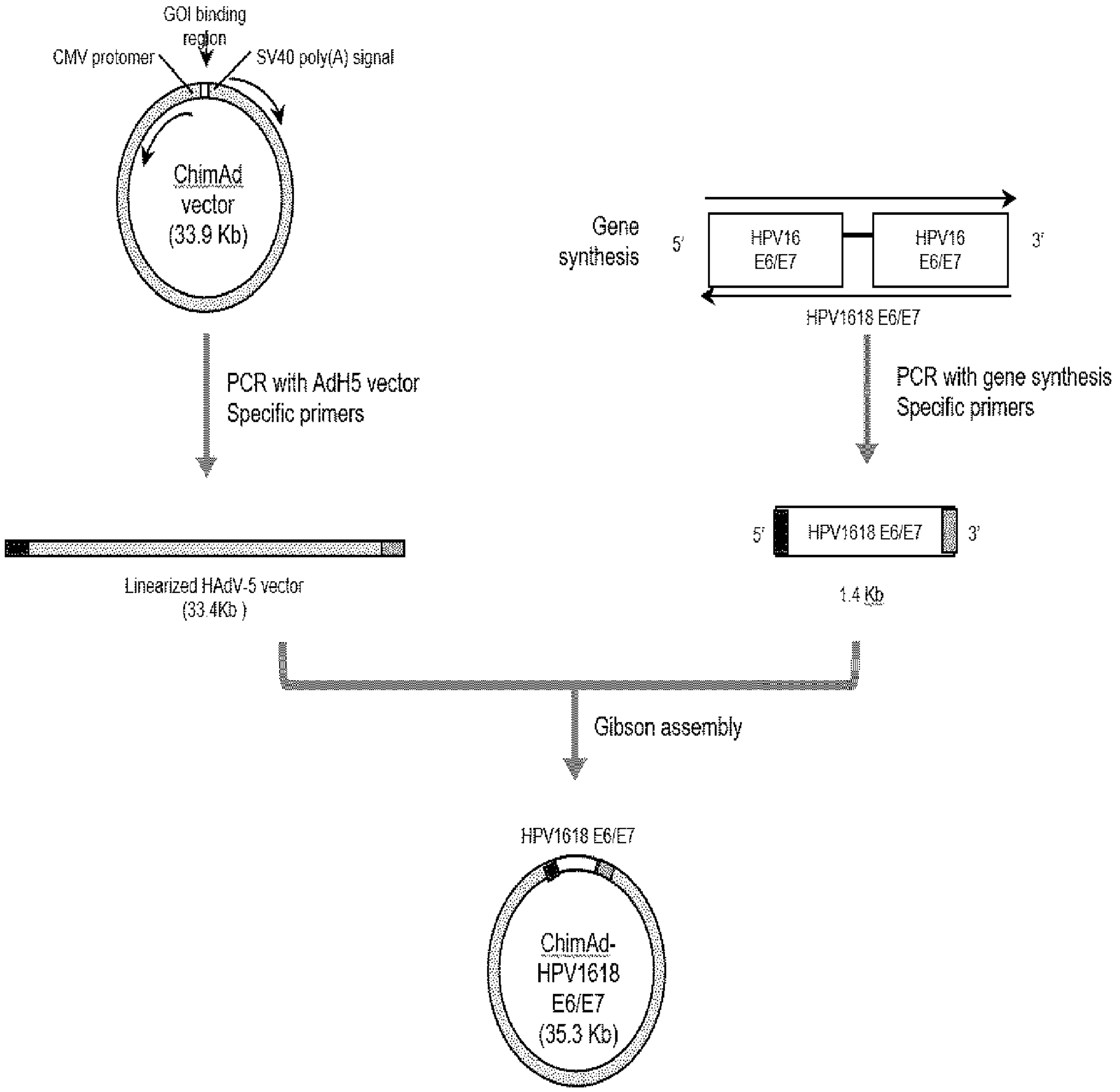

【Fig. 24】
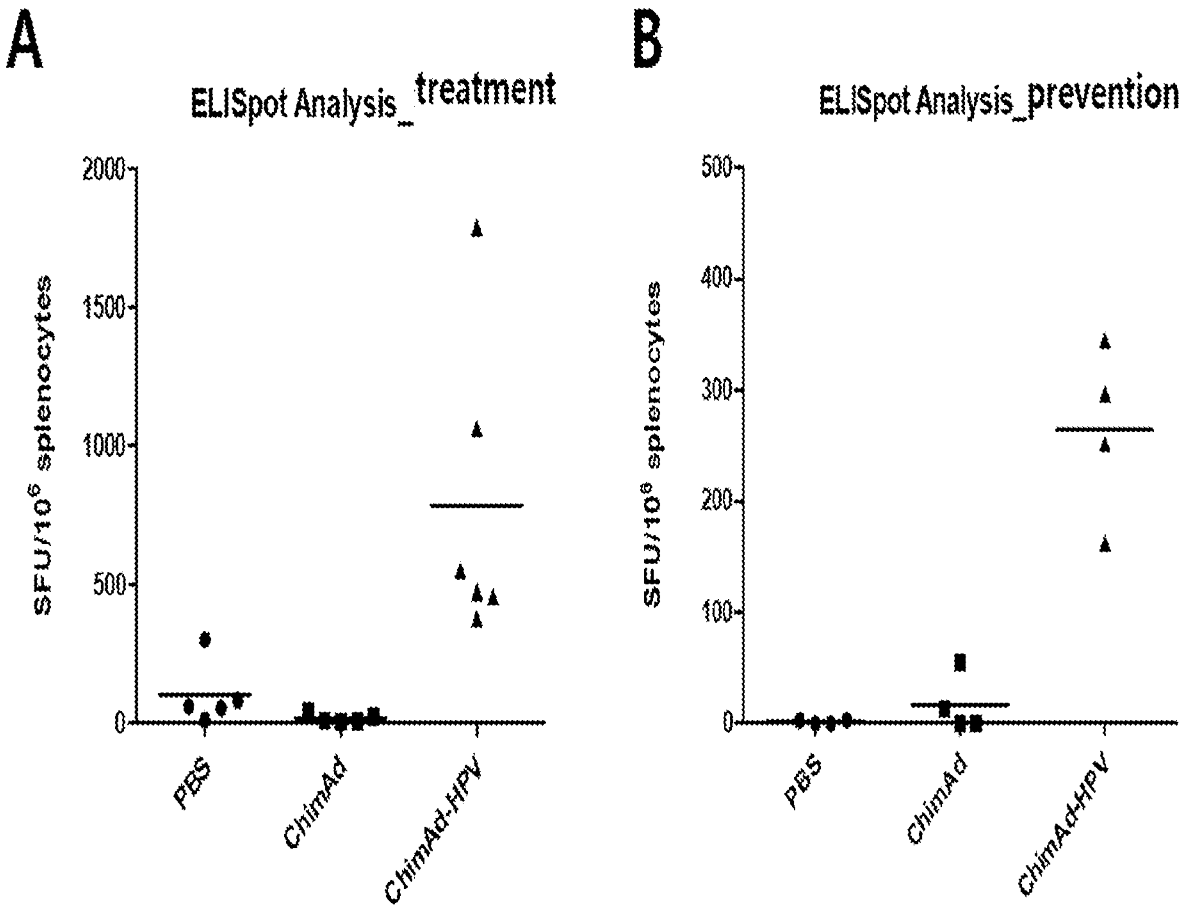

【Fig. 25】
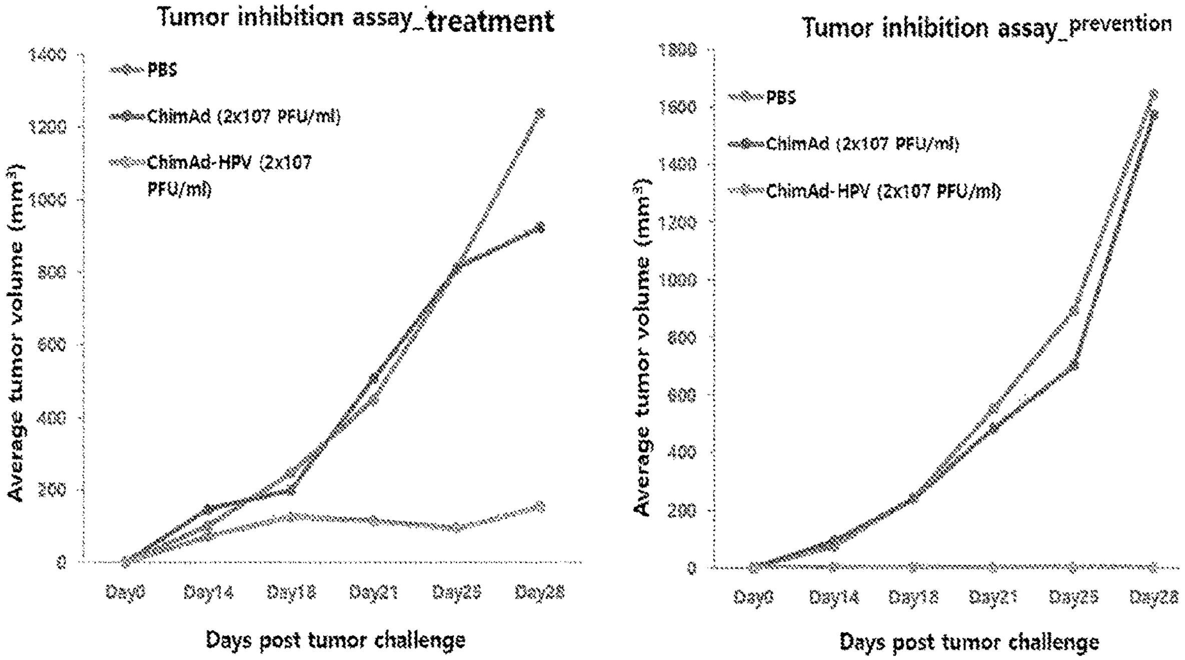

SEQUENCE LISTING

```
<160> NUMBER OF SEQ ID NOS: 62

<210> SEQ ID NO 1
<211> LENGTH: 173
<212> TYPE: PRT
<213> ORGANISM: Artificial Sequence
```

<220> FEATURE:
<223> OTHER INFORMATION: Chimpanzee adenovirus serotype 6 Fiber knob domain a.a sequence(synthesized ChAdV-6 knob a.a sequences are underlined)

<400> SEQUENCE: 1

Pro Asp Pro Ser Pro Asn Cys Gln Leu Leu Ser Asp Arg Asp Ala Lys
1 5 10 15

Phe Thr Leu Cys Leu Thr Lys Cys Gly Ser Gln Ile Leu Gly Thr Val
20 25 30

Ala Val Ala Ala Val Thr Val Gly Ser Ala Leu Asn Pro Ile Asn Asp
35 40 45

Thr Val Lys Ser Ala Ile Val Phe Leu Arg Phe Asp Ser Asp Gly Val
50 55 60

Leu Met Ser Asn Ser Ser Met Val Gly Asp Tyr Trp Asn Phe Arg Glu
65 70 75 80

Gly Gln Thr Thr Gln Ser Val Ala Tyr Thr Asn Ala Val Gly Phe Met
85 90 95

Pro Asn Ile Gly Ala Tyr Pro Lys Thr Gln Ser Lys Thr Pro Lys Asn
100 105 110

Ser Ile Val Ser Gln Val Tyr Leu Thr Gly Glu Thr Thr Met Pro Met
115 120 125

Thr Leu Thr Ile Thr Phe Asn Gly Thr Asp Glu Lys Asp Thr Thr Pro
130 135 140

Val Ser Thr Tyr Ser Met Thr Phe Thr Trp Gln Trp Thr Gly Asp Tyr
145 150 155 160

Lys Asp Lys Asn Ile Thr Phe Ala Thr Asn Ser Phe Ser
165 170

<210> SEQ ID NO 2
<211> LENGTH: 519
<212> TYPE: DNA
<213> ORGANISM: Artificial Sequence
<220> FEATURE:
<223> OTHER INFORMATION: Chimpanzee adenovirus serotype 6/Pan6/Sad23 Fiber knob domain nucleotide sequence

<400> SEQUENCE: 2
cctgacccaa gccctaattg tcaattactt tcagacagag atgccaaatt tactctctgt 60
cttacaaaat gcggtagtca aatactaggc actgtggcag tggcggctgt tactgtagga 120
tcagcactaa atccaattaa tgacacagtc aaaagcgcca tagttttcct tagatttgat 180
tccgatggtg tactcatgtc aaactcatca atggtaggtg attactggaa ctttagggag 240
ggacagacca ctcaaagtgt agcctataca aatgctgtgg gattcatgcc aaatataggt 300
gcatatccaa aaacccaaag taaaacacct aaaaatagca tagtcagtca ggtatattta 360
actggagaaa ctactatgcc aatgacacta accataactt tcaatggcac tgatgaaaaa 420
gacacaaccc cagttagcac ctactctatg acttttacat ggcagtggac tggagactat 480
aaggacaaaa atattacctt tgctaccaac tcattctct 519

<210> SEQ ID NO 3
<211> LENGTH: 318
<212> TYPE: PRT
<213> ORGANISM: Artificial Sequence
<220> FEATURE:
<223> OTHER INFORMATION: Chimeric hexon HVR 1 to 7 region a.a sequence (HAdV-5 hexon + HAdV-28 HVR 1-7 region)

<400> SEQUENCE: 3

```
Ser Ser Gln Trp Asp Ala Gln Glu Lys Ser Gly Gln Gly Ser Asp Met
1               5                   10                  15

Val Thr Lys Thr His Thr Phe Gly Gln Ala Pro Tyr Ser Gly Ile Asn
            20                  25                  30

Ile Thr Lys Glu Gly Ile Gln Ile Gly Thr Glu Ile Thr Ala Asp Asn
        35                  40                  45

Gln Lys Lys Glu Ile Phe Ala Asp Lys Thr Phe Gln Pro Glu Pro Gln
    50                  55                  60

Ile Gly Glu Glu Asn Trp Gln Glu Asn Glu Val Phe Tyr Gly Gly Arg
65                  70                  75                  80

Val Leu Lys Lys Thr Thr Pro Met Lys Pro Cys Tyr Gly Ser Tyr Ala
                85                  90                  95

Lys Pro Thr Asn Glu Asn Gly Gly Gln Ala Lys Phe Lys Thr Pro Ala
            100                 105                 110

Glu Gly Gln Glu Pro Lys Glu Leu Asp Ile Asp Leu Ala Phe Phe Asp
        115                 120                 125

Thr Asp Gly Gly Thr Ala Asp Thr Glu Tyr Lys Ala Asp Ile Val Leu
    130                 135                 140

Tyr Ser Glu Asp Val Asp Ile Glu Thr Pro Asp Thr His Ile Ser Tyr
145                 150                 155                 160

Met Pro Gly Lys Glu Asp Asp Ser Ser Glu Ile Asn Leu Val Gln Gln
                165                 170                 175

Ser Met Pro Asn Arg Pro Asn Tyr Ile Ala Phe Arg Asp Asn Phe Ile
            180                 185                 190

Gly Leu Met Tyr Tyr Asn Ser Thr Gly Asn Met Gly Val Leu Ala Gly
        195                 200                 205

Gln Ala Ser Gln Leu Asn Ala Val Val Asp Leu Gln Asp Arg Asn Thr
    210                 215                 220

Glu Leu Ser Tyr Gln Leu Leu Leu Asp Ser Ile Gly Asp Arg Thr Arg
225                 230                 235                 240

Tyr Phe Ser Met Trp Asn Gln Ala Val Asp Ser Tyr Asp Pro Asp Val
                245                 250                 255

Arg Ile Ile Glu Asn His Gly Thr Glu Asp Glu Leu Pro Asn Tyr Cys
            260                 265                 270

Phe Pro Leu Asp Gly Leu Gly Thr Asn Ala Thr Tyr Gln Gly Val Lys
        275                 280                 285

Val Ser Thr Gly Asp Gly Ala Thr Gln Ser Gly Trp Ala Lys Asp Asp
    290                 295                 300

Thr Met Ala Arg Gln Asn Gln Ile Cys Arg Gly Asn Ile Tyr
305                 310                 315


<210> SEQ ID NO 4
<211> LENGTH: 954
<212> TYPE: DNA
<213> ORGANISM: Artificial Sequence
<220> FEATURE:
<223> OTHER INFORMATION: Chimeric hexon HVR 1 to 7 region nucleotide
      sequence (HAdV-5 hexon + HAdV-28 HVR 1-7 region)

<400> SEQUENCE: 4

tccagtcagt gggatgcgca agaaaaaagt ggacaaggaa gtgacatggt tactaaaact      60

cacacatttg ggcaggcgcc ttattctggt ataaatatta caaaggaggg tattcaaata     120

ggtactgaaa ttaccgccga caatcaaaag aaagaaattt ttgccgataa aacatttcaa     180

cctgaacctc aaataggaga agagaactgg caagaaaatg aagtcttcta tggcgggaga     240
```

```
gtcctaaaaa agactacccc aatgaaacca tgttacggtt catatgcaaa acccacaaat    300

gaaaatggag ggcaagcaaa attcaaaaca cctgctgaag gacaggaacc taaagaactt    360

gacattgacc ttgctttttt cgacactgac ggcggaacag ctgacactga atataaagca    420

gatattgtat tgtacagtga agatgtagat atagaaaccc cagacactca tatttcttac    480

atgcccggca aggaagatga cagttcagaa atcaatctag ttcaacaatc tatgcccaac    540

aggcctaatt acattgcttt tagggacaat tttattggtc taatgtatta caacagcacg    600

ggtaatatgg gtgttctggc gggccaagca tcgcagttga atgctgttgt agatttgcaa    660

gacagaaaca cagagctttc ataccagctt ttgcttgatt ccattggtga tagaaccagg    720

tacttttcta tgtggaatca ggctgttgac agctatgatc cagatgttag aattattgaa    780

aatcatggaa ctgaagatga acttccaaat tactgctttc cactggacgg attgggaact    840

aatgctacct atcaaggtgt aaaagtatca actggagatg gtgctacgca aagcggatgg    900

gcaaaagacg acacaatggc caggcaaaac caaatatgca ggggtaacat ctac          954
```

<210> SEQ ID NO 5
<211> LENGTH: 1731
<212> TYPE: DNA
<213> ORGANISM: Artificial Sequence
<220> FEATURE:
<223> OTHER INFORMATION: Chimeric fiber gene sequence (HAdV-5 tail, shift domain + ChAdV-6 knob domain)

<400> SEQUENCE: 5

```
atgaagcgcg caagaccgtc tgaagatacc ttcaaccccg tgtatccata tgacacggaa     60

accggtcctc caactgtgcc ttttcttact cctccctttg tatcccccaa tgggtttcaa    120

gagagtcccc ctggggtact ctctttgcgc ctatccgaac ctctagttac ctccaatggc    180

atgcttgcgc tcaaaatggg caacggcctc tctctggacg aggccggcaa ccttacctcc    240

caaaatgtaa ccactgtgag cccacctctc aaaaaaacca agtcaaacat aaacctggaa    300

atatctgcac ccctcacagt tacctcagaa gccctaactg tggctgccgc cgcacctcta    360

atggtcgcgg gcaacacact caccatgcaa tcacaggccc cgctaaccgt gcacgactcc    420

aaacttagca ttgccaccca aggacccctc acagtgtcag aaggaaagct agccctgcaa    480

acatcaggcc ccctcaccac caccgatagc agtaccctta ctatcactgc ctcacccccct    540

ctaactactg ccactggtag cttgggcatt gacttgaaag agcccattta tacacaaaat    600

ggaaaactag gactaaagta cggggctcct ttgcatgtaa cagacgacct aaacactttg    660

accgtagcaa ctggtccagg tgtgactatt aataatactt ccttgcaaac taaagttact    720

ggagccttgg gttttgattc acaaggcaat atgcaactta atgtagcagg aggactaagg    780

attgattctc aaaacagacg ccttatactt gatgttagtt atccgtttga tgctcaaaac    840

caactaaatc taagactagg acagggccct ctttttataa actcagccca caacttggat    900

attaactaca acaaaggcct ttacttgttt acagcttcaa acaattccaa aaagcttgag    960

gttaacctaa gcactgccaa ggggttgatg tttgacgcta cagccatagc cattaatgca   1020

ggagatgggc ttgaatttgg ttcacctaat gcaccaaaca caaatcccct caaaacaaaa   1080

attggccatg gcctagaatt tgattcaaac aaggctatgg ttcctaaact aggaactggc   1140

cttagttttg acagcacagg tgccattaca gtaggaaaca aaaataatga taagctaact   1200

ttgtggacca cacctgaccc aagccctaat tgtcaattac tttcagacag agatgccaaa   1260

tttactctct gtcttacaaa atgcggtagt caaatactag gcactgtggc agtggcggct   1320
```

```
gttactgtag gatcagcact aaatccaatt aatgacacag tcaaaagcgc catagttttc   1380

cttagatttg attccgatgg tgtactcatg tcaaactcat caatggtagg tgattactgg   1440

aactttaggg agggacagac cactcaaagt gtagcctata caaatgctgt gggattcatg   1500

ccaaatatag gtgcatatcc aaaaacccaa agtaaaacac ctaaaaatag catagtcagt   1560

caggtatatt taactggaga aactactatg ccaatgacac taaccataac tttcaatggc   1620

actgatgaaa aagacacaac cccagttagc acctactcta tgacttttac atggcagtgg   1680

actggagact ataaggacaa aaatattacc tttgctacca actcattctc t            1731
```

<210> SEQ ID NO 6
<211> LENGTH: 2832
<212> TYPE: DNA
<213> ORGANISM: Artificial Sequence
<220> FEATURE:
<223> OTHER INFORMATION: Chimeric hexon gene sequence (HAdV-5 hexon + HAdV-28 HVR 1-7region)

<400> SEQUENCE: 6

```
atggctaccc cttcgatgat gccgcagtgg tcttacatgc acatctcggg ccaggacgcc     60

tcggagtacc tgagccccgg gctggtgcag tttgcccgcg ccaccgagac gtacttcagc    120

ctgaataaca agtttagaaa ccccacggtg gcgcctacgc acgacgtgac cacagaccgg    180

tcccagcgtt tgacgctgcg gttcatccct gtggaccgtg aggatactgc gtactcgtac    240

aaggcgcggt tcaccctagc tgtgggtgat aaccgtgtgc tggacatggc ttccacgtac    300

tttgacatcc gcggcgtgct ggacaggggc cctactttta agccctactc tggcactgcc    360

tacaacgccc tggctcccaa gggtgcccca aattccagtc agtgggatgc gcaagaaaaa    420

agtggacaag gaagtgacat ggttactaaa actcacacat ttgggcaggc gccttattct    480

ggtataaata ttacaaagga gggtattcaa ataggtactg aaattaccgc cgacaatcaa    540

aagaaagaaa tttttgccga taaaacattt caacctgaac ctcaaatagg agaagagaac    600

tggcaagaaa atgaagtctt ctatggcggg agagtcctaa aaaagactac cccaatgaaa    660

ccatgttacg gttcatatgc aaaacccaca aatgaaaatg gagggcaagc aaaattcaaa    720

acacctgctg aaggacagga acctaaagaa cttgacattg accttgcttt tttcgacact    780

gacggcggaa cagctgacac tgaatataaa gcagatattg tattgtacag tgaagatgta    840

gatatagaaa ccccagacac tcatatttct tacatgcccg gcaaggaaga tgacagttca    900

gaaatcaatc tagttcaaca atctatgccc aacaggccta attacattgc ttttagggac    960

aattttattg gtctaatgta ttacaacagc acgggtaata tgggtgttct ggcgggccaa   1020

gcatcgcagt tgaatgctgt tgtagatttg caagacagaa acacagagct ttcataccag   1080

cttttgcttg attccattgg tgatagaacc aggtactttt ctatgtggaa tcaggctgtt   1140

gacagctatg atccagatgt tagaattatt gaaaatcatg gaactgaaga tgaacttcca   1200

aattactgct ttccactgga cggattggga actaatgcta cctatcaagg tgtaaaagta   1260

tcaactggag atggtgctac gcaaagcgga tgggcaaaag acgacacaat ggccaggcaa   1320

aaccaaatat gcaggggtaa catctacgcc atggaaatca atctaaatgc caacctgtgg   1380

agaaatttcc tgtactccaa catagcgctg tatttgcccg acaagctaaa gtacagtcct   1440

tccaacgtaa aaatttctga taacccaaac acctacgact acatgaacaa gcgagtggtg   1500

gctcccgggc tagtggactg ctacattaac cttggagcac gctggtccct tgactatatg   1560

gacaacgtca acccatttaa ccaccaccgc aatgctggcc tgcgctaccg ctcaatgttg   1620
```

```
ctgggcaatg gtcgctatgt gcccttccac atccaggtgc ctcagaagtt ctttgccatt   1680

aaaaacctcc ttctcctgcc gggctcatac acctacgagt ggaacttcag gaaggatgtt   1740

aacatggttc tgcagagctc cctaggaaat gacctaaggg ttgacggagc cagcattaag   1800

tttgatagca tttgccttta cgccaccttc ttccccatgg cccacaacac cgcctccacg   1860

cttgaggcca tgcttagaaa cgacaccaac gaccagtcct ttaacgacta tctctccgcc   1920

gccaacatgc tctaccctat acccgccaac gctaccaacg tgcccatatc catcccctcc   1980

cgcaactggg cggctttccg cggctgggcc ttcacgcgcc ttaagactaa ggaaacccca   2040

tcactgggct cgggctacga cccttattac acctactctg gctctatacc ctacctagat   2100

ggaacctttt acctcaacca cacctttaag aaggtggcca ttacctttga ctcttctgtc   2160

agctggcctg gcaatgaccg cctgcttacc cccaacgagt ttgaaattaa gcgctcagtt   2220

gacggggagg gttacaacgt tgcccagtgt aacatgacca aagactggtt cctggtacaa   2280

atgctagcta actataacat tggctaccag ggcttctata tcccagagag ctacaaggac   2340

cgcatgtact ccttctttag aaacttccag cccatgagcc gtcaggtggt ggatgatact   2400

aaatacaagg actaccaaca ggtgggcatc ctacaccaac acaacaactc tggatttgtt   2460

ggctaccttg cccccaccat gcgcgaagga caggcctacc ctgctaactt cccctatccg   2520

cttataggca agaccgcagt tgacagcatt acccagaaaa agtttctttg cgatcgcacc   2580

ctttggcgca tcccattctc cagtaacttt atgtccatgg gcgcactcac agacctgggc   2640

caaaaccttc tctacgccaa ctccgcccac gcgctagaca tgacttttga ggtggatccc   2700

atggacgagc ccacccttct ttatgttttg tttgaagtct ttgacgtggt ccgtgtgcac   2760

cagccgcacc gcggcgtcat cgaaaccgtg tacctgcgca cgcccttctc ggccggcaac   2820

gccacaacat aa                                                       2832


<210> SEQ ID NO 7
<211> LENGTH: 1270
<212> TYPE: PRT
<213> ORGANISM: Artificial Sequence
<220> FEATURE:
<223> OTHER INFORMATION: SARS-CoV-2_B.1.351(beta) spike modified amino
      acid sequence

<400> SEQUENCE: 7

Met Phe Val Phe Leu Val Leu Leu Pro Leu Val Ser Ser Gln Cys Val
1               5                   10                  15

Asn Phe Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Ala
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
```

```
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Gly Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu His Ile Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270

Leu Leu Lys Tyr Asn Glu Asn Gly Thr Ile Thr Asp Ala Val Asp Cys
        275                 280                 285

Ala Leu Asp Pro Leu Ser Glu Thr Lys Cys Thr Leu Lys Ser Phe Thr
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Asn Ile Ala
                405                 410                 415

Asp Tyr Asn Tyr Lys Leu Pro Asp Asp Phe Thr Gly Cys Val Ile Ala
            420                 425                 430

Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Lys Gly Phe Asn Cys Tyr Phe Pro Leu Gln Ser Tyr Gly Phe Gln Pro
                485                 490                 495

Thr Tyr Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe Asn Phe Asn Gly Leu Thr
    530                 535                 540

Gly Thr Gly Val Leu Thr Glu Ser Asn Lys Lys Phe Leu Pro Phe Gln
545                 550                 555                 560
```

```
Gln Phe Gly Arg Asp Ile Ala Asp Thr Thr Asp Ala Val Arg Asp Pro
                565                 570                 575

Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
        595                 600                 605

Tyr Gln Gly Val Asn Cys Thr Glu Val Pro Val Ala Ile His Ala Asp
    610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
                645                 650                 655

Tyr Glu Cys Asp Ile Pro Ile Gly Ala Gly Ile Cys Ala Ser Tyr Gln
            660                 665                 670

Thr Gln Thr Asn Ser Pro Gln Gln Ala Gln Ser Val Ala Ser Gln Ser
        675                 680                 685

Ile Ile Ala Tyr Thr Met Ser Leu Gly Val Glu Asn Ser Val Ala Tyr
    690                 695                 700

Ser Asn Asn Ser Ile Ala Ile Pro Thr Asn Phe Thr Ile Ser Val Thr
705                 710                 715                 720

Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
            740                 745                 750

Tyr Gly Ser Phe Cys Thr Gln Leu Asn Arg Ala Leu Thr Gly Ile Ala
        755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Phe Ile Glu
                805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Ala Ala Leu Gln Ile Pro Phe Ala
                885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Ala Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975
```

```
Ile Leu Ser Arg Leu Asp Pro Pro Glu Ala Glu Val Gln Ile Asp Arg
            980                 985                 990

Leu Ile Thr Gly Arg Leu Gln Ser  Leu Gln Thr Tyr Val  Thr Gln Gln
        995                 1000                 1005

Leu Ile  Arg Ala Ala Glu Ile  Arg Ala Ser Ala Asn  Leu Ala Ala
    1010                 1015                 1020

Thr Lys  Met Ser Glu Cys Val  Leu Gly Gln Ser Lys  Arg Val Asp
    1025                 1030                 1035

Phe Cys  Gly Lys Gly Tyr His  Leu Met Ser Phe Pro  Gln Ser Ala
    1040                 1045                 1050

Pro His  Gly Val Val Phe Leu  His Val Thr Tyr Val  Pro Ala Gln
    1055                 1060                 1065

Glu Lys  Asn Phe Thr Thr Ala  Pro Ala Ile Cys His  Asp Gly Lys
    1070                 1075                 1080

Ala His  Phe Pro Arg Glu Gly  Val Phe Val Ser Asn  Gly Thr His
    1085                 1090                 1095

Trp Phe  Val Thr Gln Arg Asn  Phe Tyr Glu Pro Gln  Ile Ile Thr
    1100                 1105                 1110

Thr Asp  Asn Thr Phe Val Ser  Gly Asn Cys Asp Val  Val Ile Gly
    1115                 1120                 1125

Ile Val  Asn Asn Thr Val Tyr  Asp Pro Leu Gln Pro  Glu Leu Asp
    1130                 1135                 1140

Ser Phe  Lys Glu Glu Leu Asp  Lys Tyr Phe Lys Asn  His Thr Ser
    1145                 1150                 1155

Pro Asp  Val Asp Leu Gly Asp  Ile Ser Gly Ile Asn  Ala Ser Val
    1160                 1165                 1170

Val Asn  Ile Gln Lys Glu Ile  Asp Arg Leu Asn Glu  Val Ala Lys
    1175                 1180                 1185

Asn Leu  Asn Glu Ser Leu Ile  Asp Leu Gln Glu Leu  Gly Lys Tyr
    1190                 1195                 1200

Glu Gln  Tyr Ile Lys Trp Pro  Trp Tyr Ile Trp Leu  Gly Phe Ile
    1205                 1210                 1215

Ala Gly  Leu Ile Ala Ile Val  Met Val Thr Ile Met  Leu Cys Cys
    1220                 1225                 1230

Met Thr  Ser Cys Cys Ser Cys  Leu Lys Gly Cys Cys  Ser Cys Gly
    1235                 1240                 1245

Ser Cys  Cys Lys Phe Asp Glu  Asp Asp Ser Glu Pro  Val Leu Lys
    1250                 1255                 1260

Gly Val  Lys Leu His Tyr Thr
    1265                 1270


<210> SEQ ID NO 8
<211> LENGTH: 3813
<212> TYPE: DNA
<213> ORGANISM: Artificial Sequence
<220> FEATURE:
<223> OTHER INFORMATION: SARS-CoV-2_B.1.351(beta) spike modified nucleic
      acid sequence

<400> SEQUENCE: 8

atgtttgtgt ttctggtgct gctgcctctg gtgagcagcc agtgcgtgaa cttcaccacc     60

agaacccagc tgcctcctgc ctacaccaac agctttacca gaggcgtgta ttaccccgac    120

aaagtgttta gatcctccgt gctgcacagc acccaggacc tgtttctgcc ctttttcagc    180

aacgtgacct ggttccatgc catccacgtg agcggcacca acggcaccaa gagattcgcc    240
```

-continued

```
aatcccgtgc tgccttttaa tgacggcgtg tactttgcca gcaccgagaa gagcaatatc    300
atcagaggct ggatcttcgg caccaccctg gatagcaaga cccagagcct gctgatcgtg    360
aataatgcca ccaatgtggt gatcaaagtg tgcgagttcc agttttgtaa cgaccccttt    420
ctgggcgtgt attaccacaa gaacaacaaa agctggatgg agagcgaatt cagagtgtac    480
agcagcgcca ataactgcac ctttgagtac gtgagccagc cctttctgat ggacctggag    540
ggcaagcagg gcaacttcaa gaacctgaga gagttcgtgt ttaaaaatat cgacggctac    600
ttcaagatct acagcaagca tacacccatc aacctggtga gaggcctgcc ccagggcttc    660
agcgccctgg agcccctggt ggacctgccc atcggcatca acattacccg gtttcagacc    720
ctgcacagaa gctatctgac ccccggcgac agcagcagcg gctggaccgc cggagccgcc    780
gcctattatg tgggctacct gcagcccaga accttcctgc tgaaatacaa cgagaacggc    840
accatcaccg acgccgtgga ctgcgccctg gacccccctga gcgagaccaa gtgtaccctg    900
aagagcttta ccgtggagaa gggcatctac cagaccagca actttagagt gcagcccacc    960
gagagcatcg tgagatttcc caacatcacc aacctgtgcc ccttcgggga ggtgtttaat   1020
gccaccagat tcgccagcgt gtacgcctgg aatagaaaaa gaatcagcaa ctgcgtggcc   1080
gactacagcg tgctgtacaa ctctgccagc ttttccacct ttaagtgcta cggcgtgagc   1140
ccaaccaaac tgaacgacct gtgcttcacc aacgtgtacg ccgacagctt cgtgatcaga   1200
ggcgacgagg tgagacagat cgcccccggc cagaccggca atatcgccga ttacaactac   1260
aagctgcccg acgactttac cggctgcgtg atcgcctgga acagcaacaa cctggacagc   1320
aaggtgggcg gcaactacaa ctacctgtac agactgttta gaaagagcaa cctgaagccc   1380
tttgagagag acatcagcac cgagatctac caggccggca gcacccccctg caacggcgtg   1440
aaaggcttta attgttactt cccactgcag tcctacggct tccagcctac ctacggcgtg   1500
ggatatcagc cctatagagt ggtggtgctg tccttcgagc tgctgcacgc cccgccacc   1560
gtgtgcggcc caaagaagag caccaacctg gtgaagaaca agtgcgtgaa cttcaacttc   1620
aacggcctga ccggcaccgg cgtgctgacc gagtccaaca agaaatttct gcccttccag   1680
cagttcggaa gagacattgc cgataccacc gacgccgtga gagaccccca gaccctggag   1740
atcctggaca tcacccccctg tagcttcggc ggcgtgtccg tgatcacccc aggcaccaac   1800
acctccaacc aggtggccgt gctgtaccag ggcgtgaact gtaccgaggt gcctgtggcc   1860
atccacgccg atcagctgac cccaacctgg agagtgtact ccaccggctc caacgtgttc   1920
cagaccagag ccggctgtct gatcggcgcc gagcacgtga acaactccta cgagtgcgac   1980
atccctatcg gcgccggcat ctgcgccagc taccagaccc agaccaatag cccccagcag   2040
gcccagtccg tggccagcca gtccatcatt gcctacacca tgtccctggg cgtggagaac   2100
agcgtggcct actccaacaa cagcatcgcc atccccacca atttcaccat cagcgtgacc   2160
accgaaatcc tgccagtgag catgaccaaa acctccgtgg attgcaccat gtacatctgc   2220
ggagactcca ccgagtgctc caacctgctg ctgcagtacg gctccttttg cacccagctg   2280
aacagagccc tgaccggaat cgccgtggag caggataaaa acacccagga agtgttcgcc   2340
caggtgaaac agatctacaa gacccccccc atcaaagatt ttggaggctt taattttagc   2400
cagatcctgc ctgatccctc caaacccagc aagagatcct ttatcgagga tctgctgttc   2460
aacaaagtga cactggccga tgccggattt atcaaacagt acggagactg cctgggcgac   2520
atcgccgcca gagacctgat ctgcgcccag aagtttaacg gcctgaccgt gctgccaccc   2580
ctgctgaccg acgagatgat cgcccagtat acctccgccc tgctggccgg caccatcacc   2640
```

```
tccggctgga cctttggcgc cggagccgcc ctgcagatcc catttgccat gcagatggcc   2700

tacagattta atggaatcgg agtgacccag aacgtgctgt atgagaacca gaaactgatc   2760

gccaatcagt tcaacagcgc catcggcaag atccaggatt ctctgagctc caccgcctct   2820

gccctgggca agctgcagga cgtggtgaat cagaacgccc aggccctgaa caccctggtg   2880

aaacagctga gcagcaactt tggcgccatc agcagcgtgc tgaatgatat cctgagcaga   2940

ctggatcctc cagaggccga ggtgcagatc gacagactga tcacagggag actgcagagc   3000

ctgcagacct atgtgacaca gcagctgatc agagccgccg aaattagagc cagcgccaac   3060

ctggccgcca ccaaaatgag cgagtgtgtg ctgggacaga gcaaaagagt ggacttctgc   3120

ggcaaaggct accatctgat gagcttcccc cagagcgccc cccacggcgt ggtgttcctg   3180

catgtgacct acgtgcccgc ccaggaaaaa aattttacca ccgcccctgc catctgtcac   3240

gacggcaaag cccattttcc cagagagggc gtgtttgtga gcaacggcac ccactggttt   3300

gtgacccaga gaaactttta cgaaccccag atcatcacca cagataatac ctttgtgagc   3360

ggaaattgtg atgtggtgat cggcatcgtg aataataccg tgtatgatcc tctgcagcca   3420

gagctggaca gctttaagga ggagctggac aagtatttta aaaatcatac cagccccgac   3480

gtggatctgg gagatatcag cggaatcaac gcctccgtgg tgaatatcca gaaggagatc   3540

gacagactga acgaggtggc caaaaatctg aatgagtccc tgatcgacct gcaggagctg   3600

ggcaaatatg aacagtacat caagtggcca tggtacatct ggctggggtt tatcgccgga   3660

ctgatcgcca tcgtgatggt gaccatcatg ctgtgttgca tgaccagctg ttgtagctgt   3720

ctgaaaggct gttgtagctg cggcagctgc tgcaaatttg acgaggatga ttccgagcca   3780

gtgctgaagg gagtgaaact gcactatacc tga                                3813
```

```
<210> SEQ ID NO 9
<211> LENGTH: 138
<212> TYPE: PRT
<213> ORGANISM: Artificial Sequence
<220> FEATURE:
<223> OTHER INFORMATION: Sequence bound to the N-terminus of SARS-CoV-2-
      B.1.1.351 Spike protein

<400> SEQUENCE: 9

Met Gly Leu Pro Asn Asn Thr Ala Ser Trp Phe Thr Ala Leu Thr Gln
1               5                   10                  15

His Gly Lys Glu Asp Leu Lys Phe Pro Arg Gly Gln Gly Val Pro Ile
            20                  25                  30

Asn Thr Asn Ser Ser Pro Asp Asp Gln Ile Gly Tyr Tyr Arg Arg Ala
        35                  40                  45

Thr Arg Arg Ile Arg Gly Gly Asp Gly Lys Met Lys Asp Leu Ser Pro
    50                  55                  60

Arg Trp Tyr Phe Tyr Tyr Leu Gly Thr Gly Pro Glu Ala Gly Leu Pro
65                  70                  75                  80

Tyr Gly Ala Asn Lys Asp Gly Ile Ile Trp Val Ala Thr Glu Gly Ala
                85                  90                  95

Leu Asn Thr Pro Lys Asp His Ile Gly Thr Arg Asn Pro Ala Asn Asn
            100                 105                 110

Ala Ala Ile Val Leu Gln Leu Pro Gln Gly Thr Thr Leu Pro Lys Gly
        115                 120                 125

Phe Tyr Ala Glu Gly Ser Arg Gly Gly Ser
    130                 135
```

<210> SEQ ID NO 10
<211> LENGTH: 118
<212> TYPE: PRT
<213> ORGANISM: Artificial Sequence
<220> FEATURE:
<223> OTHER INFORMATION: Sequence bound to the C-terminus of SARS-CoV-2-B.1.1.351 Spike protein

<400> SEQUENCE: 10

```
Thr Lys Lys Ser Ala Ala Glu Ala Ser Lys Lys Pro Arg Gln Lys Arg
1               5                   10                  15

Thr Ala Thr Lys Ala Tyr Asn Val Thr Gln Ala Phe Gly Arg Arg Gly
            20                  25                  30

Pro Glu Gln Thr Gln Gly Asn Phe Gly Asp Gln Glu Leu Ile Arg Gln
        35                  40                  45

Gly Thr Asp Tyr Lys His Trp Pro Gln Ile Ala Gln Phe Ala Pro Ser
    50                  55                  60

Ala Ser Ala Phe Phe Gly Met Ser Arg Ile Gly Met Glu Val Thr Pro
65                  70                  75                  80

Ser Gly Thr Trp Leu Thr Tyr Thr Gly Ala Ile Lys Leu Asp Asp Lys
                85                  90                  95

Asp Pro Asn Phe Lys Asp Gln Val Ile Leu Leu Asn Lys His Ile Asp
            100                 105                 110

Ala Tyr Lys Thr Phe Pro
        115
```

<210> SEQ ID NO 11
<211> LENGTH: 414
<212> TYPE: DNA
<213> ORGANISM: Artificial Sequence
<220> FEATURE:
<223> OTHER INFORMATION: Gene coding polypeptide bound to the N-terminus of SARS-CoV-2-B.1.1.351 Spike protein

<400> SEQUENCE: 11

```
atgggcctgc ccaacaacac cgccagctgg tttaccgccc tgacccagca cggcaaggag      60

gacctgaagt tccccagagg ccagggcgtg cccattaaca ccaacagcag ccccgacgac     120

cagatcggct actacagaag agccaccaga agaatcagag gcggcgacgg caagatgaag     180

gacctgagcc ccagatggta cttctactat ctgggaaccg gccccgaagc cggcctgccc     240

tatggcgcca acaaagatgg catcatctgg gtggccaccg aaggcgccct gaacaccccc     300

aaggatcaca tcggaaccag aaatcccgcc aacaatgccg ccatcgtgct gcagctgccc     360

cagggaacca ccctgcctaa aggcttttat gccgaaggaa gcagaggagg aagc           414
```

<210> SEQ ID NO 12
<211> LENGTH: 357
<212> TYPE: DNA
<213> ORGANISM: Artificial Sequence
<220> FEATURE:
<223> OTHER INFORMATION: Gene coding polypeptide bound to the C-terminus of SARS-CoV-2-B.1.1.351 Spike protein

<400> SEQUENCE: 12

```
accaaaaaga gcgccgccga ggccagcaaa aagcccagac agaaaagaac cgccaccaag      60

gcctacaatg tgacccaggc ctttggcaga agaggacccg agcagaccca gggcaatttt     120

ggcgaccagg agctgatcag acagggcacc gactacaaac actggcccca gatcgcccag     180

ttcgccccca gcgccagcgc cttcttcggc atgagcagaa tcggcatgga ggtgaccccc     240
```

agcggcacct ggctgaccta caccggcgcc atcaagctgg acgacaagga ccccaacttc 300
aaggaccagg tgatcctgct gaacaagcac atcgacgcct acaagacctt cccctga 357

<210> SEQ ID NO 13
<211> LENGTH: 494
<212> TYPE: PRT
<213> ORGANISM: Artificial Sequence
<220> FEATURE:
<223> OTHER INFORMATION: Human papillomavirus type 16, E6, E7 & Human papillomavirus type 18, E6, E7 modified amino acid sequence

<400> SEQUENCE: 13

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Lys
            100                 105                 110

Gln Arg His Leu Asp Lys Lys Gln Arg Phe His Asn Ile Arg Gly Arg
        115                 120                 125

Trp Thr Gly Arg Cys Met Ser Cys Cys Arg Ser Ser Arg Thr Arg Arg
    130                 135                 140

Glu Thr Gln Leu Met His Gly Asp Thr Pro Thr Leu His Glu Tyr Met
145                 150                 155                 160

Leu Asp Leu Gln Pro Glu Thr Thr Gln Leu Asn Asp Ser Ser Glu Glu
                165                 170                 175

Glu Asp Glu Ile Asp Gly Pro Ala Gly Gln Ala Glu Pro Asp Arg Ala
            180                 185                 190

His Tyr Asn Ile Val Thr Phe Cys Cys Lys Cys Asp Ser Thr Leu Arg
        195                 200                 205

Leu Cys Val Gln Ser Thr His Val Asp Ile Arg Thr Leu Glu Asp Leu
    210                 215                 220

Leu Met Gly Thr Leu Gly Ile Val Cys Pro Ile Cys Ser Gln Lys Pro
225                 230                 235                 240

Arg Gly Arg Lys Arg Arg Ser Met Ala Arg Phe Glu Asp Pro Thr Arg
                245                 250                 255

Arg Pro Tyr Lys Leu Pro Asp Leu Cys Thr Glu Leu Asn Thr Ser Leu
            260                 265                 270

Gln Asp Ile Glu Ile Thr Cys Val Tyr Cys Lys Thr Val Leu Glu Leu
        275                 280                 285

Thr Glu Val Phe Glu Phe Ala Phe Lys Asp Leu Phe Val Val Tyr Arg
    290                 295                 300

Asp Ser Ile Pro His Ala Ala Cys His Lys Cys Ile Asp Phe Tyr Ser
305                 310                 315                 320

Arg Ile Arg Glu Leu Arg His Tyr Ser Asp Ser Val Tyr Gly Asp Thr
                325                 330                 335

Leu Glu Lys Leu Thr Asn Thr Gly Leu Tyr Asn Leu Leu Ile Arg Cys

```
            340                 345                 350

Leu Lys Leu Arg His Leu Asn Glu Lys Arg Arg Phe His Asn Ile Ala
        355                 360                 365

Gly His Tyr Arg Gly Gln Cys His Ser Cys Cys Asn Arg Ala Arg Gln
    370                 375                 380

Glu Arg Leu Gln Arg Arg Arg Glu Thr Gln Val Met His Gly Pro Lys
385                 390                 395                 400

Ala Thr Leu Gln Asp Ile Val Leu His Leu Glu Pro Gln Asn Glu Ile
                405                 410                 415

Pro Val Gln Leu Ser Asp Ser Glu Glu Glu Asn Asp Glu Ile Asp Gly
            420                 425                 430

Val Asn His Gln His Leu Pro Ala Arg Arg Ala Glu Pro Gln Arg His
        435                 440                 445

Thr Met Leu Cys Met Cys Cys Lys Cys Glu Ala Arg Ile Glu Leu Val
    450                 455                 460

Val Glu Ser Ser Ala Asp Asp Leu Arg Ala Phe Gln Gln Leu Phe Leu
465                 470                 475                 480

Asn Thr Leu Ser Phe Val Cys Pro Trp Cys Ala Ser Gln Gln
                485                 490


<210> SEQ ID NO 14
<211> LENGTH: 1482
<212> TYPE: DNA
<213> ORGANISM: Artificial Sequence
<220> FEATURE:
<223> OTHER INFORMATION: Human papillomavirus type 16, E6, E7 & Human
      papillomavirus type 18, E6, E7 modified nucleic acid sequence

<400> SEQUENCE: 14

atgcaccaga agagaacagc catgttccag gaccctcagg aacggccacg gaagctccca     60

caactttgta cagagctgca aacaaccatt catgacatca tccttgaatg cgtttactgc    120

aagcagcaac ttctgcgccg ggaagtctac gatttcgctt tcagagatct gtgcatcgtg    180

tatagagacg ggaaccccta cgccgtgtgt gacaaatgcc ttaaattcta cagtaagatt    240

tcagagtacc ggcattattg ctacagcctt tatggaacta cattggagca gcagtacaac    300

aaacctttgt gcgatcttct tatccggtgc attaagcaac ggcacttgga caaaaaacaa    360

cggttccata acatcagggg caggtggact ggacgctgca tgagttgctg tcgctcaagc    420

cgcactcgga gagagactca actgatgcat ggtgatactc caactttgca cgaatatatg    480

ttggacctcc aacccgaaac tacccaactg aatgacagct ctgaggaaga ggacgaaatc    540

gacggccctg cagggcaagc cgaacctgac agggcccatt ataacattgt gacattttgc    600

tgcaaatgcg atagtacttt gagactctgt gtgcagtcaa ctcatgttga cattagaaca    660

cttgaagacc tcctcatggg gacactgggg attgtttgcc caatctgttc acagaaaccc    720

agaggccgca aaaggcggtc tatggctcgc tttgaggacc ctacaaggag gccctacaag    780

ctccccgatt tgtgtacaga actgaatacc agtcttcagg atattgaaat cacttgcgtc    840

tactgcaaaa ctgtgctcga acttaccgaa gtctttgaat ttgccttcaa ggaccttttt    900

gttgtgtatc gcgattcaat cccacacgca gcctgtcaca aatgtattga cttctactct    960

aggatcagag aattgaggca ctattcagac tctgtgtatg gcgacacctt ggaaaaattg   1020

accaacactg gattgtataa tctgcttatt cggtgtctta agctccggca cttgaacgaa   1080

aaacgcagat tccacaacat tgccgggcat tatcgcgggc aatgccattc ttgttgcaat   1140

cgcgcccgcc aggagcggct gcaaaggcgc agagagactc aggtgatgca tggacccaag   1200
```

```
gccactctcc aggacatcgt ccttcatctt gaaccccaga acgaaattcc cgttcaactt   1260

agcgactcag aagaagaaaa tgatgaaatc gacggagtga accatcagca tctcccagca   1320

agaagagccg agccacaaag acacacaatg ctctgtatgt gctgcaagtg tgaagcacgg   1380

atcgaactcg tcgtcgaatc tagtgcagat gatctcagag cctttcaaca gctcttcttg   1440

aatacactga gctttgtctg tccatggtgc gctagtcaac aa                      1482


<210> SEQ ID NO 15
<211> LENGTH: 37
<212> TYPE: PRT
<213> ORGANISM: Artificial Sequence
<220> FEATURE:
<223> OTHER INFORMATION: HVR1

<400> SEQUENCE: 15

Pro Cys Glu Trp Asp Glu Ala Ala Thr Ala Leu Glu Ile Asn Leu Glu
1               5                   10                  15

Glu Glu Asp Asp Asp Asn Glu Asp Glu Val Asp Glu Gln Ala Glu Gln
            20                  25                  30

Gln Lys Thr His Val
        35


<210> SEQ ID NO 16
<211> LENGTH: 8
<212> TYPE: PRT
<213> ORGANISM: Artificial Sequence
<220> FEATURE:
<223> OTHER INFORMATION: HVR2

<400> SEQUENCE: 16

Val Glu Gly Gln Thr Pro Lys Tyr
1               5


<210> SEQ ID NO 17
<211> LENGTH: 12
<212> TYPE: PRT
<213> ORGANISM: Artificial Sequence
<220> FEATURE:
<223> OTHER INFORMATION: HVR3

<400> SEQUENCE: 17

Ser Gln Trp Tyr Glu Thr Glu Ile Asn His Ala Ala
1               5                   10


<210> SEQ ID NO 18
<211> LENGTH: 18
<212> TYPE: PRT
<213> ORGANISM: Artificial Sequence
<220> FEATURE:
<223> OTHER INFORMATION: HVR4

<400> SEQUENCE: 18

Gly Ile Leu Val Lys Gln Gln Asn Gly Lys Leu Glu Ser Gln Val Glu
1               5                   10                  15

Met Gln


<210> SEQ ID NO 19
<211> LENGTH: 17
<212> TYPE: PRT
<213> ORGANISM: Artificial Sequence
<220> FEATURE:
<223> OTHER INFORMATION: HVR5
```

<400> SEQUENCE: 19

Ser Thr Thr Glu Ala Thr Ala Gly Asn Gly Asp Asn Leu Thr Pro Lys
1               5                   10                  15

Val

<210> SEQ ID NO 20
<211> LENGTH: 12
<212> TYPE: PRT
<213> ORGANISM: Artificial Sequence
<220> FEATURE:
<223> OTHER INFORMATION: HVR6

<400> SEQUENCE: 20

Thr Ile Lys Glu Gly Asn Ser Arg Glu Leu Met Gly
1               5                   10

<210> SEQ ID NO 21
<211> LENGTH: 41
<212> TYPE: PRT
<213> ORGANISM: Artificial Sequence
<220> FEATURE:
<223> OTHER INFORMATION: HVR7

<400> SEQUENCE: 21

Gly Gly Val Ile Asn Thr Glu Thr Leu Thr Lys Val Lys Pro Lys Thr
1               5                   10                  15

Gly Gln Glu Asn Gly Trp Glu Lys Asp Ala Thr Glu Phe Ser Asp Lys
            20                  25                  30

Asn Glu Ile Arg Val Gly Asn Asn Phe
        35                  40

<210> SEQ ID NO 22
<211> LENGTH: 22
<212> TYPE: PRT
<213> ORGANISM: Artificial Sequence
<220> FEATURE:
<223> OTHER INFORMATION: HVR1

<400> SEQUENCE: 22

Ser Ser Gln Trp Asp Ala Gln Glu Lys Ser Gly Gln Gly Ser Asp Met
1               5                   10                  15

Val Thr Lys Thr His Thr
            20

<210> SEQ ID NO 23
<211> LENGTH: 13
<212> TYPE: PRT
<213> ORGANISM: Artificial Sequence
<220> FEATURE:
<223> OTHER INFORMATION: HVR2

<400> SEQUENCE: 23

Thr Glu Ile Thr Ala Asp Asn Gln Lys Lys Glu Ile Phe
1               5                   10

<210> SEQ ID NO 24
<211> LENGTH: 11
<212> TYPE: PRT
<213> ORGANISM: Artificial Sequence
<220> FEATURE:
<223> OTHER INFORMATION: HVR3

<400> SEQUENCE: 24

Glu Asn Trp Gln Glu Asn Glu Val Phe Tyr Gly 1 5 10

<210> SEQ ID NO 25
<211> LENGTH: 24
<212> TYPE: PRT
<213> ORGANISM: Artificial Sequence
<220> FEATURE:
<223> OTHER INFORMATION: Primer

<400> SEQUENCE: 25

Gly Thr Ala Ala Cys Cys Gly Cys Ala Thr Ala Cys Gly Ala Gly Cys
1 5 10 15

Ala Gly Ala Cys Gly Gly Thr Gly
20

<210> SEQ ID NO 26
<211> LENGTH: 15
<212> TYPE: PRT
<213> ORGANISM: Artificial Sequence
<220> FEATURE:
<223> OTHER INFORMATION: HVR5

<400> SEQUENCE: 26

Asp Thr Asp Gly Gly Thr Ala Asp Thr Glu Tyr Lys Ala Asp Ile
1 5 10 15

<210> SEQ ID NO 27
<211> LENGTH: 12
<212> TYPE: PRT
<213> ORGANISM: Artificial Sequence
<220> FEATURE:
<223> OTHER INFORMATION: HVR6

<400> SEQUENCE: 27

Gly Lys Glu Asp Asp Ser Ser Glu Ile Asn Leu Val
1 5 10

<210> SEQ ID NO 28
<211> LENGTH: 43
<212> TYPE: PRT
<213> ORGANISM: Artificial Sequence
<220> FEATURE:
<223> OTHER INFORMATION: HVR7

<400> SEQUENCE: 28

Asp Gly Leu Gly Thr Asn Ala Thr Tyr Gln Gly Val Lys Val Ser Thr
1 5 10 15

Gly Asp Gly Ala Thr Gln Ser Gly Trp Ala Lys Asp Asp Thr Met Ala
20 25 30

Arg Gln Asn Gln Ile Cys Arg Gly Asn Ile Tyr
35 40

<210> SEQ ID NO 29
<211> LENGTH: 33
<212> TYPE: DNA
<213> ORGANISM: Artificial Sequence
<220> FEATURE:
<223> OTHER INFORMATION: Primer

<400> SEQUENCE: 29
taagggtggg aaagaatata taaggtgggg gtc 33

<210> SEQ ID NO 30
<211> LENGTH: 22
<212> TYPE: DNA

<213> ORGANISM: Artificial Sequence
<220> FEATURE:
<223> OTHER INFORMATION: Primer

<400> SEQUENCE: 30
gccttccatc aagggcatcc cg 22

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
gtaaagttcc aagaagcgcg ggatgc 26

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
agttaatctc ctggttcacc gtctg 25

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
gtaaccgcat acgagcagac ggtg 24

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
cgtggagcgg aaggtcacg 19

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
gccagacatg atgcaagacc ccgtg 25

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
cgtaccactg agattctcct atttgaggtt c 31

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
caacctgaac ctcaaatagg agaatctcag 30

<210> SEQ ID NO 38
<211> LENGTH: 29
<212> TYPE: DNA
<213> ORGANISM: Artificial Sequence
<220> FEATURE:
<223> OTHER INFORMATION: Primer

<400> SEQUENCE: 38
ggataacgat ctaaaggcga acttcaaac 29

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
gtcaggcagt agtttgaagt tcgc 24

<210> SEQ ID NO 40
<211> LENGTH: 42
<212> TYPE: DNA
<213> ORGANISM: Artificial Sequence
<220> FEATURE:
<223> OTHER INFORMATION: Primer

<400> SEQUENCE: 40
ctctagttat aactagagga tcttgatgta atccagggtt ag 42

<210> SEQ ID NO 41
<211> LENGTH: 44
<212> TYPE: DNA
<213> ORGANISM: Artificial Sequence
<220> FEATURE:
<223> OTHER INFORMATION: Primer

<400> SEQUENCE: 41
cctctagtta taactagagt acccgggatc ttattccctt taac 44

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
cggagtaact tgtatgtgtt gggaattg 28

<210> SEQ ID NO 43
<211> LENGTH: 28
<212> TYPE: DNA
<213> ORGANISM: Artificial Sequence
<220> FEATURE:

<223> OTHER INFORMATION: Primer

<400> SEQUENCE: 43
caattcccaa cacatacaag ttactccg 28

<210> SEQ ID NO 44
<211> LENGTH: 40
<212> TYPE: DNA
<213> ORGANISM: Artificial Sequence
<220> FEATURE:
<223> OTHER INFORMATION: Primer

<400> SEQUENCE: 44
tatattcttt cccaccctta cgcgttaaga tacattgatg 40

<210> SEQ ID NO 45
<211> LENGTH: 39
<212> TYPE: DNA
<213> ORGANISM: Artificial Sequence
<220> FEATURE:
<223> OTHER INFORMATION: Primer

<400> SEQUENCE: 45
cctttgctac caactcattc tctttttcat acattgccc 39

<210> SEQ ID NO 46
<211> LENGTH: 40
<212> TYPE: DNA
<213> ORGANISM: Artificial Sequence
<220> FEATURE:
<223> OTHER INFORMATION: Primer

<400> SEQUENCE: 46
acaattaggg cttgggtcag gtgtggtcca caaagttagc 40

<210> SEQ ID NO 47
<211> LENGTH: 40
<212> TYPE: DNA
<213> ORGANISM: Artificial Sequence
<220> FEATURE:
<223> OTHER INFORMATION: Primer

<400> SEQUENCE: 47
gctaactttg tggaccacac ctgacccaag ccctaattgt 40

<210> SEQ ID NO 48
<211> LENGTH: 39
<212> TYPE: DNA
<213> ORGANISM: Artificial Sequence
<220> FEATURE:
<223> OTHER INFORMATION: Primer

<400> SEQUENCE: 48
gggcaatgta tgaaaaagag aatgagttgg tagcaaagg 39

<210> SEQ ID NO 49
<211> LENGTH: 40
<212> TYPE: DNA
<213> ORGANISM: Artificial Sequence
<220> FEATURE:
<223> OTHER INFORMATION: Primer

<400> SEQUENCE: 49
tgcaggggta acatctacgc catggaaatc aatctaaatg 40

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50
tgcgcatccc actgactgga atttggggca cccttgggag 40

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
ctcccaaggg tgccccaaat tccagtcagt gggatgcgca 40

<210> SEQ ID NO 52
<211> LENGTH: 40
<212> TYPE: DNA
<213> ORGANISM: Artificial Sequence
<220> FEATURE:
<223> OTHER INFORMATION: Primer

<400> SEQUENCE: 52
catttagatt gatttccatg gcgtagatgt taccccctgca 40

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
ctaagcttct agataagata tccgatccac 30

<210> SEQ ID NO 54
<211> LENGTH: 31
<212> TYPE: DNA
<213> ORGANISM: Artificial Sequence
<220> FEATURE:
<223> OTHER INFORMATION: Primer

<400> SEQUENCE: 54
cgcgtcgacg gtaccagatc tctagcggat c 31

<210> SEQ ID NO 55
<211> LENGTH: 41
<212> TYPE: DNA
<213> ORGANISM: Artificial Sequence
<220> FEATURE:
<223> OTHER INFORMATION: Primer

<400> SEQUENCE: 55
gatctggtac cgtcgacgcg atgtttgtgt ttctggtgct g 41

<210> SEQ ID NO 56
<211> LENGTH: 41
<212> TYPE: DNA
<213> ORGANISM: Artificial Sequence
<220> FEATURE:
<223> OTHER INFORMATION: Primer

<400> SEQUENCE: 56
tatcttatct agaagcttag tcaggtatag tgcagtttca c 41

<210> SEQ ID NO 57
<211> LENGTH: 40
<212> TYPE: DNA
<213> ORGANISM: Artificial Sequence
<220> FEATURE:
<223> OTHER INFORMATION: Primer

<400> SEQUENCE: 57
gatctggtac cgtcgacgcg atgggcctgc ccaacaacac 40

<210> SEQ ID NO 58
<211> LENGTH: 41
<212> TYPE: DNA
<213> ORGANISM: Artificial Sequence
<220> FEATURE:
<223> OTHER INFORMATION: Primer

<400> SEQUENCE: 58
tatcttatct agaagcttag tcaggggaag gtcttgtagg c 41

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
ctaagcttct agataagata tccgatccac 30

<210> SEQ ID NO 60
<211> LENGTH: 31
<212> TYPE: DNA
<213> ORGANISM: Artificial Sequence
<220> FEATURE:
<223> OTHER INFORMATION: Primer

<400> SEQUENCE: 60
cgcgtcgacg gtaccagatc tctagcggat c 31

<210> SEQ ID NO 61
<211> LENGTH: 38
<212> TYPE: DNA
<213> ORGANISM: Artificial Sequence
<220> FEATURE:
<223> OTHER INFORMATION: Primer

<400> SEQUENCE: 61
gatctggtac cgtcgacgcg atgcaccaga agagaaca 38

<210> SEQ ID NO 62
<211> LENGTH: 44
<212> TYPE: DNA
<213> ORGANISM: Artificial Sequence
<220> FEATURE:
<223> OTHER INFORMATION: Primer

<400> SEQUENCE: 62
tatcttatct agaagcttag ttattgttga ctagcgcacc atgg 44

RECOMBINANT CHIMERIC ADENOVIRAL VECTOR SUBSTITUTED BY KNOB GENE OF CHIMPANZEE ADENOVIRUS SEROTYPE 6, AND APPLICATION THEREOF

TECHNICAL FIELD

The present invention relates to a chimeric adenovirus vector having optimal conditions for avoiding pre-existing immunity against human adenovirus serotype 5 (HAdV-5) in a host. Specifically, it relates to a chimeric adenovirus vector expressing the knob protein and/or hexon protein of an adenovirus serotype with low seroprevalence based on the HAdV-5 gene sequence, and prophylactic and therapeutic vaccine applications against SARS-COV-2 and human papillomavirus based on the chimeric adenovirus vectors.

REFERENCE TO AN ELECTRONIC SEQUENCE LISTING

The content of the electronic sequence listing (OP22-0008HSUS_SEQLIST.TXT; Size: 50,320 bytes; and Date of Creation: Jun. 14, 2024), filed via Patent Center on Jun. 17, 2024, is herein incorporated by reference in its entirety.

BACKGROUND ART

Adenovirus is a medium-sized nonenveloped virus with a diameter of about 90-100 mm containing linear double stranded DNA in a nucleocapsid. It is found in a variety of vertebrates (amphibians, birds, and mammals), most of which cause respiratory infections, conjunctivitis and gastroenteritis. In contrast to retroviruses, since it is not inserted into the genome of host cells, transformation of host cells or tumorigenesis by adenovirus DNA does not occur, transduction into non-dividing cells is possible, and virus productivity is high. Because of their characteristics, adenoviral vectors have been widely studied for gene therapy and vaccine applications.

First-generation recombinant adenovirus vectors delete E1 and E3 genes, which are early transcription genes involved in viral replication, and from a clinical point of view, they are replication-incompetent in the host. side effects were reduced by making it, and there were fewer restrictions on inserting a foreign gene (up to about 8 Kb). So far, human adenovirus serotypes 2 and 5 (AdH2 and HAdV-5) belonging to subgroup C have been studied most as vectors, and recombinant HAdV-5 vector-based vaccines have been developed in preclinical trials. Excellent vaccine efficacy was demonstrated by showing highly immunogenic results through various animal models.

However, a clinical trial of an HIV vaccine developed based on a recombinant HAdV-5 vector showed insufficient efficacy different from non-clinical results. HAdV-5 is one of the most infected adenovirus serotypes, and it has been reported that about 80% or more of the population has anti-HAdV-5 neutralizing antibodies due to pre-existing immunity. As shown in the results of HIV vaccine clinical trials, anti-HAdV-5 neutralizing antibodies formed by pre-existing immunity bind to recombinant HAdV-5 vector-based vaccines loaded with foreign genes, reducing vaccine efficacy.

The icosahedral envelope protein of adenovirus is the main capsid protein and is composed of hexon, fiber and penton proteins. Hexon is a protein that occupies the largest portion of adenovirus envelope proteins and includes a hypervariable region (HVR) with low genetic homology between adenovirus serotypes. Penton is a protein responsible for the structural stability and flexibility of envelope proteins and is involved in cell entry through the Arg-Gly-Asp (RGD) motif. In addition, the fiber binds to the host cell's receptor, CAR (Coxsackie and adenovirus receptor), through a knob domain at the end, and cell entry occurs. Three coat proteins (hexon, fiber and penton) are known to act as major recognition sites for anti-Ad neutralizing antibodies. Recently, to avoid existing immunity to HAdV-5, a chimeric adenovirus vector study was reported in which the projection domain of the fiber protein was replaced with a human adenovirus serotype with low seroprevalence. However, in the case of chimeric adenoviral vectors using human adenovirus serotypes, there is a possibility of cross-reactivity with neutralizing antibodies against HAdV-5, so the ability to evade existing immunity against HAdV-5 may be reduced.

To avoid cross-reactive immunity with neutralizing antibodies to HAdV-5, adenovirus serotypes isolated from non-human animals that are genetically distant have been developed as viral vectors. Among these non-human adenovirus vectors, a viral vector using a chimpanzee adenovirus (ChAdV) serotype is most widely used. ChAdV serotypes were investigated to have lower seroprevalence rates than HAdV-5. For example, the serum retention rates of neutralizing antibodies against ChAdV-6 and ChAdV-68 were detected in only 1.5-4% of serum samples from the US and Thailand. In addition, in the phase 1 clinical trial of the ChAdV-63-based malaria vaccine, safety and antigen-specific T cell response were high in all clinical trial volunteers. Despite the low seroprevalence of ChAdV-vector-based vaccines, high cross-reactivity between serotypes is a major concern for vector-specific cellular immunity.

Coronaviruses are positive-sense single-stranded RNA viruses that have an envelope on the surface of particles with a diameter of 100-200 mm. Seven types of coronaviruses are known to cause respiratory and digestive infections in humans, and two of the seven types are alpha-genus of coronaviruses, and the remaining five species were identified as genus beta-coronaviruses. Severe acute respiratory syndrome coronavirus 2 (hereinafter referred to as 'SARS-COV-2'), which causes COVID-19 (novel coronavirus, 2019-nCov), is a beta-coronavirus. After it was first reported in Wuhan City, China in December 2019 (Wuhan-Hu-1), confirmed cases are appearing one after another around the world, and the pandemic is intensifying through various mutations (alpha variants, beta variants, delta variants, etc.) since the outbreak.

The viral envelope of SARS-COV-2 is composed of spike glycoprotein (S protein) and hemagglutinin-esterase dimer (HE) etc., The S1 region of the S protein mainly binds to the receptor (Angiotensin-converting enzyme 2, ACE2) through the RBD (Receptor binding domain), and the S2 region is responsible for direct cell-viral fusion (initiation of infection) with dramatic changes in tertiary structure. Therefore, vaccine candidates targeting the S protein as a major antigen have been developed and commercialized (AZD-1222 (AstraZeneca), Bnt162b2 (Pfizer), mRNA-1273 (Moderna) etc.)

Unlike DNA viruses, which have DNA repair pathways (base excision repair, nucleotide excision repair, mismatch repair) that correct errors during DNA replication, RNA viruses use RNA polymerase, and so they do not have RNA repair-related proteins to correct errors generated during genome replication, so they are characterized by frequent mutations compared to DNA viruses. In the case of the SARS-COV-2 variant virus, mutations frequently occurred in the N-terminal domain (NTD) and RBD domain of the S protein, as a result, licensed vaccines developed targeting the S protein of SARS-coronavirus-2 have reduced antibody binding ability to the S protein of the variant virus in which structural changes have occurred, resulting in reduced protective efficacy against the variant virus.

In December 2020, a fatal mutation of SARS-COV-2 occurred in South Africa and was classified as a beta mutation and designated as a variant of concern (VOC). The mutant was found to be the first mutant to have all three key mutations (E484K, K417N, N501Y) of VOCs in RBD as well as deletion in NTD, and in the case of AstraZeneca's AZD-1222 vaccine, it was confirmed that the efficacy of the vaccine in the beta variant strain (B.1.351) group was reduced by 10% compared to the existing SARS-COV-2, and a rapid decline in efficacy against licensed vaccines.

In addition, as cross-neutralization was confirmed for SARS-coronavirus-2 and other variant viruses in the serum of convalescent patients who were infected with the beta mutation, the direction is changing towards the development of a vaccine targeting the S protein against the variant virus, not the S protein against SARS-COV-2, and the need for a universal vaccine that can fight against the continuous emergence of variant viruses is emerging.

HPV has about 170 HPV genotypes, which are largely classified into two groups: high risk and low risk. HPV-6/11/40/42/43/44/54/61 and 72 types are in the low-risk group for causing genital warts, and HPV-16/18/31/35/39/45/51/Including 52/56/58/66 and 68, the high-risk type is responsible for about 99.7% of cervical cancer cases.

Particularly, HPV-16 and 18 types are the most common types associated with cervical cancer worldwide, accounting for more than 70% of cases. HPV is also responsible for many penile, vulvar, and anal-related carcinomas and accounts for more than 40% of oropharyngeal cancers.

Persistent infection with these high-risk HPVs results in the development of squamous intraepithelial lesions (SILs). This is called cervical intraepithelial neoplasia (CIN) in the cervix and vulva intraepithelial neoplasia (VIN) in the vulva, and these SILs can progress to malignant cancer.

HPV is a non-enveloped virus consisting of double-stranded DNA with a genome size of approximately 8 kb. The genome encodes six early regulatory proteins (E1, E2, E4, E5, E6 and E7) and two late structural proteins (L1 and L2). Early genes encode proteins involved in viral DNA replication, transcription and oncogenic transformation, and late genes encode viral capsid proteins. In the general high-risk HPV cancer formation process, the viral genome is integrated into the host's chromosomal DNA, and the E2 genetic sequence is disrupted during gene linearization. Since E2 protein is a transcriptional repressor of E6 and E7, disruption of E2 initiates the expression of E6 and E7 proteins. The E6 protein promotes the degradation of p53, a protein that regulates apoptosis of the host, and activates telomerase to extend cell lifespan. E7 protein also targets and degrades the tumor suppressor protein retinoblastoma protein (pRb). As such, E6 and E7 interfere with cell cycle regulation and extend the lifespan of host cells, causing genetic instability, malignant transformation of cells, and cancer.

In HPV therapeutic vaccines, infection elimination in cellular immunity is more important than humoral immune response. HPV E6 and E7 oncoproteins are essential for the initiation and maintenance of malignant tumors and are expressed in pre-malignant and invasive lesions but absent from healthy cells.

Therefore, these oncoproteins (E6, E7) cannot avoid immune responses due to mutations, and are the most ideal targets for the development of therapeutic vaccines against HPV infections and lesions.

An ideal therapeutic vaccine can target E6 and E7 proteins to induce strong tumor-specific T cell type 1 and cytotoxic T lymphocyte (CTL) responses to kill infected and malignant cells.

PRIOR PATENT LITERATURE

Korean Patent Publication No. 1020040054796

DISCLOSURE

Technical Problem

The present invention has been made in response to the above needs, and an object of the present invention is to provide an adenoviral vector that is superior to conventional recombinant HAdV-5 vectors in terms of constructing a chimeric adenoviral vector that overcomes pre-existing immunity to HAdV-5 in the host.

Another object of the present invention is to provide a therapeutic or prophylactic vaccine vector capable of delivering foreign genes with high efficiency.

Another object of the present invention is to provide a chimeric adenovirus vector comprising the S gene sequence of the beta variant to prevent infection with SARS-coronavirus-2.

Another object of the present invention is to provide a vaccine for preventing infection of SARS-coronavirus-2.

Another object of the present invention is to provide a chimeric adenovirus vector comprising gene sequences of 16 types E6 and E7 and 18 types E6 and E7 of human papillomavirus.

Another object of the present invention is to provide a vaccine for the treatment and prevention of HPV.

Technical Solution

In order to achieve the above object, the present invention provides a chimeric adenoviral vector based on human adenovirus serotype 5 having excellent ability to evade existing immunity that the knob domain at the end of the fiber protein of human adenovirus type 5 is substituted with the knob gene of chimpanzee adenovirus serotype 6, or the hexon protein of human adenovirus type 5 is substituted with hypervariable regions 1-7 of human adenovirus serotype 28 in the substituted type 5 adenovirus.

The present invention relates to a vector capable of avoiding pre-existing immunity to human adenovirus type 5 to overcome the decrease in efficacy when exogenous gene transfer due to existing immunity in humans against human adenovirus type 5.

In the present invention, the replacement site of the HAdV-5 gene is the knob domain of the fiber protein. Fiber proteins are composed of three domains (tail, shaft, and knob), among which the knob domain is known as a major recognition site for neutralizing antibodies.

In one embodiment of the present invention, the protein expressed by the chimpanzee adenovirus serotype 6 knob gene preferably includes the amino acid sequence of SEQ ID NO: 1 but is not limited thereto.

In another embodiment of the present invention, the knob gene sequence of the chimpanzee adenovirus serotype 6 preferably comprises the nucleic acid sequence of SEQ ID NO: 2 but is not limited thereto.

The knob sequence of the present invention uses the gene sequence of a rare adenovirus serotype having a low serum retention rate in humans. For example, there are ChAdV-1, ChAdV-2, ChAdV-3, ChAdV-5, ChAdV-7, ChAdV-68, etc. In addition to chimpanzee adenovirus, adenovirus serotypes found in cattle, pigs, birds, etc. can be used.

The present invention provides a chimeric adenovirus vector comprising the tail and shaft domains of human adenovirus type 5 and the knob combined fiber protein of chimpanzee adenovirus serotype 6.

In another embodiment of the present invention, the chimeric protein in which the hexon protein of human adenovirus type 5 is substituted with hypervariable regions 1-7 of human adenovirus serotype 28 has the amino acid sequence of SEQ ID NO: 3, The hypervariable region gene sequence in the hexon protein of the human adenovirus serotype 28 preferably comprises the nucleic acid sequence of SEQ ID NO: 4 but is not limited thereto.

The hexon hypervariable region sequence of the present invention uses the gene sequence of a rare adenovirus serotype having a low serum retention rate in humans. For example, there are HAdV-14, HAdV-19, HAdV-32, HAdV-34, HAdV-36, HAdV-43, etc., and adenovirus serotypes found in cattle, pigs, birds, etc. besides humans can be used.

In the present invention, a chimeric adenoviral vector comprising a hexon protein obtained by replacing a hypervariable region in a hexon protein of human adenovirus type 5 with a gene of human adenovirus type 28 in an adenovirus vector comprising a fiber protein combined with the knob gene of chimpanzee adenovirus serotype 6 is provided.

The vector of the present invention is characterized in that it comprises Inverted terminal repeat (ITR) sequence, BR322 origin of replication, kanamycin resistance gene, ITR sequence, encapsidation signal, CMV enhancer, CMV promoter, and SV40 ploy (A) signal as vector regulators of the present invention.

The vector preferably comprises a BR322 origin of replication and an antibiotic resistance gene, and preferably uses a kanamycin resistance gene (Kan) but is not limited thereto. Antibiotic resistance genes for ampicillin, chloramphenicol, tetracycline, or neomycin may be used as antibiotics used for selection.

The vector preferably comprises an inverted terminal repeat (ITR) sequence and an encapsidation signal of adenovirus. ITR sequences and encapsidation sequences are essential elements for adenoviral DNA replication and packaging, respectively.

The vector preferably comprises, but is not limited to, a cytomegalovirus immediate early enhancer (CMV enhancer) as an enhancer. For example, an enhancer of Simian virus 40 (SV40) may be used as an enhancer.

The promoter is preferably a virus-derived or mammalian-derived promoter, and specifically refers to a cytomegalovirus (CMV) promoter. The CMV promoter is recognized as a powerful promoter that efficiently induces exogenous gene expression in all mammalian and insect cells.

The SV40 poly(A) signal sequence of the vector refers to the poly adenyl signal of Simian virus 40 (SV40) and is preferably comprised in the vector. The use of the SV40 poly(A) signal sequence increases the stability of messenger RNA (mRNA), making protein expression easier.

The vector of the present invention is preferably the chimeric adenoviral vector shown in FIG. 5 or 6 but is not limited thereto.

In one embodiment of the present invention, the vector preferably comprises a) a gene encoding the coronavirus spike protein, or b) a gene encoding the E6 and E7 proteins of human papillomavirus type 16 or 18 as an insert but is not limited to thereto.

In another embodiment of the present invention, the vector is preferably capable of infecting mammalian cells but is not limited thereto.

The present invention also provides a host cell transformed with the chimeric adenoviral vector of the present invention.

In one embodiment of the present invention, the transformed cell of the chimeric adenoviral vector that substituted with the chimpanzee adenovirus knob gene and the chimeric adenoviral vector substituted with the hexon hypervariable region of a rare human adenovirus is preferably mammalian cells including HEK293, PERC6 or 911 cells, more preferably HEK293 cells but are not limited thereto.

For example, an adenovirus-producing cell suitable for the present invention should be a cell capable of producing a virus by trans-complementation of the E1 and E3 gene deletion sites of a replication defective adenovirus, and many cells transformed with the viral early transcription genes are being developed. Preferred cells into which the E1 and E3 genes are introduced comprise A549 (carcinomic human alveolar basal epithelial cell), HeLa (Human cervical cancer cell), CHO (Chinese hamster ovary cell), MRC5 (human lung fibroblast), and PC12 (rat pheochromocytoma cell) etc but not limited thereto.

The present invention also provides an isolated polypeptide encoded by the chimeric adenoviral vector of the present invention.

In addition, the present invention provides a vaccine composition comprising the chimeric adenovirus vector of the present invention or a polypeptide encoded by the vector as an active ingredient.

In the present invention, the above elements are artificially synthesized and provide a vector through the Gibson assembly method.

In an embodiment of the present invention, the chimeric adenovirus vector-based vaccine is preferably beta variant S or human papillomavirus types 16 and 18 E6E7 proteins but is not limited thereto.

In addition, the present invention provides mouse immunity and virus neutralization efficacy by using the beta variant strain S based on the chimeric adenovirus vector.

In addition, the present invention provides the efficacy for the immune response of specific T cells according to the beta variant strain S based on the chimeric adenovirus vector. The present invention provides protective efficacy against SARS-coronavirus-2 and delta variant virus after immunization with beta variant S virus based on chimeric adenovirus vector.

The present invention provides the efficacy of mouse tumor cell therapy using HPV16 and 18 E6E7 viruses based on the chimeric adenovirus vector.

The present invention provides efficacy against the immune response of specific T cells against HPV16 and 18 E6E7 viruses based on a chimeric adenovirus vector.

The present invention provides the efficacy of mouse tumor cell prevention using HPV16 and 18 E6E7 viruses based on chimeric adenovirus vectors.

In addition, the present invention provides a vaccine composition for preventing or treating an infection of SARS-COV-2 by the chimeric adenovirus vector of the present invention or being encoded by the vector.

In addition, the present invention provides a composition characterized in that it is a vaccine for treating cervical cancer of human papillomavirus disease by the chimeric adenovirus vector of the present invention or being encoded by the vector.

The present invention will be described below.

The present inventors have made diligent efforts to develop a chimeric adenovirus vector that improves the existing immunity problems against HAdV-5 by combining the capsid protein gene sequences of adenovirus serotypes with low serum retention, and as a result, the present invention was completed by confirming that the ChimAd vector in which the knob gene sequence was replaced with the corresponding gene of ChAdV-6 based on the recombinant HAdV-5 vector, or ChimAd-H28 vector in which the hypervariable region in the hexon protein of HAdV-5 was replaced with the corresponding gene of serotype 28 can be usefully used as an optimal adenoviral vector.

Since more than 80% of the population naturally possesses neutralizing antibodies against adenovirus, vaccines based on adenovirus vectors loaded with foreign genes have a problem in that immune efficacy is reduced due to existing immunity against HAdV-5. The developed chimeric adenoviral vector presents the potential as an excellent adenoviral vector that improves these problems of the conventional recombinant HAdV-5 vector through cytopathic effect (CPE) and in vitro neutralizing antibody tests.

Specifically, the present invention provides an AdKnob vector in which the gene sequence of the HAdV-5 knob domain is replaced with the corresponding gene of chimpanzee adenovirus serotype 6, a rare serotype, based on a recombinant vector.is. based on a recombinant HAdV-5 vector composed of a BR322 origin of replication, a kanamycin resistance gene, an inverted terminal repeat (ITR) sequence, an encapsidation signal, a CMV enhancer, a CMV promoter, and a SV40 poly(A) signal sequence.

In addition, the present invention provides a ChimAd-H28 vector in which a region in the hexon protein of HAdV-5 is replaced with a corresponding gene of HAdV-28, an adenovirus serotype with low human seroprevalence, based on the ChimAd vector.

The present invention provides the existing immune avoidance effect by testing the cell infectivity and neutralizing antibody for the ChimAd and ChimAd-H28 vectors.

To analyze the cell infectivity of the chimeric adenovirus provided in the present invention, compared to the existing HAdV-5, the virus titer was measured under the same MOI virus dose (multiplicity of infection) and time conditions. As a result, it was confirmed that the number of cells infected with the chimeric adenovirus and the virus titer increased more than the HAdV-5 virus. Due to the knob gene of ChAdV-6 and the HVR gene of HAdV-28, the ability to infect host cells increased, and the virus productivity increased, compared to HAdV-5.

In addition, in the present invention, the neutralizing antibody immunity evasion ability of the ChimAd vector against HAdV-5 was evaluated through an in vitro neutralizing antibody test. In the in vitro neutralizing antibody test, anti-HAdV-5 antibody and virus were reacted, were infected to HEK293 cells, and finally cells infected with HAdV-5, ChimAd and ChimAd-H28 viruses were identified. As a result, when compared with the HAdV-5 virus, about 4 times more adenovirus-infected cells were confirmed in $10^1$-$10^2$ by the ChimAd virus, indicating a higher ability to evade existing immunity than the conventional HAdV-5. In addition, about 2.8 times more infected cells were identified by the ChimAd-H28 virus.

The present invention provides a composition comprising an immunological adjuvant, the chimeric vector or a polypeptide encoded by the vector, and optionally a pharmaceutically acceptable excipient.

A composition according to the invention comprising an adjuvant can be used, for example, as a vaccine for human subjects. Immunological adjuvants, also referred to herein as "adjuvants" for short, accelerate, prolong and/or enhance the quality and/or strength of the immune response to the antigen/immunogenicity, compared to administration of the antigen alone. This reduces the amount of antigen/immunogen required for any given vaccine and/or the frequency of injections required to generate an adequate immune response to the desired antigen/immunogen.

Examples of adjuvants that may be used in connection with the composition according to the present invention are gel-like precipitates of aluminum hydroxide (allum); AlPO4; alhydrogel; bacterial products from the outer membrane of Gram-negative bacteria, in particular monophosphoryl lipid A (MPLA), lipopolysaccharide (LPS), muramyldipeptide and derivatives thereof; Freund's incomplete adjuvant; liposomes, particularly neutral liposomes, liposomes containing a composition and optionally a cytokine; non-ionic block copolymers; ISCOMATRIX adjuvant (Drane et al, 2007); unmethylated DNA containing CpG dinucleotides (CpG motifs), in particular CpG ODNs having a phosphorothioate (PTO) backbone (CpG PTO ODN) or phosphodiester (PO) backbones (CpG PO ODN); synthetic lipopeptide derivatives, particularly Pam3Cys; lipoarabinomannan; peptidoglycan; zymosan; heat shock proteins (HSP), especially HSP 70; dsRNA and its synthetic derivatives, particularly Poly I:poly C; polycationic peptides, especially poly-L-arginine; taxol; fibronectin; flagellin; imidazoquinoline; cytokines with adjuvant activity, in particular GM-CSF, interleukin-(IL-)2, IL-6, IL-7, IL-18, type I and type II interferons, in particular interferon-gamma, TNF-alpha; 25-dihydrophytamine D3 (calcitriol); and synthetic oligopeptides, particularly MHCII-provided peptides. Non-ionic block polymers containing polyoxyethylene (POE) and polyoxypropylene (POP), for example POE-POP-POE block copolymers, can be used as adjuvants (Newman et al, 1998). Adjuvants of this type are particularly useful for compositions that include nucleic acids as active ingredients.

If desired, various pharmaceutically acceptable excipients may be used. Preferred pharmaceutically acceptable excipients are mentioned below when discussing the use according to the present invention.

Activation of specific receptors can stimulate an immune response. Such receptors are known to the person skilled in the art and include, for example, cytokine receptors, especially type I cytokine receptors, type II cytokine receptors, TNF receptors; and vitamin D receptors that act as transcription factors; and toll-like receptor 1 (TLR1), TLR-2, TLR 3, TLR4, TLR5, TLR-6, TLR7, and TLR9. Agonists for these receptors have adjuvant activity, ie are immunostimulatory.

According to an embodiment of the present invention, ChimAd-CV and ChimAd-CVN comprising the S sequence of the beta variant strain based on the ChimAd vector and the N partial sequence of SARS-coronavirus-2 are provided.

In another embodiment of the present invention, the modified spike protein of the beta variant strain of SARS-coronavirus-2 is preferably comprised of the amino acid sequence shown in SEQ ID NO: 7, and the modified spike protein of the beta variant strain of SARS-coronavirus-2 The gene encoding the modified spike protein of the beta variant strain of SARS-coronavirus-2 is preferably composed of the nucleotide sequence shown in SEQ ID NO: 8 but all mutant sequences that achieve the object of the present invention through mutation of one or more substitutions, deletions, inversions, etc. to the sequence are also included in the scope of the present invention.

In one embodiment of the present invention, the amino acid residues from positions 44 to 180 of the nucleocapsid protein of the SARS-coronavirus-2 is shown in the amino acid sequence of SEQ ID NO: 9, and the amino acid residues from positions 247 to 364 of the nucleocapsid protein is preferably shown in the amino acid sequence of SEQ ID NO: 10, but all mutant sequences that achieve the object of the present invention through mutation such as one or more substitutions, deletions, inversions, etc. included in the scope of the invention.

The ChimAd-CV and ChimAd-CVN vaccine compositions produced in the present invention provide excellent neutralizing antibody titers against SARS-coronavirus-2, beta variants and delta variants.

The ChimAd-CV and ChimAd-CVN vaccine compositions produced according to an embodiment of the present invention provide excellent neutralizing antibody titers against pseudo-viruses based on beta variants.

The ChimAd-CV and ChimAd-CVN vaccine compositions produced in the present invention provide efficacy against the immune response of specific T cells.

In the present invention, the ChimAd-CV and ChimAd-CVN vaccine compositions produced by the above method provide protective efficacy against SARS-coronavirus-2 and delta variants.

Body weight change and survival rate after immunization and viral infection with ChimAd-CV and ChimAd-CVN produced according to an embodiment of the present invention were confirmed. Both experimental groups inoculated with ChimAd-CV and ChimAd-CVN against SARS-coronavirus-2 infection showed a 100% survival rate, confirming excellent defense. In addition, for delta variant infection, ChimAd-CV maintained 100% survival rate and 100% average body weight after 7 days of infection, but ChimAd-CVN showed a survival rate of 40% and average weight loss within about 20% after 7 days of infection.

According to an embodiment of the present invention, ChimAd-HPV comprising E6E7 and type 18 E6E7 sequences of human papillomavirus type 16 based on a ChimAd vector is provided.

In another embodiment of the present invention, the human papillomavirus type 16 E6E7 and type 18 E6E7 proteins are preferably comprised of the amino acid sequence shown in SEQ ID NO: 13, and The gene encoding the modified E6 and E7 of the human papillomavirus type 16 E6E7 and type 18 are preferably composed of the nucleotide sequence shown in SEQ ID NO: 14, but all mutant sequences that achieve the object of the present invention through mutation such as one or more substitutions, deletions, inversions, etc. are also included in the scope of the present invention.

In the present invention, to confirm the efficacy of human papillomavirus in treating cervical cancer, TC-1 tumor cells and the produced virus were injected. According to an embodiment of the present invention, the therapeutic efficacy was confirmed by measuring the tumor volume after injection of the recombinant antigen. As a result, the therapeutic efficacy of the ChimAd-HPV virus on tumor volume compared to the control group (ChimAd) was confirmed.

In addition, the ChimAd-HPV vaccine composition produced according to the embodiment of the present invention provides efficacy against the immune response of specific T cells.

To confirm the immune response efficacy of the specific T cells of virus produced in the present invention, ELISPOT (Enzyme-Linked ImmunoSpot, ELISPOT) experimental technique was used. In the present invention, tumor cells and antigen-injected mouse splenocytes were separated to confirm the immune response to each antigen. As a result, it is thought that the ChimAd-HPV virus induces a specific immune response against the HPV E7 protein antigen.

The present invention provides the efficacy of preventing mouse tumor cells with respect to the ChimAd-HPV vaccine composition produced by the above method. In the present invention, to confirm the preventive effect of cervical cancer by human papillomavirus, the virus and TC-1 tumor cells were injected. In the present invention, after injecting the recombinant antigen, tumor cells were injected to confirm the preventive effect on cancer. As a result, it was confirmed that the ChimAd-HPV virus did not generate tumor cells compared to the control group.

Advantageous Effects

As can be seen through the present invention, the present invention can provide an optimal adenoviral vector in the development of a therapeutic agent or vaccine for various diseases. In addition, when the chimeric adenoviral vector constructed in the present invention is infected with host cells for production, it can contribute to productivity improvement by exhibiting superior cell infectivity compared to recombinant HAdV-5 vector-based vaccines. In addition, the chimeric adenovirus of the present invention can overcome existing immunity to HAdV-5 when inoculated into humans. In addition, it is considered that it will be an excellent chimeric adenovirus vector as the immune effectiveness that can more effectively transfer foreign genes is confirmed when developing a preventive or therapeutic vaccine for SARS-coronavirus-2 and human papillomavirus.

DESCRIPTION OF DRAWINGS

FIG. 1 shows the results of sequence analysis of the amino acid sequences of the fiber proteins of HAdV-5 and ChAdV-6 in the present invention through Clustal Omega and ESPript programs (A) and a schematic diagram of the fiber proteins of the chimeric adenovirus vector (B), FIG. 2 shows the results of sequence analysis of the amino acid sequences of the hexon proteins of HAdV-5 and HAdV-28 in the present invention through Clustal Omega and ESPript programs (A) and a schematic diagram of the hexon proteins of the chimeric adenovirus vector (B), FIG. 3 schematically shows the sequence of the vector regulator synthetic gene produced in the present invention, FIG. 4 is a schematic diagram showing the HAdV-5 vector construction process in the present invention, FIGS. 5 and 6 are schematic diagrams of the ChimAd vector production process (FIG. 5) and the final ChimAd vector structure (FIG. 6) produced in the present invention.

FIGS. 7 and 8 are schematic diagrams showing the production process of the ChimAd-H28 vector (FIG. 7) and the final structure of the ChimAd-H28 vector (FIG. 8) produced in the present invention, FIG. 9 shows the result of confirming the chimeric capsid gene in the two chimeric adenovirus vectors (ChimAd, ChimAd-H28) prepared in the present invention by amplifying the knob gene (0.5 Kb) of ChAdV-6 and the hexon HVR gene of HAdV-28 (1 Kb) by PCR, separating them on a 0.8% agarose gel, and passing ultraviolet rays through them, FIG. 10 is a photograph at 200× magnification using an optical microscope to show the formation of cytopathic effect (CPE) after induction of transformation in HEK293 cells with the HAdV-5 vector and two types of chimeric adenovirus vectors prepared in the present invention, FIG. 11 shows the expression of hexon (about 108 kDa), fiber (about 61 kDa), and penton (about 68 kDa) proteins through Western blot after HAdV-5 and two kinds of chimeric adenovirus were produced in HEK293 cells, FIG. 12 is a graph showing the number of positive cells infected with adenovirus taken at 200-fold magnification of an optical microscope, counting, and converting to virus titer through immunocytochemistry using an anti-hexon polyclonal antibody 48 hours after infecting HEK293 cells with 0, 5, 10, 25, or 50 MOI virus doses of HAdV-5 and chimeric adenoviruses prepared in the present invention. The X-axis represents the dose of virus infected cells, and the Y-axis represents the HAdV-5, ChimAd, and ChimAd-H28 virus titers according to each virus dose. * indicates the significance level between the HAdV-5 virus and the chimeric adenovirus verified using a paired t-test (* $p<0.05$,  $p<0.01$), FIG. 13** shows the in vitro neutralizing antibody test in HEK293 cells by reacting HAdV-5 and chimeric adenoviruses prepared in the present invention with anti-HAdV-5 polyclonal antibodies, and then measuring the number of adenovirus-infected cells and the measured values are plotted graphically. The X axis represents the dilution factor of the anti-HAdV-5 polyclonal antibody serially diluted from $10^1$ to $10^4$, and the Y axis represents the number of cells infected by HAdV-5, ChimAd and ChimAd-H28 viruses. * indicates the level of significance between the HAdV-5 virus and the chimeric adenovirus verified using a paired t-test (* $p<0.05$,  $p<0.01$, * $p<0.005$, ** $p<0.0005$), FIG. 14 shows the result of in vitro neutralizing antibody test in HEK293 cells by reacting HAdV-5 and chimeric adenoviruses prepared in the present invention with healthy human serum (n=7) and the values expressed as reciprocal numbers by measuring the number of cells infected with adenovirus shown as a dot plot. The X-axis represents the adenovirus reacted with the serum, and the Y-axis represents the adenovirus neutralizing antibody (Ad Nab) titer for 7 human serum samples. The significance level between the HAdV-5 virus, the ChimAd virus, and the ChimAd-H28 virus, verified using a paired t-test, is shown as a P value, FIG. 15 is a schematic diagram of cloning ChimAd-CV and ChimAd-CVN using the Gibson assembly gene synthesis method in a ChimAd vector obtained through gene synthesis, FIG. 16 shows the SARS-Coronavirus-2 S protein results (A) and beta variant S protein results (B) for virus-binding antibody titers induced by ChimAd-CV and ChimAd-CVN using BALB/c female mice, FIG. 17** shows the neutralizing antibody titers induced by ChimAd-CV and ChimAd-CVN in BALB/c female mice as neutralizing antibody measurement results (A, B) using a beta variant (B.1.351 variant type) pseudovirus.

FIG. 18 shows the results of cellular immunization (A, B) using S peptides of ChimAd-CV and ChimAd-CVN as stimulating antigens and the results of cellular immunization (C, D) using NP peptides as stimulating antigens, using BALB/c female mice, FIG. 19 shows the results of S protein of SARS-coronavirus-2 (A) and the S protein of delta variant strain (B) induced by ChimAd-CV and ChimAd-CVN using hACE2 transgenic female mice, FIG. 20 shows the results of neutralizing antibody measurement using FRNT of SARS-coronavirus-2 (A, B) and of the delta variant strain (C,D) as a result of confirming the viral neutralizing antibody titer induced by ChimAd-CV and ChimAd-CVN using hACE2 transgenic female mice, FIG. 21 shows survival rate (A, B) and the average body weight (C,D) after SARS-coronavirus-2 (Wuhan-Hu-1), delta variant (B.1.617.2) challenge test in mouse animal models immunized by ChimAd-CV and ChimAd-CVN using hACE2 transgenic female mice, FIG. 22 shows coronavirus titers detected in the lungs after the challenge test, FIG. 23 is a schematic diagram of cloning ChimAd-HPV by using the Gibson assembly gene synthesis method in a ChimAd vector from a human papillomavirus gene obtained through gene synthesis, FIG. 24 shows the results of cellular immunization (A, B) using the HPV16-type E7 peptide as a stimulating antigen, as a result of ELISPOT, showing the specific T cell immune response to the ChimAd-HPV vaccine candidate.

FIG. 25 shows the results of measuring the size of tumors, after subcutaneously injecting TC-1 cells, a tumor cell line, into C57BL/6 mice, and vaccine candidates, including a control group were injected before and after tumor cell injection to measure the size of cancer over time Results showing the lowest tumor volume in the ChimAd-HPV group (A, B) are shown.

MODE FOR INVENTION

Hereinafter, the present invention will be described in more detail by the following examples. However, the following examples are described with the intention of illustrating the present invention, and the scope of the present invention is not to be construed as being limited by the following examples.

EXAMPLE

Example 1: Gene Synthesis for Construction of Chimeric Adenoviral Vectors 1-1) Synthetizing ChAdV-6 Knob Gene In order to construct a chimeric adenoviral vector by replacing the knob domain at the end of the fiber protein of HAdV-5 with the corresponding gene of ChAdV-6, a non-human adenovirus, genetic homology of the amino acid sequence to the fiber protein of HAdV-5 (Genebank: AY339865.1) and ChAdV-6 (Genebank: AY530877) was analyzed using the Clustal Omega program. Finally, the Clustal Omega results visualized the homology region through ESPript figure (FIG. 1A), and among the knob domains of ChAdV-6 (SEQ ID NO: 1), a base sequence corresponding to 405 to 574 amino acids (SEQ ID NO: 1), which is a region with low homology to the gene sequence of HAdV-5, was obtained by gene synthesis. (FIG. 1B, SEQ ID NO: 2).

1-2) Synthetizing HAdV-28 Hypervariable Region (HVR) Gene

To construct a chimeric adenovirus vector by replacing the hypervariable region in the hexon protein of HAdV-5 with the corresponding gene of HAdV-28, an adenovirus serotype with low seroprevalence in humans, genetic homology of the amino acid sequence to the hexon protein of HAdV-5 (Genebank: AY339865.1) and HAdV-28 (Genebank: DQ149626.1) were analyzed using the Clustal Omega program. Finally, the Clustal Omega results were visualized through the ESPript figure, and the HVR1 region to the HVR7 region with low genetic homology of amino acid sequences between HAdV-5 and HAdV-28 were set (Table 1, FIG. 2A). Subsequently, to replace the HVR region in the hexon protein of HAdV-5 with the corresponding gene of HAdV-28, the nucleotide sequence from the beginning of the HVR1 region of HAdV-28 (132 amino acids) to the end of the HVR7 region (449 amino acids) was gene synthesized. (FIG. 2B, SEQ ID NO: 4). the genetic homology of amino acid sequences between HAdV-5 and HAdV-28 was set from the HVR1 region to the HVR7 region (Table 1, FIG. 2A). Subsequently, to replace the HVR region in the hexon protein of HAdV-5 with the corresponding gene of HAdV-28, the nucleotide sequence from the beginning of the HVR1 region of HAdV-28 to the end of the HVR7 region was gene synthesized. (FIG. 2B, SEQ ID NO: 4).

TABLE 1

| Target | HVR region | Position | Sequence |
|---|---|---|---|
| HAdV-5 | HVR1 | 132-168 | PCEWDEAATALEINLEEEDDDNEDEV DEQAEQQKTHV (SEQ ID NO: 15) |
| | HVR2 | 188-195 | VEGQTPKY (SEQ ID NO: 16) |
| | HVR3 | 209-220 | SQWYETEINHAA (SEQ ID NO: 17) |
| | HVR4 | 248-265 | GILVKQQNGKLESQVEMQ (SEQ ID NO: 18) |
| | HVR5 | 268-284 | STTEATAGNGDNLTPKV (SEQ ID NO: 19) |
| | HVR6 | 305-316 | TIKEGNSRELMG (SEQ ID NO: 20) |
| | HVR7 | 418-458 | GGVINTETLTKVKPKTGQENGWEKDA TEFSDKNEIRVGNNF (SEQ ID NO: 21) |
| HAdV-28 | HVR1 | 132-153 | SSQWDAQEKSGQGSDMVTKTHT (SEQ ID NO: 22) |
| | HVR2 | 173-185 | TEITADNQKKEIF (SEQ ID NO: 23) |

TABLE 1-continued

| Target | HVR region | Position | Sequence |
|---|---|---|---|
| | HVR3 | 199-209 | ENWQENEVFYG (SEQ ID NO: 24) |
| | HVR4 | 237-256 | AKFKTPAEGQEPKELDIDLA (SEQ ID NO: 25) |
| | HVR5 | 259-273 | DTDGGTADTEYKADI (SEQ ID NO: 26) |
| | HVR6 | 294-305 | GKEDDSSEINLV (SEQ ID NO: 27) |
| | HVR7 | 407-449 | DGLGTNATYQGVKVSTGDGATQSGWA KDDTMARQNQICRGNIY (SEQ ID NO: 28) |

Table 1 shows HVR regions selected through nucleotide sequence analysis between HAdV-5 and HAdV-28.

1-3) Synthesis of Vector Regulators

Vector regulators to be inserted into the chimeric adenovirus vector were synthesized by combining vector regulators known to date (e.g., promoter, origin of replication, etc.). In more detail, corresponding vector regulators were obtained by synthesizing genes in the order of ITR (inverted terminal repeat, Genebank: AY339865.1), BR322 origin of replication (Genebank: MT612434.1), kanamycin resistance gene (Genebank: MT084773.1), ITR sequence, encapsidation signal, Genebank: AY339865.1), CMV enhancer (Genebank: MT267310.1), CMV promoter (Genebank: MT267310.1), and SV40 poly(A) (Genebank: MT612432.1) (FIG. 3).

Example 2: Preparation of Chimeric Adenoviral Vectors 2-1) Preparing HAdV-5 Vector Using DNA of HAdV-5 (ATCC, VR-1516) as a template, PCR amplification was performed using primers except for some of the E1 and E3 genes to obtain the amplified products (fragments A-G) (Table 2). The synthetic gene (4.1 Kb) comprising the 7 vector PCR amplification products and the synthesized CMV promoter sequence has the same sequence (about 20 bp) at each end, and were combined through a gibson assembly (NEB, E2611S) reaction to construct HAdV-5 vectors (FIG. 4). A ChimAd vector was constructed using this as a basic vector.

TABLE 2

| Primer name | Sequence (5' to 3' direction) | PCR product |
|---|---|---|
| Fragment A | F: TAAGGGTGGGAAAGAATATATAAGGTGGGGGTC (SEQ ID NO: 29)<br>R: GCC TTC CAT CAA GGG CAT CCC G (SEQ ID NO: 30) | 4 Kb |
| Fragment B | F: GTAAAGTTCCAAGAAGCGCGGGATGC (SEQ ID NO: 31)<br>R: AGTTAATCTCCTGGTTCACCGTCTG (SEQ ID NO: 32) | 4 Kb |
| Fragment C | F: GTAACCGCATACGAGCAGACGGTG (SEQ ID NO: 33)<br>R: CGTGGAGCGGAAGGTCACG (SEQ ID NO: 34) | 4 Kb |
| Fragment D | F: GCCAGACATGATGCAAGACCCCGTG (SEQ ID NO: 35)<br>R: CGTACCACTGAGATTCTCCTATTTGAGGTTC (SEQ ID NO: 36) | 4 Kb |
| Fragment E | F: CAACCTGAACCTCAAATAGGAGAATCTCAG (SEQ ID NO: 37)<br>R: GGATAACGATCTAAAGGCGAACTTCAAAC (SEQ ID NO: 38) | 4 Kb |

TABLE 2-continued

| Primer name | Sequence (5' to 3' direction) | PCR product |
|---|---|---|
| Fragment F | F: GTCAGGCAGTAGTTTGAAGTTCGC (SEQ ID NO: 39)<br>R: CTCTAGTTATAACTAGAGGATCTTGATGTAATCCAGGGTTAG (SEQ ID NO: 40) | 4.7 Kb |
| Fragment G | F: CCTCTAGTTATAACTAGAGTACCCGGGATCTTATTCCCTTTAAC (SEQ ID NO: 41)<br>R: CGGAGTAACTTGTATGTGTTGGGAATTG (SEQ ID NO: 42) | 5 Kb |
| Gene synthesis (promoter, etc.) | F: CAATTCCCAACACATACAAGTTACTCCG (SEQ ID NO: 43)<br>R: TATATTCTTTCCCACCCTTACGCGTTAAGATACATTGATG (SEQ ID NO: 44) | 5 Kb |

Table 2 shows PCR primers used to construct HAdV-5 vector 2-2) Preparation of ChimAd Vector A vector PCR amplification product was obtained by PCR amplification using the HAdV-5 vector prepared above as a template and using the primers shown in Table 3, excluding the knob gene sequence. The synthesized ChAdV-6 knob gene was PCR amplified to have the same sequence (about 20 bp) as the vector PCR amplification product at the 3' and 5' ends to obtain an insert gene, and was combined with the vector PCR amplification product through gibson assembly reaction to construct a ChimAd vector (FIGS. 5 and 6).

TABLE 3

| Primer name | Sequence (5' to 3' direction) | PCR product |
|---|---|---|
| 6Knob vector | F: CCTTTGCTACCAACTCATTCTCTTTTTCATACATTGCCC (SEQ ID NO: 45)<br>R: ACAATTAGGGCTTGGGTCAGGTGTGGTCCACAAAGTTAGC (SEQ ID NO: 46) | 33.4 Kb |
| 6Knob insert | F: GCTAACTTTGTGGACCACACCTGACCCAAGCCCTAATTGT (SEQ ID NO: 47)<br>R: GGGCAATGTATGAAAAAGAGAATGAGTTGGTAGCAAAGG (SEQ ID NO: 48) | 0.5 Kb |

Table 3 shows the PCR primers used to amplify the vector and the knob gene for the construction of the ChimAd vector 2-3) Preparation of the ChimAd-H28 Vector Using the ChimAd vector as a template, the vector sequence excluding the HVR region (19,879-20,858 bp) of HAdV-5 was PCR amplified using the primers in Table 4 by PCR, and the amplified product (32.9 Kb) and the PCR amplified product of the HVR sequences of HAdV-28 (1 Kb) synthesized above were combined through Gibson assembly reaction to construct a ChimAd-H28 vector (FIGS. 7 and 8).

TABLE 4

| Primer name | Sequence (5' to 3' direction) | PCR product |
|---|---|---|
| 28HVR vector | F: TGCAGGGGTAACATCTACGCCATGGAAATCAATCTAAATG (SEQ ID NO: 49)<br>R: TGCGCATCCCACTGACTGGAATTTGGGGCACCCTTGGGAG (SEQ ID NO: 50) | 32.9 Kb |
| 28HVR insert | F: CTCCCAAGGGTGCCCCAAATTCCAGTCAGTGGGATGCGCA (SEQ ID NO: 51)<br>R: CATTTAGATTGATTTCCATGGCGTAGATGTTACCCCTGCA (SEQ ID NO: 52) | 1 Kb |

Table 4 shows the PCR primers used to amplify the vector and the 28-type hexon HVR gene for the construction of the ChimAd-H28 vector.

As shown in FIG. 9, only the ChAdV-6 knob gene inserted in 0.5 Kb is amplified in the ChimAd vector by the PCR method, In the ChimAd-H28 vector using this as a template, the amplification of the ChAdV-6 knob gene and the 1 Kb HAdV-28 hexon HVR gene were simultaneously confirmed. Through this, two final chimeric adenoviral vectors (ChimAd, ChimAd-H28) were obtained by confirming the presence or absence of the chimeric capsid gene in the HAdV-5 vector.

Example 3: Production of Adenovirus

To evaluate the virus formation of HAdV-5 and the two chimeric adenoviruses designed and produced in the present invention, each vector was cut and removed from the pBR322 replication start point and kanamycin resistance gene sequence unnecessary for adenovirus formation using Pac I restriction enzyme, and HEK293 cells (human embryonic kidney; ATCC, CRL-1573) expressing E1 and E3 genes subcultured the previous day at $1.6\times10^6$ cells in a 100 mm cell culture dish were transformed using Lipofectamine 2000 (Invitrogen, #11668027).

Transformed cells were cultured for 10-20 days in an incubator maintained at 37° C. and 5.0% $CO_2$ partial pressure, and the formation of a cytopathic effect by adenovirus infection was monitored (FIG. 10). To harvest HAdV-5 and two chimeric adenoviruses from whole CPE, the cells attached to the bottom of the flask were detached using a scraper, and the supernatant was removed by centrifugation at 4 °C and 500×g together with the culture medium, and after washing with 1×PBS, adenovirus was released by repeating the freezing-thawing process three times in the resulting pellet. Cell debris was centrifuged at 14,000×g at room temperature, and the adenovirus-containing supernatant was dispensed into 1.5 mL microcentrifuge tubes and stored at −80 °C.

As shown in FIG. 10, the formation of CPE by transformation in HEK293 cells using the HAdV-5, ChimAd, and ChimAd-H28 vectors prepared in the present invention was confirmed at 200× magnification through an optical microscope. From these results, it is considered that adenovirus replication was achieved in the host cell by the three vectors constructed above, and cytotoxicity was induced by the virus propagation or the expressed adenovirus protein.

Example 4: Western Blot Analysis for Confirming Adenovirus Envelope Protein

To confirm the expression of adenoviral structural proteins for HAdV-5 and chimeric adenoviruses produced in the HEK293 cell line, Western blot analysis was performed as follows. After adding SDS-PAGE loading dye to HAdV-5, ChimAd, and ChimAd-H28 viruses and bathing at 100 °C for 15 minutes, and were separated by electrophoresis on 10% SDS-PAGE at 100 V, and then transferred to a PVDF membrane. After removing the activity of the PVDF membrane with 5% skim milk solution, the primary antibody, anti-HAdV-5 polyclonal antibody (Abcam, #ab6982) was diluted 1:1000 with TBS solution and reacted at room temperature for 1 hour. After washing three times with TBS-T buffer solution, the secondary antibody, HRP-attached goat-derived anti-mouse immunoglobulin G was diluted 1:5000 with TBS solution, reacted at room temperature for 1 hour, and then washed with TBS-T buffer solution repeatedly. Confirmation of Western results was confirmed after color development using diaminobenzidine (Sigma, #34002) (FIG. 11).

As shown in FIG. 11, in HAdV-5, ChimAd and ChimAd-H28 viruses, In the virus, hexon (about 108 kDa), fiber (about 61 kDa), and penton (about 68 kDa) proteins were detected in response to all anti-HAdV-5 polyclonal antibodies specifically. When comparing the detected fiber protein of the HAdV-5 virus and the detected fiber protein of the ChimAd virus, since fiber proteins of the same size were confirmed in ChimAd virus, it can be seen that the chimAd virus knob protein replaced with the ChAdV-6 knob gene was normally expressed. In addition, hexon protein of the same size was confirmed in HAdV-5 and ChimAd-H28, indicating that the hexon protein of the ChimAd-H28 virus replaced with the HVR gene of HAdV-28 was normally expressed. In addition, it can be confirmed that the main coat proteins (hexon, fiber, and penton) of adenovirus are stably expressed by the two chimeric adenovirus vectors.

Example 5: Analysis of Adenovirus Infectivity in HEK293 Cells

To analyze the cell infectivity of two chimeric adenoviruses in which the knob protein sequence that binds to the CAR receptor of the host cell and acts on cell entry is replaced with the gene sequence of ChAdV-6, cells infected with HAdV-5, ChimAd and ChimAd-H28 viruses were observed under the same MOI virus dose condition.

Adenovirus infection titer was measured using the QuickTiter™ titer immunoassay kit (Cell biolabs, #VPK-109) of immunocytochemistry using an anti-hexon polyclonal antibody that binds to adenovirus hexon protein. The adenovirus to be used for titer measurement was diluted from $10^1$ to $10^6$ by 10-fold serial dilution using 1×PBS, and infection was induced by dispensing 100 μl of adenovirus dilution into HEK293 cells in a 24-well plate (SPL, #30024) prepared with a cell count of $2.5\times10^5$ by subculture 1 hour before. Immunostaining for detection of adenovirus was performed 48 hours after infection in an incubator maintained at a temperature of 37° C. and a partial pressure of $CO_2$ of 5.0%. Cells infected for 48 hours were fixed by removing the supernatant, dispensing cold methanol, and leaving the cells at −20° C. for 20 minutes. After sufficiently removing methanol from the fixed cells with 1×PBS solution, the activity was inhibited with 1% skim milk (Difco, #232100) solution, and the primary antibody, anti-hexon antibody, was diluted with 1×PBS and reacted at room temperature for 1 hour. After washing three times with 1×PBS, the HRP-conjugated secondary antibody was diluted to 1× and reacted. Then, using 3.3'-diaminobenzidine stain kit (DAB) (Thermo Fisher, #34002), color was developed for 10 minutes, and then, using an optical microscope, after select the virus dilution interval in which brown spots, which are positive cells infected with adenovirus, are observed between 50 and 100, the infection titer (pfu/mL) of HAdV-5, ChimAd and ChimAd-H28 viruses was measured by applying the adenovirus titer conversion formula provided by Cell Biolabs.

For the infectivity analysis, HEK293 cells subcultured in a 24-well plate at $2.5\times10^5$ cells were incubated for 1 hour in an incubator at a temperature of 37° C. and a $CO_2$ partial pressure of 5.0%, and then based on the pfu/mL value obtained from the virus titer measurement, HAdV-5 and chimeric adenoviruses were diluted with 1×PBS at 0, 5, 10, 25, and 50 MOI virus doses, respectively, to induce infection in the cells. 48 hours after infection, the number of adenovirus-infected cells at each MOI virus dose was counted in at least 4 fields at 200× magnification under an optical microscope through immunocytochemical staining using an anti-hexonpolyclonal antibody (Table 5), and the number of positive cells (brown spots) was converted into pfu/mL values, and the infectivity of HAdV-5 and chimeric adenoviruses for each MOI virus dose was compared (FIG. 12).

TABLE 5

| | Virus dose (MOI) | | | |
|---|---|---|---|---|
| Ad infected cell spots | 5 | 10 | 25 | 50 |
| HAdV-5 | 4.0 | 8.1 | 16.6 | 22.2 |
| ChimAd | 10.1 | 17.9 | 21.6 | 34.6 |
| ChimAd-H28 | 9.5 | 17.7 | 19.8 | 32.3 |

Table 5 shows the number of cells infected by HAdV-5 and chimeric adenovirus at the same MOI. As shown in Table 5, when HEK293 cells were infected with the same time and MOI virus dose, the number of cells infected with ChimAd and ChimAd-H28 viruses was higher than that of HAdV-5 virus.

In addition, when comparing the virus titers for each MOI virus dose in FIG. 12, the ChimAd virus and ChimAd-H28 virus had 1.3-3 times and 1-2 times more virus titers than HAdV-5 virus, respectively. showed a scientifically significant difference. Through these results, it was confirmed that not only cell infectivity but also virus productivity was increased due to replacement of the ChAdV-6 knob gene and the HAdV-28 hexon HVR gene.

Example 6: In Vitro Neutralizing Antibody Test Using Anti-HAdV-5 Polyclonal Antibody To evaluate the existing immune evasion ability of the HAdV-5 vector due to replacement of the knob gene and HVR region of hexon, which is the main neutralizing antibody recognition site, in the two chimeric adenoviruses produced, an in vitro neutralizing antibody test was performed using an anti-HAdV-5 polyclonal antibody (Abcam, #ab6982) as a neutralizing antibody against HAdV-5.

In the in vitro neutralizing antibody test, the anti-HAdV-5 antibody was diluted using 1×PBS solution to a 10-4 dilution factor through serial dilution, and after neutralizing with $1.25\times10^7$ VP of HAdV-5, ChimAd, and ChimAd-H28 viruses corresponding to a 50 MOI virus dose for 1 hour at room temperature, $2.5\times10^5$ cells were dispensed into HEK293 cells in a prepared 24-well cell culture plate, respectively and cultured in an incubator maintained at a temperature of 37 °C and a $CO_2$ partial pressure of 5.0%, and viral infection was induced for 48 hours. 48 hours after infection, immunocytochemical staining using an anti-hexon polyclonal antibody was performed, and by counting the number of positive cells infected with HAdV-5, ChimAd and ChimAd-H28 viruses in at least 4 fields at 200× magnification using an optical microscope for each anti-HAdV-5 polyclonal antibody dilution factor ($10^1$-$10^4$), the ability to avoid neutralization against anti-HAdV-5 antibodies was analyzed (Table 6).

TABLE 6

| | Dilution of anti-HAdV-5 antibody | | | |
|---|---|---|---|---|
| Ad infected cell spots | $10^1$ | $10^2$ | $10^3$ | $10^4$ |
| HAdV-5 | 1.0 | 12.5 | 44.1 | 57.8 |
| ChimAd | 4.4 | 40.1 | 97.0 | 100.8 |
| ChimAd-H28 | 2.6 | 13.5 | 69.5 | 100.1 |

Table 6 shows the number of cells infected with HAdV-5 and chimeric adenovirus after reaction with anti-HAdV-5 polyclonal antibody. As shown in FIG. 13, compared to the HAdV-5 virus, by ChimAd virus about 3.1 to about 4.5 times at low antibody dilution factor ($10^1$-$10^2$) and about 1.8 to about 2.2 times more adenovirus-infected cells at high antibody dilution factor ($10^3$ to $10^4$). ChimAd-H28 virus also confirmed about 2.8 times more adenovirus-infected cells than HAdV-5 virus at a low antibody dilution factor and about 1.5 to about 1.7 times at a high antibody dilution factor, indicating a statistically significant difference. Through this, it was obtained that the neutralizing antibody reaction can be avoided up to 4.5 times only by replacing the knob gene in the adenovirus capsid protein. In addition, the above results are 2 times higher avoidance activity than the result of in vitro neutralizing antibody test of a chimeric adenoviral vector (2 fold avoidance compared to HAdV-5 vector) in which the recently developed HAdV-5 structure was replaced with the HAdV-3 knob gene.

As a result, the ChimAd vector constructed in the present invention is considered to be an adenoviral vector with superior immune evasion ability against HAdV-5 than conventional chimeric adenoviral vectors.

Example 7: In Vitro Neutralizing Antibody Test Using Human Serum

To evaluate the neutralizing antibody titer in human serum capable of recognizing ChimAd and ChimAd-H28 viruses, which are the chimeric adenoviral vectors constructed in the present invention, an in vitro neutralizing antibody test was conducted using the serum of 7 healthy adults. The complement cascade was inactivated in human serum by heat-inactivation at 56 °C, for 30 minutes, and then serially diluted two-fold with 1×PBS. Thereafter, the inactivated sera were neutralized with adenovirus under the same 50 MOI virus dose condition at room temperature for 1 hour, and then through the in vitro neutralizing antibody test method described in Example 6, the number of positive cells (brown spots) was measured in at least four fields at 200× magnification using an optical microscope and expressed as an average to determine whether HAdV-5 and chimeric adenoviruses were infected in HEK293 cells on day 2 of infection (Table 7). The number of stained cells was converted into a reciprocal number and then multiplied by 100 to derive neutralizing antibody titers for HAdV-5, ChimAd, and ChimAd-H28 viruses in human serum, and expressed as a dot plot (FIG. 14).

TABLE 7

| Ad infected | Human serum (N = 7) | | | | | | |
|---|---|---|---|---|---|---|---|
| cell spots | #1 | #2 | #3 | #4 | #5 | #6 | #7 |
| HAdV-5 | 18.5 | 14.4 | 1.4 | 8.6 | 19.25 | 11.4 | 8.6 |
| ChimAd | 45.2 | 50.8 | 23.2 | 22 | 39 | 31.2 | 22 |
| ChimAd-H28 | 44 | 44 | 6 | 27.2 | 43.6 | 27.6 | 23.8 |

Table 7 shows the number of cells infected by HAdV-5 and the chimeric adenovirus following reaction with human sera. As can be seen in Table 7, in the seven human serogroups, we identified cells infected on average 4.6 times more by ChimAd virus than by HAdV-5 virus and by average 2.9 times more cells infected by ChimAd-H28 virus than by HAdV-5 virus, which was a statistically significant difference. In addition, as can be seen in FIG. 13, which shows the number of stained cells as the reciprocal number, it can be seen that the average 2.6-2.7 times lower Ad neutralizing antibody (NAb) titer in the ChimAd virus than in the HAdV-5 virus. These results indicate that vector immunity is lower when administering ChimAd vector-based or ChimAd-H28 vector-based vaccines to humans than HAdV-5 vector-based vaccines, so it will be an optimal adenoviral vector that can deliver foreign genes more efficiently.

Example 8: Application of ChimAd Vector-Based Corona Vaccine 8-1) Genetic Modification Encoding SARS-COV-2 S Protein and N Protein To develop a vaccine using the coronavirus structural protein, two S polypeptide synthetic genes comprising NTD and CTD of Spike protein and N protein including modifications such as amino acid substitution were obtained.

Specifically, in the case of the CV gene, SARS-Coronavirus-2 of the beta-variant S protein was introduced with glycine at 614, acidic amino acid substitution of residues 682 to 685, and consecutive proline substitution mutations at 986 and 987. [Pallesen, Jesper, et al. Proceedings of the National Academy of Sciences 114.35 (2017): E7348-E7357. Bangaru, Sandhya, et al. Science 370.6520 (2020): 1089-1094. Plante, Jessica A., et al. Nature 592.7852 (2021): 116-121.].

In the case of the CVN gene, positions 44 to 180 and 247 to 364 of the N protein were linked to the N-terminus and C-terminus of the Spike protein through a (GGGGS) 3 linker, respectively, and at this time, additional structure prediction was performed through prediction tools such as trRosetta and Alphafold. [Du, Zongyang, et al. Nature Protocols (2021): 1-18. Jumper, John, et al. Nature 596.7873 (2021): 583-589.]

8-2) Gene Synthesis to be Used as SARS-COV-2 Vaccine Material

To develop a vaccine using coronavirus structural proteins, synthetic genes encoding Spike and Nucleocapsid proteins among structural proteins were obtained. As shown in Table 8, for each vaccine candidate, S protein derived from coronavirus B.1.351 and N protein derived from Wuhan-Hu-1 were selected and codon optimized for easy expression in adenovirus. The region comprising the S protein was named CV, and the chimera form in which a portion of the N protein and the S protein were fused was named CVN.

TABLE 8

| | Region | Accession no. |
|---|---|---|
| CV | Spike surface glycoprotein | QUT64557(B.1.351) |
| CVN | NP(NTD)-Spike-NP(CTD) | QUT64557(B.1.351), MN908947(Wuhan-Hu-1) |

8-3) Cloning Chimeric Adenovirus Comprising SARS-COV-2 Gene

In order to clone the two SARS-COV-2 vaccine antigens synthesized above into the ChimAd vector, which is a chimeric adenovirus vector, using the plasmid DNA of the ChimAd vector as a template, PCR amplification was performed except for a part of the GOI binding region gene, and the amplified product (about 33.4 Kb) was purified through gel extraction. The insertion gene for cloning was PCR amplified to comprise the same sequence (homologous region, about 20 bp) as the 5' and 3' ends of the GOI binding region in the ChimAd vector, and the amplification product CV (about 3.8 Kb) and CVN (about 4.7 Kb) were obtained, and then combined with the previously purified DNA PCR amplification products through a gibson assembly reaction, respectively, to finally obtain two types of ChimAd-CV and ChimAd-CVN plasmids (FIG. 15).

TABLE 9

| Primer name | Sequence (5' to 3' direction) | PCR product |
|---|---|---|
| ChimAd vector | F: CTAAGCTTCTAGATAAGATATCCGATCCAC (SEQ ID NO: 53)<br>R: CGCGTCGACGGTACCAGATCTCTAGCGGATC (SEQ ID NO: 54) | 33.4 Kb |
| CV region | F: GATCTGGTACCGTCGACGCGATGTTTGTGTT TCTGGTGCTG (SEQ ID NO: 55)<br>R: TATCTTATCTAGAAGCTTAGTCAGGTATAGTGCA GTTTCAC (SEQ ID NO: 56) | 3.8 Kb |
| CVN region | F: GATCTGGTACCGTCGACGCGATGGGCCTGCC CAACAACAC (SEQ ID NO: 57)<br>R: TATCTTATCTAGAAGCTTAGTCAGGGGAAGGTCT TGTAGGC (SEQ ID NO: 58) | 4.7 Kb |

8-4) Production and Purification of Chimeric Adenovirus-Based Corona Vaccine Candidate To produce a chimeric adenovirus-based coronavirus vaccine candidate using the ChimAd-CV and ChimAd-CVN plasmids produced in the present invention, each plasmid was treated with Pac I restriction enzyme (NEB, R0547L) to cut and remove the pBR322 replication start point and kanamycin resistance gene sequence that are unnecessary for adenovirus formation, and HEK293 cells were transformed with Lipofectamine 2000 (Invitrogen, 11668027) and cultured for 10-20 days in an incubator at 37 °C and $CO_2$ partial pressure of 5.0% to obtain a primary virus stock.

ChimAd-CV and ChimAd-CVN virus production was performed by infecting HEK293 cells at a cell density of about $1\times10^6$ cells/ml with a titer of 2 MOI using the primary virus stock obtained above, and after 48 hours, 0.45 μm CFF microfiltration filter (Cytiva, CFP-4-E-6A) was used to enrich the cells. The recovered cells were treated with 0.5% Tween20 (Sigma-aldrich, P2287-500ML) and 20 U/ml benzonase (Milipore, E1014-25KU) for 4 hours to induce cell lysis and host cell DNA degradation. Thereafter, cell debris was removed using 2 μm and 0.6 μm ULTA GF filters (Cytiva, KGF-A-0210TT, KGF-A-9606TT), and virus concentration and buffer exchange were performed through tangential flow filtration (TFF). ChimAd-CV and ChimAd-CVN virus were isolated from virus samples in PBS buffer through anion exchange chromatography using a HiTrap Capto Q ImpRes column (Cytiva, 17547051) and fast protein liquid chromatography (FPLC) using a Capto core 700 column (Cytiva, 17548115), and formulated into a vaccine buffer, and finally filtered with a 0.2 μm ULTA GF filter (Cytiva, KGF-A-9610TT) to obtain two vaccine candidates.

8-5) Immunogenicity Test Results Through Binding Antibody Titer/Neutralizing Antibody Titer/Cellular Immunity Analysis (1) Immune Induction Using BALB/c Female Mice were immunized using the ChimAd-CV and ChimAd-CVN vaccine candidates obtained by the above manufacturing method. The test group includes a total of 4 groups: buffer, ChimAd used as a mock-up, ChimAd-CV, and ChimAd-CVN. For the immune induction test, 5-week-old BALB/c female mice were used, and each adenovirus test group was injected at a concentration of 2.5*10^9 ifu/dose. At 4-week intervals, the first and second vaccinations were administered by intramuscular injection twice (days 0 and 28), and blood was collected 4 and 6 weeks after the first vaccination (days 27 and 42), serum was separated and the spleen was removed.

(2) ELISA; Binding Antibody Titer of Mouse Anti-Serum by ChimAd-CV and ChimAd-CVN A binding antibody titer test was performed to confirm the presence of antibodies in the serum through a mouse immunity induction test. To perform the test, coronavirus SARS-coronavirus-2 and beta variant S protein were dispensed into microplates at a concentration of 1 μg/ml, 100 ng/well each, and coated at 4 °C for more than 16 hours. After reaction, the plate was washed at least 4 times with 1×PBS comprising Tween 20 (PBS-T) and 100 μl of 0.5% casein was dispensed and reacted at 37 °C for 1 hour. After washing with PBS-T, each serum was diluted 1:100 and then serially diluted 3-fold to approximately $1\times10^6$. After dispensing and reacting at 37 °C for 1 hour, the mixture was washed with PBS-T, and HRP-conjugated Goat anti-mouse IgG HRP (Thermo) was diluted 1:5000 and reacted for 1 hour. After the reaction was completed, to proceed with color development, 50 μl of TMB solution (Thermo) was dispensed and color development was performed for 15-20 minutes. Afterwards, the reaction was stopped by adding an equal amount of Stop solution (Thermo), and the absorbance was measured at a wavelength of 450 nm.

As a result of the binding antibody titer, it was confirmed that all experimental groups inoculated with ChimAd-CV and ChimAd-CVN showed high binding antibody titers of $10^4$ or more to SARS-coronavirus-2 and beta variant strains compared to the control group. In the experimental group inoculated with the control group, binding antibody titers to both SARS-coronavirus-2 and beta variant strains were measured, but the values were confirmed to be invalid (FIG. 16).

(3) pVNT (Pseudovirus Neutralization Test);

Measurement of Neutralizing Antibody Titers Against Pseudoviruses in Mouse Anti-Serum by ChimAd-CV and ChimAd-CVN Neutralizing antibodies in serum were tested through a mouse immune induction test. The pseudovirus system is a virus that uses the backbone of Lentivirus to express the luciferase gene and the Spike protein of SARS-coronavirus-2 or beta variants. In this experiment, Takara's Lenti-X™ Packaging Mix product was used to produce pseudoviruses comprising the Spike protein of SARS-coronavirus-2 and beta variant strains. The produced pseudovirus was transformed into 293T cells overexpressing the ACE2 protein, luciferase expression was quantified and measured, and a neutralizing antibody test was performed using a certain RLU (Relative Light Units) value. For the neutralizing antibody test, each mouse serum was first inactivated at 56 °C for 30 minutes, and DMEM medium comprising 10% FBS was used. The serum was diluted by 1/8 and then serially diluted 2-fold to about $10^3$. Pseudoviruses with a certain RLU value were mixed with the same amount of diluted serum and neutralization reaction was performed at 37 °C and 5% $CO_2$ incubator for 1 time. hACE2-293T cells cultured a day earlier were treated with 100 μl of mixture of the virus and serum and cultured in an incubator at 37 °C and 5% $CO_2$ for about 72 hours. After completion of incubation, about 100 μl of the culture medium was removed, 30 μl of One-Glo luciferase reagent (Promega) was added, and reacted for 3-5 minutes. Then, 60 μl of the mixture was transferred to a white plate and the luminescence value was measured using a luminometer. The measured RLU value was used to calculate the $IC_{50}$ value according to the serum dilution factor using a statistical program.

As shown in Table 10, the results of neutralizing antibodies against the beta variant virus showed $IC_{50}$=1253 for the ChimAd-CV inoculated group and $IC_{50}$=1131 for the ChimAd-CVN inoculated group, which were all higher than $10^3$, confirming a higher neutralizing antibody titer than the negative control group (FIG. 17).

TABLE 10

| | | pVNT(IC50) | |
|---|---|---|---|
| No | Group | 4 wk | 6 wk |
| 1 | PBS | 7 | 42 |
| 2 | ChimAd | 9 | 0 |
| 3 | ChimAd-CV | 244 | 1253 |
| 4 | ChimAd-CVN | 409 | 1131 |

(4) ELISpot; Specific T Cell Immune Response Caused by ChimAd-CV, ChimAd-CVN Adenovirus In the mouse immunity induction test, spleens were removed from each group 4 weeks after the first vaccination and 2 weeks after the second vaccination (6 weeks after the first vaccination). Spleen cells were recovered using Cell strainer (Falcon) and washed with PBS buffer solution. After washing, red blood cells were removed using red blood cell lysis buffer (Sigma), and the number of spleen cells was counted and diluted to the cell concentration used in the test. This experiment used R&D system's mouse IFN-gamma ELISpot kit, and the test was performed according to the manufacturer's instructions. For each test, $1\times10^5$ cells, $2\times10^4$ cells of spleen cells and Genscript's SARS-coronavirus-2 Spike protein peptide pool or Nucleprotein peptide pool were used as stimulating antigens and incubated together for 16 hours in a 37 °C, 5% $CO_2$ incubator. After incubation, the cells were washed with a washing solution, and 100 μl of biotin-conjugated IFN-gamma detection antibody was added and reacted by stirring at room temperature for 2 hours. After the reaction, the cells were washed four times using a washing solution, and 100 μl of streptavidin-AKP (alkaline phosphate) was added and incubated at room temperature for 2 hours. After the final washing, 100 μl of BCIP/NBT substrate was added and reacted at room temperature for about 45 minutes. When color development occurred due to the reaction, the spot was washed with sterilized water, the number of colored spots was counted, and the number of cells in the Spot Forming Unit (SFU) was calculated.

As a result of measuring the induction of specific T-cell immunity to each stimulating antigen of S protein and N protein through the ELISpot test, T-cell immunity was higher after the second vaccination (week 6) than after the first vaccination (week 4). Particularly it was confirmed that a specific immune response to the Spike protein peptide was induced in ChimAd-CVN, which was about two times higher than that in ChimAd-CV. In addition, it was confirmed that ChimAd-CVN induces a specific immune response to Nucleocapsid peptide (FIG. 18).

TABLE 11

| | | SPF/10^6 splenocytes (Spike peptide pool) | |
|---|---|---|---|
| No | Group | 4 wk | 6 wk |
| 1 | PBS | 34 | 17 |
| 2 | ChimAd | 61 | 42 |
| 3 | ChimAd-CV | 2367 | 3824 |
| 4 | ChimAd-CVN | 3020 | 6949 |

8-6) Antibody Titer, Neutralizing Antibody Titer and Challenge Test after ChimAd-CV, ChimAd-CVN Animal Immunization A. Immune Induction and Challenge Test Using hACE2 Transgenic Female Mouse The immune induction and challenge tests conducted at IVI used 6-week-old female human ACE2 transgenic mice (Tg(K18-ACE2)2Prlmn) purchased from Jackson Laboratory (ME, USA). All the above tests were conducted in a BSL-3 level facility within the International Vaccine Research Institute. The immune induction test group includes a total of 4 groups: buffer, ChimAd used as a mock-up, ChimAd-CV, and ChimAd-CVN. Mice were inoculated intramuscularly twice at 4-week intervals, and blood was collected 4 and 6 weeks after the first priming inoculation.

B. ELISA; Measurement of Antibody Titers of Mouse Anti-Serum by ChimAd-CV, ChimAd-CVN After the mouse immune induction test, it was performed to measure the antibody titer in serum. In a 96-well plate, 100 ng/well of SARS-coronavirus-2 S protein and delta variant S protein were dispensed at a concentration of 2 μg/ml and coated at 4 °C for more than 16 hours. After the reaction, 100 μl of PBS containing 1% BSA was dispensed and allowed to react. Each serum was diluted 1:100, then serially diluted 5-fold and reacted at 4 °C for more than 16 hours. HRP-conjugated goat anti-mouse IgG HRP (Southern Biotech) was diluted 1:3000 and reacted at 37 °C for 1 hour. After the reaction was completed, the TMB solution (Millipore) was dispensed to proceed with the color development. Afterwards, the reaction was stopped by adding an equal amount of 0.5 N HCl solution (Merck), and the absorbance was measured at a wavelength of 450 nm.

It was confirmed that both the experimental group inoculated with ChimAd-CV and the experimental group inoculated with ChimAd-CVN showed high binding antibody titers of $10^5$ or more against SARS-coronavirus-2 and delta variant strains compared to the control group (FIG. 19).

C. FRNT (Focus Reduction Neutralization Test); Measurement of Neutralizing Antibody Titers Against Coronavirus in ChimAd-CV and ChimAd-CVN Mouse Anti-Serum After the mouse immune induction test, a test was performed to measure neutralizing antibodies in the serum. For the neutralizing antibody test, each mouse serum was first inactivated at 56 °C for 30 minutes and serially diluted 2-fold using DMEM medium containing 2% FBS. Diluted serum was mixed with $4.5\times10^2$ PFU/25 μl of SARS-coronavirus-2 coronavirus (NCCP #43326 (BetaCoV/Korea/KCDC03/2020) and $4.0\times10^2$ PFU/25 μl of delta variant coronavirus (NCCP #43390 (hCoV-19/Korea119861)/KDCA/2021) and reacted for 30 minutes at 37 °C. After reaction, 50 μl of virus and serum mixture was treated with Vero cells ($1.5\times10^4$ cells/well) cultured one day before and incubated at 37 °C in a $CO_2$ incubator for 4 hours. After 4 hours of reaction, the supernatant was removed, washed with a PBS buffer solution, and 300 μl of 4% formaldehyde solution (Sigma) was added and fixed in a place without light for more than 16 hours. After the reaction, it was washed with PBS. After washing, 100% cold methanol was added and reacted for 10 minutes, followed by reaction at room temperature for 1 hour using blocking solution. Afterwards, it was treated with anti-SARS-COV-2 NP rabbit monoclonal antibody (Sino Biological) diluted 1:3000 and incubated at 37° C. for 1 hour. After incubation, it was washed with a PBS solution containing 0.1% Tween20 (PBS-T), and it was treated with HRP-conjugated goat anti-rabbit IgG (Bio-Rad) diluted 1:2000 and incubated at 37 °C for 1 hour. After washing with PBS-T, the TMB solution was reacted at room temperature for 30 minutes in the absence of light, the reaction was stopped with water, and then dried. For FRNT50 analysis, a Spot reader (Cytation 7 Cell Imaging Multi-Mode Reader) was used, and the value was calculated according to the dilution factor of the serum. The FRNT method is a method of measuring neutralizing antibodies by identifying virus-infected cells by attaching a virus-derived monoclonal antibody to a virus-infected cell and then attaching a secondary antibody labeled with HRP to develop a color as a substrate.

As a result of the neutralizing antibody against the SARS-coronavirus-2 virus, the neutralizing antibody titer can be confirmed as shown in Table, which is more than 100 times higher than the negative control group in both the ChimAd-CV and ChimAd-CVN groups after the first vaccination. After the second vaccination, neutralizing antibody titers were confirmed to be more than 30 times higher in the ChimAd-CV vaccinated group and more than 50 times higher in the ChimAd-CVN vaccinated group.

In addition, as a result of neutralizing antibodies against the delta variant virus, it was confirmed that both the ChimAd-CV vaccinated group and the ChimAd-CVN vaccinated group showed neutralizing antibody titers more than 40 times higher than the negative control group after the second vaccination (FIG. 20).

TABLE 12

| | | SARS-coronavirus-2(FRNT50) | | Delta variant virus (FRNT50) | |
|---|---|---|---|---|---|
| No | Group | 4 wk | 6 wk | 4 wk | 6 wk |
| 1 | PBS | 10 | 10 | 10 | 10 |
| 2 | ChimAd | 10 | 50 | 10 | 26 |
| 3 | ChimAd-CV | 1288 | 1660 | 646 | 1202 |
| 4 | ChimAd-CVN | 1096 | 3020 | 513 | 1096 |

D. Virus Challenge Test after ChimAd-CV, ChimAd-CVN Immunization

The challenge test was intranasal infection with $5\times10^5$ PFU SARS-COV-2 virus (SARS-coronavirus-2, delta variant strain) 4 weeks after boosting vaccination. After vaccination, survival and body weight were monitored daily, and on the 2nd, 4th, and 7th days after infection, blood, lungs, liver, kidneys, and spleen were collected to measure organ weights, and virus titers in the lungs were measured.

As a result of confirming the vaccine protective ability of ChimAd-CV and ChimAd-CVN against SARS-Coronavirus-2 (Wuhan-Hu-1) attack, both survival rates were found to be 100%, and it was confirmed that the ChimAd-CVN vaccinated group did not lose weight and the body weight of the ChimAd-CV vaccinated group was maintained without loss in all but one animal, and that there were individuals whose body weight decreased by more than 10% and then recovered.

In addition, as a result of confirming the vaccine protective ability of ChimAd-CV and ChimAd-CVN against Delta variant attack, ChimAd-CVN showed a survival rate of 40% and average body weight reduction of about 20% after 7 days of infection. Confirmed what was visible. The ChimAd-CV results showed that the survival rate was 100% and the average body weight was maintained at 100% after 7 days of infection (FIG. 21).

E. Lung Virus Titer for ChimAd-CV, ChimAd-CVN Immune Induction and Challenge Test (Plaque Assay)

After the mouse immune induction and challenge test, a plaque assay test was performed to measure the remaining virus titer in the lungs. To measure titer, Vero cells (ATCC, Cat #CCL-81) were used and cultured in an incubator at 37 °C and 5% $CO_2$ for more than 16 hours. The virus isolated from the lungs collected from all groups was stepwise diluted 4-fold up to $10^6$, and 200 μl of the diluted virus was added to the cultured Vero cells and reacted at room temperature for 30 minutes. After reaction, the virus mixture was removed, covered with DMEM (Overlay media) containing 0.8% Agarose and 2% FBS, reacted at room temperature for 15 minutes, and then cultured in a 37 °C, 5% $CO_2$ incubator for 72 hours. After fixation with 10% formalin solution for 1 hour, overlay media was removed, and plaques were stained for 5 minutes using crystal violet (Sigma). To confirm the virus titer, the number of plaques was counted, each dilution factor and the total amount (ml) were calculated to calculate the final titer.

As a result of measuring the residual virus titer in the lungs after the challenge test, in the ChimAd-CV vaccinated group against SARS-coronavirus-2 and delta variant attack, the lung virus titer decreased by more than 20,000 times 2 days after the attack compared to the control group. It was confirmed that the virus was cleared and not measured 4 and 7 days after the attack. It was confirmed that the ChimAd-CVN vaccinated group achieved virus clearance and that the lung virus titer was not measured after 2 days, 4 days, and 7 days (FIG. 22).

Example 9: Application of Chimeric Adenovirus-Based HPV Treatment and Prevention Vaccine 9-1) Genetic Modification Encoding the Proteins of HPV16 Type E6 and E7 and HPV Type 18 E6 and E7 Proteins.

For genetic modification of the anti-carcinogenic protein of HPV type 16, in the case of the E6 protein, a deletion mutation of residues 113 to 122 was induced to inhibit the interaction with carcinogenic proteins caused by the binding domain of the anti-cancer protein p53. In the case of the E7 protein, a deletion mutation of residues 21 to 26 was induced to strongly inhibit the interaction with pRb, the main target, and to suppress the transforming activity ability of E7 itself. In addition, for genetic modification of the anti-cancer protein of HPV type 18, in the case of the E6 protein, a deletion mutation of residues 113 to 122 was induced to inhibit the interaction with carcinogenic proteins caused by the binding domain of the anti-cancer protein p53. In the case of the E7 protein, a deletion mutation of residues 24 to 29 was induced to strongly inhibit the interaction with pRb, the main target, and to suppress the transforming activity ability of E7 itself.

Linear polypeptide (E6E7) in which the amino acids of E6 and E7, tumor proteins derived from human papillomavirus type 16, have been deleted, and linear polypeptide (Linear; E6E7) in which the amino acids of E6 and E7, tumor proteins derived from human papillomavirus type 18, have been deleted. were combined with Linker.

9-2) Chimeric Adenovirus-Based HPV Type 16, Type 18 E6, E7 Gene Synthesis and Chimeric Adenovirus Cloning The E6 and E7 genes, which are anticancer proteins of human papillomavirus types 16 and 18, were modified and synthetic genes encoding these proteins were obtained. For each protein, the strain was selected as shown in Table 13 and the codon was optimized to facilitate expression in HEK cells.

TABLE 13

| | Accession no. |
|---|---|
| HPV 16E6E7 | E6; AAV91660.1, E7; BAO18680.1 |
| HPV 18 E6E7 | E6; 1ADC35716.1, E7; 1ADC35717.1 |

Cloning of the HPV vaccine antigen cloned into the chimeric adenovirus vector was performed in the same manner as the SARS-coronavirus vaccine production (Example 8-3), and finally the ChimAd-HPV plasmid was obtained (FIG. 23).

TABLE 14

| Primer name | Sequence (5' to 3' direction) | PCR product |
|---|---|---|
| ChimAd vector | F: CTAAGCTTCTAGATAAGATATCCGATCCAC (SEQ ID NO: 59)<br>R: CGCGTCGACGGTACCAGATCTCTAGCGGATC (SEQ ID NO: 60) | 33.4 Kb |
| HPV16/18 E6E7 | F: GATCTGGTACCGTCGACGCGATGCACCAGAA GAGAACA (SEQ ID NO: 61)<br>R: TATCTTATCTAGAAGCTTAGTTATTGTTGACTAG CGCACCATGG (SEQ ID NO: 62) | 1.4Kb |

9-3) Immunization Induction Using C57BL/6 Female

Mouse immunization was performed using the ChimAd-HPV vaccine candidate obtained by the above preparing method. The test group includes three groups: buffer, ChimAd used as a mock-up, and ChimAd-HPV. For the immune induction test, 5-week-old C57BL/6 female mice were used, and each adenovirus test group was injected at a concentration of 2*10^7 PFU/ml. At 4-week intervals, the first and second vaccinations were administered by intramuscular injection twice (days 0 and 14), and blood was collected and serum was separated and the spleen was removed at 2 and 4 weeks after the first vaccination (days 14 and 28). In addition, to confirm the effect of treating cervical cancer, $1\times10^5$ TC-1 tumor cells were subcutaneously injected into the flank of 6-week-old C57BL/6 female mice 7 days before the first vaccination, and 6 mice were used for each group. In addition, to confirm the effect of preventing cervical cancer, $1\times10^5$ TC-1 tumor cells were subcutaneously injected into the flanks of 6-week-old C57BL/6 female mice 7 days after the second vaccination, and 6 mice were used in each group.

9-4) ELISPOT; Specific T Cell Immune Response by ChimAd-HPV Adenovirus

On the 35th day after the second vaccination, spleens were removed from each group. The spleen was crushed into small pieces using a Cell strainer (Falcon) and the spleen cells were recovered and washed with a PBS buffer solution. Afterwards, red blood cells were removed using red blood cell lysis buffer (Sigma), and the number of spleen cells was counted and diluted to the number of cells to be used in the test. This experiment used R&D system's mouse IFN-gamma ELISpot kit, and the test was performed according to the manufacturer's instructions.

Then, $2\times10^5$ cells and $4\times10^4$ cells of splenocytes recovered from each mouse and the 49-57 amino acid peptide of Genscript's HPV E7 protein were used as stimulating antigens on a plate coated with mouse IFN-gamma monoclonal antibody and incubated for 16 hours at 37 °C in a 5% $CO_2$ incubator. After incubation, the cells were washed four times using 1× Wash buffer, 100 μl of streptavidin-AKP (alkaline phosphate) was added and incubated at room temperature for 2 hours. After the final washing, 100 μl of BCIP/NBT substrate was added and incubated at room temperature for 45 minutes. When color development due to the reaction appeared, it was washed with sterilized water and the number of colored dots was counted.

As a result of measuring the specific T cell immune response to the HPV E7 protein antigen using ELISPOT, the ChimAd-HPV group showed higher results than the control group, confirming that it induced a specific immune response to the antigen. (FIG. 24)

9-5) Tumor Inhibition Assay; Confirmation of Tumor Treatment and Prevention Effects by ChimAd-HPV Adenovirus To confirm the treatment effect of ChimAd-HPV adenovirus on cervical cancer, $1\times10^5$ TC-1 tumor cells were subcutaneously injected into the flank of 6-week-old C57BL/6 female mice, and 6 mice were used per group. To confirm treatment efficacy, 7 days after injection of TC-1 cells, intramuscular injection of control group and ChimAd-HPV adenovirus was performed, and a second injection was performed on the 21st day after injection of tumor cells. In addition, to confirm the preventive efficacy, control and ChimAd-HPV adenoviruses were injected intramuscularly twice at two-week intervals, and 14 days after the second injection, TC-1 tumor cells ($1\times10^5$ cells) were injected subcutaneously into the flank. Tumor cells were measured every 4-5 days by measuring their longest (length) and shortest dimensions (width) using digital calipers to estimate tumor size in mice. Tumor volume was calculated by the following equation: tumor volume=$(\text{length}\times\text{width}^2)/2$.

As shown in FIG. 24, as a result of measuring the tumor volume using ChimAd-HPV adenovirus, the tumor volume was found to be lower in the ChimAd-HPV adenovirus group compared to the negative control group and positive control group in both therapeutic and preventive efficacy. It was confirmed that no tumor cells occurred in the ChimAd-HPV adenovirus group. (FIG. 25)

[Sequence list pre text]

SEQ ID NO: 1

Chimpanzee adenovirus serotype 6 Fiber knob domain a.a sequence(synthesized ChAdV-6 knob a.a sequences are underlined)

PDPSPNCQLLSDRDAKFTLCLTKCGSQILGTVAVAAVTGSALNPINDTVKSAIVFLR
FDSDGVLMSNSSMVGDYWNFREGQTTQSVAYTNAVGFMPNIGAYPKTQSKTPKNSI
VSQVYLTGETTMPMTLTITFNGTDEKDTTPVSTYSMTFTWQWTGDYKDKNITFATN
SFS

SEQ ID NO: 2

Chimpanzee adenovirus serotype 6/Pan6/Sad23 Fiber knob domain nucleotide sequence CCTGACCCAAGCCCTAATTGTCAATTACTTTCAGACAGAGATGCCAAATTTACTC
TCTGTCTTACAAAATGCGGTAGTCAAATACTAGGCACTGTGGCAGTGGCGGCTGT
TACTGTAGGATCAGCACTAAATCCAATTAATGACACAGTCAAAAGCGCCATAGT
TTTCCTTAGATTTGATTCCGATGGTGTACTCATGTCAAACTCATCAATGGTAGGTG
ATTACTGGAACTTTAGGGAGGGACAGACCACTCAAAGTGTAGCCTATACAAATG
CTGTGGGATTCATGCCAAATATAGGTGCATATCCAAAAACCCAAAGTAAAACAC
CTAAAAATAGCATAGTCAGTCAGGTATATTTAACTGGAGAAACTACTATGCCAAT
GACACTAACCATAACTTTCAATGGCACTGATGAAAAAGACACAACCCCAGTTAG
CACCTACTCTATGACTTTTACATGGCAGTGGACTGGAGACTATAAGGACAAAAAT
ATTACCTTTGCTACCAACTCATTCTCT

SEQ ID NO: 3

Chimeric hexon HVR 1 to 7 region a.a sequence (HAdV-5 hexon + HAdV-28 HVR 1-7 region)

SSQWDAQEKSGQGSDMVTKTHTFGVAAMGGENITKNGLQIGTEITADNQKKEIFAN
KTYQPEPQVGEENWQENEVFYGGRALKKETKMKPCYGSFARPTNENGGQAKFKTP
AEGQEPKELDIDLAFFDTDGGTADTEYKADIVMYAENVNLETPDTHVVYKPGKEDD
SSEINLVQQSMPNRPNYIGFRDNFVGLMYYNSTGNMGVLAGQASQLNAVVDLQDR
NTELSYQLLLDSLGDRTRYFSMWNSAVDSYDPDVRIIENHGVEDELPNYCFPLDGLG
TNATYQGVKVSTGDGATQSGWAKDDTMARQNQICRGNIY

SEQ ID NO: 4

Chimeric hexon HVR 1 to 7 region nucleotide sequence (HAdV-5 hexon + HAdV-28 HVR 1-7 region)

TCCAGTCAGTGGGATGCGCAAGAAAAAAGTGGACAAGGAAGTGACATGG
TTACTAAAACTCACACATTTGGGCAGGCGCCTTATTCTGGTATAAATATTACAAA
GGAGGGTATTCAAATAGGTACTGAAATTACCGCCGACAATCAAAAGAAAGAAAT
TTTTGCCGATAAAACATTTCAACCTGAACCTCAAATAGGAGAAGAGAACTGGCA
AGAAAATGAAGTCTTCTATGGCGGGAGAGTCCTAAAAAAGACTACCCCAATGAA
ACCATGTTACGGTTCATATGCAAAACCCACAAATGAAAATGGAGGGCAAGCAAA
ATTCAAAACACCTGCTGAAGGACAGGAACCTAAAGAACTTGACATTGACCTTGC
TTTTTTCGACACTGACGGCGGAACAGCTGACACTGAATATAAAGCAGATATTGTA
TTGTACAGTGAAGATGTAGATATAGAAACCCCAGACACTCATATTTCTTACATGC
CCGGCAAGGAAGATGACAGTTCAGAAATCAATCTAGTTCAACAATCTATGCCCA
ACAGGCCTAATTACATTGCTTTTAGGGACAATTTTATTGGTCTAATGTATTACAAC
AGCACGGGTAATATGGGTGTTCTGGCGGGCCAAGCATCGCAGTTGAATGCTGTT
GTAGATTTGCAAGACAGAAACACAGAGCTTTCATACCAGCTTTTGCTTGATTCCA
TTGGTGATAGAACCAGGTACTTTTCTATGTGGAATCAGGCTGTTGACAGCTATGA
TCCAGATGTTAGAATTATTGAAAATCATGGAACTGAAGATGAACTTCCAAATTAC
TGCTTTCCACTGGACGGATTGGGAACTAATGCTACCTATCAAGGTGTAAAAGTAT
CAACTGGAGATGGTGCTACGCAAAGCGGATGGGCAAAAGACGACACAATGGCC
AGGCAAAACCAAATATGCAGGGGTAACATCTAC

SEQ ID NO: 5

Chimeric fiber gene sequence (HAdV-5 tail, shift domain + ChAdV-6 knob domain)

ATGAAGCGCGCAAGACCGTCTGAAGATACCTTCAACCCCGTGTATCCATATGAC
ACGGAAACCGGTCCTCCAACTGTGCCTTTTCTTACTCCTCCCTTTGTATCCCCCAA
TGGGTTTCAAGAGAGTCCCCCTGGGGTACTCTCTTTGCGCCTATCCGAACCTCTA
GTTACCTCCAATGGCATGCTTGCGCTCAAAATGGGCAACGGCCTCTCTCTGGACG
AGGCCGGCAACCTTACCTCCCAAAATGTAACCACTGTGAGCCCACCTCTCAAAA
AAACCAAGTCAAACATAAACCTGGAAATATCTGCACCCCTCACAGTTACCTCAG
AAGCCCTAACTGTGGCTGCCGCCGCACCTCTAATGGTCGCGGGCAACACACTCAC
CATGCAATCACAGGCCCCGCTAACCGTGCACGACTCCAAACTTAGCATTGCCACC
CAAGGACCCCTCACAGTGTCAGAAGGAAAGCTAGCCCTGCAAACATCAGGCCCC
CTCACCACCACCGATAGCAGTACCCTTACTATCACTGCCTCACCCCCTCTAACTA
CTGCCACTGGTAGCTTGGGCATTGACTTGAAAGAGCCCATTTATACACAAAATGG
AAAACTAGGACTAAAGTACGGGGCTCCTTTGCATGTAACAGACGACCTAAACAC
TTTGACCGTAGCAACTGGTCCAGGTGTGACTATTAATAATACTTCCTTGCAAACT
AAAGTTACTGGAGCCTTGGGTTTTGATTCACAAGGCAATATGCAACTTAATGTAG
CAGGAGGACTAAGGATTGATTCTCAAAACAGACGCCTTATACTTGATGTTAGTTA
TCCGTTTGATGCTCAAAACCAACTAAATCTAAGACTAGGACAGGGCCCTCTTTTT
ATAAACTCAGCCCACAACTTGGATATTAACTACAACAAAGGCCTTTACTTGTTTA
CAGCTTCAAACAATTCCAAAAAGCTTGAGGTTAACCTAAGCACTGCCAAGGGGT
TGATGTTTGACGCTACAGCCATAGCCATTAATGCAGGAGATGGGCTTGAATTTGG
TTCACCTAATGCACCAAACACAAATCCCCTCAAAACAAAAATTGGCCATGGCCT
AGAATTTGATTCAAACAAGGCTATGGTTCCTAAACTAGGAACTGGCCTTAGTTTT
GACAGCACAGGTGCCATTACAGTAGGAAACAAAAATAATGATAAGCTAACTTTG
TGGACCACACCTGACCCAAGCCCTAATTGTCAATTACTTTCAGACAGAGATGCCA

-continued

AATTTACTCTCTGTCTTACAAAATGCGGTAGTCAAATACTAGGCACTGTGGCAGT
GGCGGCTGTTACTGTAGGATCAGCACTAAATCCAATTAATGACACAGTCAAAAG
CGCCATAGTTTTCCTTAGATTTGATTCCGATGGTGTACTCATGTCAAACTCATCAA
TGGTAGGTGATTACTGGAACTTTAGGGAGGGACAGACCACTCAAAGTGTAGCCT
ATACAAATGCTGTGGGATTCATGCCAAATATAGGTGCATATCCAAAAACCCAAA
GTAAAACACCTAAAAATAGCATAGTCAGTCAGGTATATTTAACTGGAGAAACTA
CTATGCCAATGACACTAACCATAACTTTCAATGGCACTGATGAAAAAGACACAA
CCCCAGTTAGCACCTACTCTATGACTTTTACATGGCAGTGGACTGGAGACTATAA
GGACAAAAATATTACCTTTGCTACCAACTCATTCTCT

SEQ ID NO: 6

Chimeric hexon gene sequence (HAdV-5 hexon + HAdV-28 HVR 1-7region)

ATGGCTACCCCTTCGATGATGCCGCAGTGGTCTTACATGCACATCTCGGGCCAGG
ACGCCTCGGAGTACCTGAGCCCCGGGCTGGTGCAGTTTGCCCGCGCCACCGAGA
CGTACTTCAGCCTGAATAACAAGTTTAGAAACCCCACGGTGGCGCCTACGCACG
ACGTGACCACAGACCGGTCCCAGCGTTTGACGCTGCGGTTCATCCCTGTGGACCG
TGAGGATACTGCGTACTCGTACAAGGCGCGGTTCACCCTAGCTGTGGGTGATAAC
CGTGTGCTGGACATGGCTTCCACGTACTTTGACATCCGCGGCGTGCTGGACAGGG
GCCCTACTTTTAAGCCCTACTCTGGCACTGCCTACAACGCCCTGGCTCCCAAGGG
TGCCCCAAATTCCAGTCAGTGGGATGCGCAAGAAAAAAGTGGACAAGGAAGTGA
CATGGTTACTAAAACTCACACATTTGGGCAGGCGCCTTATTCTGGTATAAATATT
ACAAAGGAGGGTATTCAAATAGGTACTGAAATTACCGCCGACAATCAAAAGAAA
GAAATTTTTGCCGATAAAACATTTCAACCTGAACCTCAAATAGGAGAAGAGAAC
TGGCAAGAAAATGAAGTCTTCTATGGCGGGAGAGTCCTAAAAAAGACTACCCCA
ATGAAACCATGTTACGGTTCATATGCAAAACCCACAAATGAAAATGGAGGGCAA
GCAAAATTCAAAACACCTGCTGAAGGACAGGAACCTAAAGAACTTGACATTGAC
CTTGCTTTTTTCGACACTGACGGCGGAACAGCTGACACTGAATATAAAGCAGATA
TTGTATTGTACAGTGAAGATGTAGATATAGAAACCCCAGACACTCATATTTCTTA
CATGCCCGGCAAGGAAGATGACAGTTCAGAAATCAATCTAGTTCAACAATCTAT
GCCCAACAGGCCTAATTACATTGCTTTTAGGGACAATTTTATTGGTCTAATGTATT
ACAACAGCACGGGTAATATGGGTGTTCTGGCGGGCCAAGCATCGCAGTTGAATG
CTGTTGTAGATTTGCAAGACAGAAACACAGAGCTTTCATACCAGCTTTTGCTTGA
TTCCATTGGTGATAGAACCAGGTACTTTTCTATGTGGAATCAGGCTGTTGACAGC
TATGATCCAGATGTTAGAATTATTGAAAATCATGGAACTGAAGATGAACTTCCAA
ATTACTGCTTTCCACTGGACGGATTGGGAACTAATGCTACCTATCAAGGTGTAAA
AGTATCAACTGGAGATGGTGCTACGCAAAGCGGATGGGCAAAAGACGACACAAT
GGCCAGGCAAAACCAAATATGCAGGGGTAACATCTACGCCATGGAAATCAATCT
AAATGCCAACCTGTGGAGAAATTTCCTGTACTCCAACATAGCGCTGTATTTGCCC
GACAAGCTAAAGTACAGTCCTTCCAACGTAAAAATTTCTGATAACCCAAACACCT
ACGACTACATGAACAAGCGAGTGGTGGCTCCCGGGCTAGTGGACTGCTACATTA
ACCTTGGAGCACGCTGGTCCCTTGACTATATGGACAACGTCAACCCATTTAACCA
CCACCGCAATGCTGGCCTGCGCTACCGCTCAATGTTGCTGGGCAATGGTCGCTAT
GTGCCCTTCCACATCCAGGTGCCTCAGAAGTTCTTTGCCATTAAAAACCTCCTTCT
CCTGCCGGGCTCATACACCTACGAGTGGAACTTCAGGAAGGATGTTAACATGGTT
CTGCAGAGCTCCCTAGGAAATGACCTAAGGGTTGACGGAGCCAGCATTAAGTTT
GATAGCATTTGCCTTTACGCCACCTTCTTCCCCATGGCCCACAACACCGCCTCCA
CGCTTGAGGCCATGCTTAGAAACGACACCAACGACCAGTCCTTTAACGACTATCT
CTCCGCCGCCAACATGCTCTACCCTATACCCGCCAACGCTACCAACGTGCCCATA
TCCATCCCCTCCCGCAACTGGGCGGCTTTCCGCGGCTGGGCCTTCACGCGCCTTA
AGACTAAGGAAACCCCATCACTGGGCTCGGGCTACGACCCTTATTACACCTACTC
TGGCTCTATACCCTACCTAGATGGAACCTTTTACCTCAACCACACCTTTAAGAAG
GTGGCCATTACCTTTGACTCTTCTGTCAGCTGGCCTGGCAATGACCGCCTGCTTAC
CCCCAACGAGTTTGAAATTAAGCGCTCAGTTGACGGGGAGGGTTACAACGTTGC
CCAGTGTAACATGACCAAAGACTGGTTCCTGGTACAAATGCTAGCTAACTATAAC
ATTGGCTACCAGGGCTTCTATATCCCAGAGAGCTACAAGGACCGCATGTACTCCT
TCTTTAGAAACTTCCAGCCCATGAGCCGTCAGGTGGTGGATGATACTAAATACAA
GGACTACCAACAGGTGGGCATCCTACACCAACACAACAACTCTGGATTTGTTGG
CTACCTTGCCCCCACCATGCGCGAAGGACAGGCCTACCCTGCTAACTTCCCCTAT
CCGCTTATAGGCAAGACCGCAGTTGACAGCATTACCCAGAAAAAGTTTCTTTGCG
ATCGCACCCTTTGGCGCATCCCATTCTCCAGTAACTTTATGTCCATGGGCGCACTC
ACAGACCTGGGCCAAAACCTTCTCTACGCCAACTCCGCCCACGCGCTAGACATG
ACTTTTGAGGTGGATCCCATGGACGAGCCCACCCTTCTTTATGTTTTGTTTGAAGT
CTTTGACGTGGTCCGTGTGCACCAGCCGCACCGCGGCGTCATCGAAACCGTGTAC
CTGCGCACGCCCTTCTCGGCCGGCAACGCCACAACATAA

[ChimAd-based coronavirus vaccine sequence]

SEQ ID NO: 7

SARS-COV-2_B.1.351(beta) spike modified amino acid sequence

MFVFLVLLPLVSSQCVNFTTRTQLPPAYTNSFTRGVYYPDKVFRSSVLHSTQDLFLPF
FSNVTWFHAIHVSGTNGTKRFANPVLPFNDGVYFASTEKSNIIRGWIFGTTLDSKTQS
LLIVNNATNVVIKVCEFQFCNDPFLGVYYHKNNKSWMESEFRVYSSANNCTFEYVS
QPFLMDLEGKQGNFKNLREFVFKNIDGYFKIYSKHTPINLVRGLPQGFSALEPLVDLP
IGINITRFQTLHISYLTPGDSSSGWTAGAAAYYVGYLQPRTFLLKYNENGTITDAVDC
ALDPLSETKCTLKSFTVEKGIYQTSNFRVQPTESIVRFPNITNLCPFGEVFNATRFASV
YAWNRKRISNCVADYSVLYNSASFSTFKCYGVSPTKLNDLCFTNVYADSFVIRGDEV
RQIAPGQTGNIADYNYKLPDDFTGCVIAWNSNNLDSKVGGNYNYLYRLFRKSNLKP
FERDISTEIYQAGSTPCNGVKGFNCYFPLQSYGFQPTYGVGYQPYRVVVLSFELLHAP
ATVCGPKKSTNLVKNKCVNFNFNGLTGTGVLTESNKKFLPFQQFGRDIADTTDAVR
DPQTLEILDITPCSFGGVSVITPGTNTSNQVAVLYQGVNCTEVPVAIHADQLTPTWRV
YSTGSNVFQTRAGCLIGAEHVNNSYECDIPIGAGICASYQTQTNSPQQAQSVASQSIIA

-continued

YTMSLGVENSVAYSNNSIAIPTNFTISVTTEILPVSMTKTSVDCTMYICGDSTECSNLL
LQYGSFCTQLNRALTGIAVEQDKNTQEVFAQVKQIYKTPPIKDFGGFNFSQILPDPSK
PSKRSFIEDLLFNKVTLADAGFIKQYGDCLGDIAARDLICAQKFNGLTVLPPLLTDEMI
AQYTSALLAGTITSGWTFGAGAALQIPFAMQMAYRENGIGVTQNVLYENQKLIANQ
FNSAIGKIQDSLSSTASALGKLQDVVNQNAQALNTLVKQLSSNFGAISSVLNDILSRL
DPPEAEVQIDRLITGRLQSLQTYVTQQLIRAAEIRASANLAATKMSECVLGQSKRVDF
CGKGYHLMSFPQSAPHGVVFLHVTYVPAQEKNFTTAPAICHDGKAHFPREGVFVSN
GTHWFVTQRNFYEPQIITTDNTFVSGNCDVVIGIVNNTVYDPLQPELDSFKEELDKYF
KNHTSPDVDLGDISGINASVVNIQKEIDRLNEVAKNLNESLIDLQELGKYEQYIKWPW
YIWLGFIAGLIAIVMVTIMLCCMTSCCSCLKGCCSCGSCCKFDEDDSEPVLKGVKLH
YTSEQ

SEQ ID NO: 8

SARS-COV-2_B.1.351(beta) spike modified nucleic acid sequence
ATG TTT GTG TTT CTG GTG CTG CTG CCT CTG GTG AGC AGC CAG TGC GTG
AAC TTC ACC ACC AGA ACC CAG CTG CCT CCT GCC TAC ACC AAC AGC TTT
ACC AGA GGC GTG TAT TAC CCC GAC AAA GTG TTT AGA TCC TCC GTG CTG CAC
AGC ACC CAG GAC CTG TTT CTG CCC TTT TTC AGC AAC GTG ACC TGG TTC
CAT GCC ATC CAC GTG AGC GGC ACC AAC GGC ACC AAG AGA TTC GCC AAT
CCC GTG CTG CCT TTT AAT GAC GGC GTG TAC TTT GCC AGC ACC GAG AAG
AGC AAT ATC ATC AGA GGC TGG ATC TTC GGC ACC ACC CTG GAT AGC AAG ACC
CAG AGC CTG CTG ATC GTG AAT AAT GCC ACC AAT GTG GTG ATC AAA GTG
TGC GAG TTC CAG TTT TGT AAC GAC CCC TTT CTG GGC GTG TAT TAC CAC
AAG AAC AAC AAA AGC TGG ATG GAG AGC GAA TTC AGA GTG TAC AGC AGC
GCC AAT AAC TGC ACC TTT GAG TAC GTG AGC CAG CCC TTT CTG ATG GAC CTG
GAG GGC AAG CAG GGC AAC TTC AAG AAC CTG AGA GAG TTC GTG TTT AAA
AAT ATC GAC GGC TAC TTC AAG ATC TAC AGC AAG CAT ACA CCC ATC AAC
CTG GTG AGA GGC CTG CCC CAG GGC TTC AGC GCC CTG GAG CCC CTG GTG
GAC CTG CCC ATC GGC ATC AAC ATT ACC CGG TTT CAG ACC CTG CAC AGA
AGC TAT CTG ACC CCC GGC GAC AGC AGC AGC GGC TGG ACC GCC GGA GCC
GCC GCC TAT TAT GTG GGC TAC CTG CAG CCC AGA ACC TTC CTG CTG AAA TAC
AAC GAG AAC GGC ACC ATC ACC GAC GCC GTG G?C TGC GCC CTG GAC CCC
CTG AGC GAG ACC AAG TGT ACC CTG AAG AGC TTT ACC GTG GAG AAG GGC
ATC TAC CAG ACC AGC AAC TTT AGA GTG CAG CCC ACC GAG AGC ATC GTG
AGA TTT CCC AAC ATC ACC AAC CTG TGC CCC TTC GGG GAG GTG TTT AAT
GCC ACC AGA TTC GCC AGC GTG TAC GCC TGG AAT AGA AAA AGA ATC AGC
AAC TGC GTG GCC GAC TAC AGC GTG CTG TAC AAC TCT GCC AGC TTT TCC
ACC TTT AAG TGC TAC GGC GTG AGC CCA ACC AAA CTG AAC GAC CTG TGC TTC
ACC AAC GTG TAC GCC GAC AGC TTC GTG ATC AGA GGC GAC GAG GTG AGA
CAG ATC GCC CCC GGC CAG ACC GGC AAT ATC GCC GAT TAC AAC TAC AAG
CTG CCC GAC GAC TTT ACC GGC TGC GTG ATC GCC TGG AAC AGC AAC AAC
CTG GAC AGC AAG GTG GGC GGC AAC TAC AAC TAC CTG TAC AGA CTG TTT
AGA AAG AGC AAC CTG AAG CCC TTT GAG AGA GAC ATC AGC ACC GAG ATC
TAC CAG GCC GGC AGC ACC CCC TGC AAC GGC GTG AAA GGC TTT AAT TGT
TAC TTC CCA CTG CAG TCC TAC GGC TTC CAG CCT ACC TAC GGC GTG GGA TAT
CAG CCC TAT AGA GTG GTG GTG CTG TCC TTC GAG CTG CTG CAC GCC CCC
GCC ACC GTG TGC GGC CCA AAG AAG AGC ACC AAC CTG GTG AAG AAC AAG
TGC GTG AAC TTC AAC TTC AAC GGC CTG ACC GGC ACC GGC GTG CTG ACC
GAG TCC AAC AAG AAA TTT CTG CCC TTC CAG CAG TTC GGA AGA GAC ATT GCC
GAT ACC ACC GAC GCC GTG AGA GAC CCC CAG ACC CTG GAG ATC CTG GAC
ATC ACC CCC TGT AGC TTC GGC GGC GTG TCC GTG ATC ACC CCA GGC ACC
AAC ACC TCC AAC CAG GTG GCC GTG CTG TAC CAG GGC GTG AAC TGT ACC
GAG GTG CCT GTG GCC ATC CAC GCC GAT CAG CTG ACC CCA ACC TGG AGA
GTG TAC TCC ACC GGC TCC AAC GTG TTC CAG ACC AGA GCC GGC TGT CTG
ATC GGC GCC GAG CAC GTG AAC AAC TCC TAC GAG TGC GAC ATC CCT ATC GGC
GCC GGC ATC TGC GCC AGC TAC CAG ACC CAG ACC AAT AGC CCC CAG
CAG GCC CAG
TCC GTG GCC AGC CAG TCC ATC ATT GCC TAC ACC ATG TCC CTG GGC GTG
GAG AAC AGC GTG GCC TAC TCC AAC AAC AGC ATC GCC ATC CCC ACC AAT TTC
ACC ATC AGC GTG ACC ACC GAA ATC CTG CCA GTG AGC ATG ACC AAA ACC
TCC GTG GAT TGC ACC ATG TAC ATC TGC GGA GAC TCC ACC GAG TGC TCC
AAC CTG CTG CTG CAG TAC GGC TCC TTT TGC ACC CAG CTG AAC AGA GCC
CTG ACC GGA ATC GCC GTG GAG CAG GAT AAA AAC ACC CAG GAA GTG TTC
GCC CAG GTG AAA CAG ATC TAC AAG ACC CCC CCC ATC AAA GAT TTT GGA
GGC TTT AAT TTT AGC CAG ATC CTG CCT GAT CCC TCC AAA CCC AGC AAG AGA
TCC TTT ATC GAG GAT CTG CTG TTC AAC AAA GTG ACA CTG GCC GAT GCC
GGA TTT ATC AAA CAG TAC GGA GAC TGC CTG GGC GAC ATC GCC GCC AGA
GAC CTG ATC TGC GCC CAG AAG TTT AAC GGC CTG ACC GTG CTG CCA CCC
CTG CTG ACC GAC GAG ATG ATC GCC CAG TAT ACC TCC GCC CTG CTG GCC GGC
ACC ATC ACC TCC GGC TGG ACC TTT GGC GCC GGA GCC GCC CTG CAG ATC
CCA TTT GCC ATG CAG ATG GCC TAC AGA TTT AAT GGA ATC GGA GTG ACC
CAG AAC GTG CTG TAT GAG AAC CAG AAA CTG ATC GCC AAT CAG TTC AAC
AGC GCC ATC GGC AAG ATC CAG GAT TCT CTG AGC TCC ACC GCC TCT GCC CTG
GGC AAG CTG CAG GAC GTG GTG AAT CAG AAC GCC CAG GCC CTG AAC ACC
CTG GTG AAA CAG CTG AGC AGC AAC TTT GGC GCC ATC AGC AGC GTG CTG
AAT GAT ATC CTG AGC AGA CTG GAT CCT CCA GAG GCC GAG GTG CAG ATC
GAC AGA CTG ATC ACA GGG AGA CTG CAG AGC CTG CAG ACC TAT GTG ACA
CAG CAG CTG ATC AGA GCC GCC GAA ATT AGA GCC AGC GCC AAC CTG GCC
GCC ACC AAA ATG AGC GAG TGT GTG CTG GGA CAG AGC AAA AGA GTG GAC
TTC TGC GGC AAA GGC TAC CAT CTG ATG AGC TTC CCC CAG AGC GCC CCC
CAC GGC GTG GTG TTC CTG CAT GTG ACC TAC GTG CCC GCC CAG GAA AAA -continued

```
AAT TTT ACC ACC GCC CCT GCC ATC TGT CAC GAC GGC AAA GCC CAT TTT CCC
AGA GAG GGC GTG TTT GTG AGC AAC GGC ACC CAC TGG TTT GTG ACC CAG
AGA AAC TTT TAC GAA CCC CAG ATC ATC ACC ACA GAT AAT ACC TTT GTG
AGC GGA AAT TGT GAT GTG GTG ATC GGC ATC GTG AAT AAT ACC GTG TAT
GAT CCT CTG CAG CCA GAG CTG GAC AGC TTT AAG GAG GAG CTG GAC AAG
GAT TTT AAA AAT CAT ACC AGC CCC GAC GTG GAT CTG GGA GAT ATC AGC GGA
ATC AAC GCC TCC GTG GTG AAT ATC CAG AAG GAG ATC GAC AGA CTG AAC
GAG GTG GCC AAA AAT CTG AAT GAG TCC CTG ATC GAC CTG CAG GAG CTG
GGC AAA TAT GAA CAG TAC ATC AAG TGG CCA TGG TAC ATC TGG CTG GGG
TTT ATC GCC GGA CTG ATC GCC ATC GTG ATG GTG ACC ATC ATG CTG TGT
TGC ATG ACC AGC TGT TGT AGC TGT CTG AAA GGC TGT TGT AGC TGC GGC
AGC TGC TGC AAA TTT GAC GAG GAT GAT TCC GAG CCA GTG CTG AAG GGA
GTG AAA CTG CAC TAT ACC TGA
```

The following describes the sequence of the fusion CVN polypeptide insert of the invention.

(SEQ ID NO: 9)

```
MGLPNNTASWFTALTQHGKEDLKFPRGQGVPINTNSSPDDQIGYYRRATR
RIRGGDGKMKDLSPRWYFYYLGTGPEAGLPYGANKDGIIWVATEGALNTP
KDHIGTRNPANNAAIVLQLPQGTTLPKGFYAEGSRGGS
```

(SEQ ID NO: 10)

```
GGGGSGGGGSGGGGS↓GGGGSGGGGSGGGGSTKKSAAEASKKPRQKRTAT
KAYNVTQAFGRRGPEQTQGNFGDQELIRQGTDYKHWPQIAQFAPSASAFF
GMSRIGMEVTPSGTWLTYTGAIKLDDKDPNFKDQVILLNKHIDAYKTFP*
```

In the above sequence, SEQ ID NO: 9 is the sequence bound to the N-terminus of the SARS-CoV-2-B.1.1.351 Spike protein, SEQ ID NO: 10 is the sequence bound to the C-terminus, the underline indicates the linker, and the arrow indicates the SARS-Indicates the location where the CoV-2-B.1.1.351 Spike protein is inserted.

(SEQ ID NO: 11)

```
ATGGGCCTGCCCAACAACACCGCCAGCTGGTTTACCGCCCTGACCCAGCA
CGGCAAGGAGGACCTGAAGTTCCCCAGAGGCCAGGGCGTGCCCATTAACA
CCAACAGCAGCCCCGACGACCAGATCGGCTACTACAGAAGAGCCACCAGA
AGAATCAGAGGCGGCGACGGCAAGATGAAGGACCTGAGCCCCAGATGGTA
CTTCTACTATCTGGGAACCGGCCCCGAAGCCGGCCTGCCCTATGGCGCCA
ACAAAGATGGCATCATCTGGGTGGCCACCGAAGGCGCCCTGAACACCCCC
AAGGATCACATCGGAACCAGAAATCCCGCCAACAATGCCGCCATCGTGCT
GCAGCTGCCCCAGGGAACCACCCTGCCTAAAGGCTTTTATGCCGAAGGAA
GCAGAGGAGGAAGC
```

(SEQ ID NO: 12)

```
GGCGGCGGAGGAAGCGGCGGAGGAGGCAGCGGCGGAGGCGGAAGC↓GGCG
GAGGAGGAAGCGGCGGAGGCGGAAGCGGCGGCGGAGGAAGCACCAAAAAG
AGCGCCGCCGAGGCCAGCAAAAAGCCCAGACAGAAAAGAACCGCCACCAA
GGCCTACAATGTGACCCAGGCCTTTGGCAGAAGAGGACCCGAGCAGACCC
AGGGCAATTTTGGCGACCAGGAGCTGATCAGACAGGGCACCGACTACAAA
CACTGGCCCCAGATCGCCCAGTTCGCCCCCAGCGCCAGCGCCTTCTTCGG
CATGAGCAGAATCGGCATGGAGGTGACCCCCAGCGGCACCTGGCTGACCT
ACACCGGCGCCATCAAGCTGGACGACAAGGACCCCAACTTCAAGGACCAG
GTGATCCTGCTGAACAAGCACATCGACGCCTACAAGACCTTCCCCTGA
```

In the above sequence, SBQ ID NO: 11 is a gene sequence encoding a polypeptide bound to the N-terminus of the SARS-COV-2-B.1.1.351 Spike protein, and SEQ ID NO: 12 is a gene sequence encoding a polypeptide bound to the C-termins, The underline indicates the gene sequence encoding the linker, and the arrow indicates the location where the SARS-COV-2-B.1.1.351 Spike protein is inserted.

[ChimAd vector-based HPV vaccine sequence]

SEQ ID NO: 13

Human papillomavirus type 16, E6, E7 & Human pappillomavirus type 18, E6, E7 modified amino acid sequence (Linkder underlined)

```
MHQKRTAMFQDPQERPRKLPQLCTELQTTIHDIILECVYCKQQLLRREVY
DFAFRDLCIVYRDGNPYAVCDKCLKFYSKISEYRHYCYSLYGTTLEQQYN
KPLCDLLIRCIKQRHLDKKQRFHNIRGRWTGRCMSCCRSSRTRRETQLMH
GDTPTLHEYMLDLQPETTQLNDSSEEEDEIDGPAGQAEPDRAHYNIVTFC
CKCDSTLRLCVQSTHVDIRTLEDLLMGTLGIVCPICSQKPRGRKRRSMAR
FEDPTRRPYKLPDLCTELNTSLQDIEITCVYCKTVLELTEVFEFAFKDLF
VVYRDSIPHAACHKCIDFYSRIRELRHYSDSVYGDTLEKLINTGLYNLLI
RCLKLRHLNEKRRFHNIAGHYRGQCHSCCNRARQERLQRRRETQVMHGPK
ATLQDIVLHLEPQNEIPVQLSDSEEENDEIDGVNHQHLPARRAEPQRHTM
LCMCCKCEARIELVVESSADDLRAFQQLFLNTLSFVCPWCASQQ
```

SEQ ID NO: 14

Human papillomavirus type 16, E6, E7 & Human papillomavirus type 18, E6, E7 modified nucleic acid sequence (linker underlined)

```
ATGCACCAGAAGAGAACAGCCATGTTCCAGGACCCTCAGGAACGGCCACG
GAAGCTCCCACAACTTTGTACAGAGCTGCAAACAACCATTCATGACATCA
TCCTTGAATGCGTTTACTGCAAGCAGCAACTTCTGCGCCGGGAAGTCTAC
GATTTCGCTTTCAGAGATCTGTGCATCGTGTATAGAGACGGGAACCCCTA
CGCCGTGTGTGACAAATGCCTTAAATTCTACAGTAAGATTTCAGAGTACC
GGCATTATTGCTACAGCCTTTATGGAACTACATTGGAGCAGCAGTACAAC
AAACCTTTGTGCGATCTTCTTATCCGGTGCATTAAGCAACGGCACTTGGA
CAAAAAACAACGGTTCCATAACATCAGGGGCAGGTGGACTGGACGCTGCA
TGAGTTGCTGTCGCTCAAGCCGCACTCGGAGAGAGACTCAACTGATGCAT
GGTGATACTCCAACTTTGCACGAATATATGTTGGACCTCCAACCCGAAAC
TACCCAACTGAATGACAGCTCTGAGGAAGAGGACGAAATCGACGGCCCTG
CAGGGCAAGCCGAACCTGACAGGGCCCATTATAACATTGTGACATTTTGC
TGCAAATGCGATAGTACTTTGAGACTCTGTGTGCAGTCAACTCATGTTGA
CATTAGAACACTTGAAGACCTCCTCATGGGGACACTGGGGATTGTTTGCC
CAATCTGTTCACAGAAACCCAAGAGGCCGCAAAAGGCGGTCTATGGCTCG
CTTTGAGGACCCTACAAGGAGGCCCTACAAGCTCCCCGATTTGTGTACAG
AACTGAATACCAGTCTTCAGGATATTGAAATCACTTGCGTCTACTGCAAA
ACTGTGCTCGAACTTACCGAAGTCTTTGAATTTGCCTTCAAGGACCTTTT
TGTTGTGTATCGCGATTCAATCCCACACGCAGCCTGTCACAAATGTATTG
ACTTCTACTCTAGGATCAGAGAATTGAGGCACTATTCAGACTCTGTGTAT
GGCGACACCTTGGAAAAATTGACCAACACTGGATTGTATAATCTGCTTAT
TCGGTGTCTTAAGCTCCGGCACTTGAACGAAAAACGCAGATTCCACAACA
TTGCCGGGCATTATCGCGGGCAATGCCATTCTTGTTGCAATCGCGCCCGC
CAGGAGCGGCTGCAAAGGCGCAGAGAGACTCAGGTGATGCATGGACCCAA
GGCCACTCTCCAGGACATCGTCCTTCATCTTGAACCCCAGAACGAAATTC
CCGTTCAACTTAGCGACTCAGAAGAAGAAAATGATGAAATCGACGGAGTG
AACCATCAGCATCTCCCAGCAAGAAGAGCCGAGCCACAAAGACACACAAT
GCTCTGTATGTGCTGCAAGTGTGAAGCACGGATCGAACTCGTCGTCGAAT
CTAGTGCAGATGATCTCAGAGCCTTTCAACAGCTCTTCTTGAATACACTG
AGCTTTGTCTGTCCATGGTGCGCTAGTCAACAA
```

The invention claimed is:

1. A chimeric adenovirus vector comprising:

a gene encoding a fiber protein comprising a tail domain and a shaft domain of human adenovirus serotype 5 and a knob domain of chimpanzee adenovirus serotype 6; and a gene encoding a chimeric hexon protein comprising hypervariable regions 1-7 of human adenovirus serotype 28, wherein the chimeric hexon protein comprises the amino acid sequence of SEQ ID NO: 3.

2. The chimeric adenovirus vector according to claim 1, wherein the the knob domain of chimpanzee adenovirus serotype 6 comprises the amino acid sequence of SEQ ID NO: 1.

3. The chimeric adenovirus vector according to claim 1, wherein the knob domain of chimpanzee adenovirus serotype 6 is encoded by the nucleic acid sequence of SEQ ID NO: 2.

4. The chimeric adenovirus vector according to claim 1, wherein the gene encoding the chimeric hexon protein comprises the nucleic acid sequence of SEQ ID NO: 4.

5. The chimeric adenovirus vector of claim 1, wherein the vector comprises as an insert a) a gene encoding the spike protein of a coronavirus, or b) a gene encoding the E6 and E7 proteins of human papillomavirus type 16 or 18.

6. A host cell transformed with the chimeric adenovirus vector of claim 1.

7. The host cell according to claim 6, wherein the cell is HEK293, PERC6 or 911 cell.

8. An isolated polypeptide encoded by the chimeric adenovirus vector of claim 1.

* * * * *